(12) United States Patent
Orentas et al.

(10) Patent No.: US 11,453,712 B2
(45) Date of Patent: Sep. 27, 2022

(54) COMPOSITIONS AND METHODS FOR TREATING CANCER WITH DUOCARS

(71) Applicant: Lentigen Technology, Inc., Gaithersburg, MD (US)

(72) Inventors: Rimas Orentas, Seattle, WA (US); Dina Schneider, Potomac, MD (US); Waleed M. Haso, Fair Lawn, NJ (US); Stefan Miltenyi, Bergisch Gladbach (DE); Boro Dropulic, Ellicott City, MD (US)

(73) Assignee: Lentigen Technology Inc., Gaithersburg, MD (US)

( * ) Notice: Subject to any disclaimer, the term of this patent is extended or adjusted under 35 U.S.C. 154(b) by 0 days.

(21) Appl. No.: 16/078,269

(22) PCT Filed: Sep. 1, 2017

(86) PCT No.: PCT/US2017/049923
§ 371 (c)(1),
(2) Date: Aug. 21, 2018

(87) PCT Pub. No.: WO2018/045325
PCT Pub. Date: Mar. 8, 2018

(65) Prior Publication Data
US 2019/0241641 A1 Aug. 8, 2019

Related U.S. Application Data

(60) Provisional application No. 62/382,791, filed on Sep. 2, 2016.

(51) Int. Cl.
| | | |
|---|---|---|
| C12N 15/63 | (2006.01) |
| C12N 15/13 | (2006.01) |
| C07K 14/47 | (2006.01) |
| A61K 39/395 | (2006.01) |
| C07K 14/725 | (2006.01) |
| C07K 14/705 | (2006.01) |
| C07K 16/28 | (2006.01) |
| A61P 35/02 | (2006.01) |
| A61K 39/00 | (2006.01) |
| A61K 35/17 | (2015.01) |
| C12N 15/85 | (2006.01) |

(52) U.S. Cl.
CPC .......... *C07K 14/7051* (2013.01); *A61K 35/17* (2013.01); *A61K 39/001112* (2018.08); *A61K 39/001124* (2018.08); *A61P 35/02* (2018.01); *C07K 14/70517* (2013.01); *C07K 14/70521* (2013.01); *C07K 14/70578* (2013.01); *C07K 16/2803* (2013.01); *C07K 16/2887* (2013.01); *C12N 15/85* (2013.01); *A61K 2039/5156* (2013.01); *C07K 2317/31* (2013.01); *C07K 2317/622* (2013.01); *C07K 2319/00* (2013.01); *C07K 2319/02* (2013.01); *C07K 2319/03* (2013.01); *C07K 2319/75* (2013.01)

(58) Field of Classification Search
None
See application file for complete search history.

(56) References Cited

U.S. PATENT DOCUMENTS

| | | | |
|---|---|---|---|
| 10,689,431 B2 | 6/2020 | Orentas | |
| 2005/0136428 A1* | 6/2005 | Crea | ...................... C07K 16/00 506/11 |
| 2015/0299317 A1* | 10/2015 | Orentas | .............. A61K 39/0011 424/134.1 |
| 2016/0145337 A1 | 5/2016 | Galletto | |
| 2016/0311910 A1 | 10/2016 | Qin | |
| 2017/0107286 A1 | 4/2017 | Kochenderfer | |
| 2017/0183418 A1 | 6/2017 | Galletto | |
| 2018/0092968 A1 | 4/2018 | Albelda | |
| 2018/0148508 A1* | 5/2018 | Wang | .................. C07K 16/2863 |
| 2018/0280438 A1 | 10/2018 | Orentas | |
| 2019/0083596 A1 | 3/2019 | Orentas et al. | |
| 2019/0119635 A1* | 4/2019 | Robbins | .................. A61K 35/17 |
| 2019/0134091 A1* | 5/2019 | Dropulic | ................. A61K 35/17 |
| 2020/0231648 A1 | 7/2020 | Orentas et al. | |
| 2020/0392200 A1 | 12/2020 | Orentas et al. | |

FOREIGN PATENT DOCUMENTS

| | | |
|---|---|---|
| CN | 103483453 | 1/2014 |
| CN | 104822705 | 8/2015 |
| CN | 105331586 | 2/2016 |

(Continued)

OTHER PUBLICATIONS

Sridhar and Petrocca, Regional Delivery of Chimeric Antigen Receptor (CAR) T-Cells for Cancer Therapy, Cancers, 2017, pp. 1-10.*
D'Alota etal, CAR-T cells: the long and winding road to solid tumors, Cell Death and Disease (2018) 9:282, pp. 1-12.*
Fumoto et al, Targeted Gene Delivery: Importance of Administration Routes, Intech, 2013, pp. 1-31.*
Breener and Okur, Overview of gene therapy clinical progress including cancer treatment with gene-modified T cells, Hematology Am Soc Hematol Educ Program. 2009 ; : 675-681.*
Kuerberuwa et al, CD19 CAR T Cells Expressing IL-12 Eradicate Lymphoma in Fully Lymphoreplete Mice through Induction of Host Immunity, Molecular therapy, Oncolytics, 2018, pp. 41-51.*

(Continued)

*Primary Examiner* — Maria Marvich
(74) *Attorney, Agent, or Firm* — Serge Sira, Esq.; Gregory J. Hwa, Esq.; Fish & Richardson P.C.

(57) ABSTRACT

Novel therapeutic immunotherapy compositions comprising at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs are provided herein as well as are methods of use of same in a patient-specific immunotherapy that can be used to treat cancers and other diseases and conditions.

8 Claims, 9 Drawing Sheets
Specification includes a Sequence Listing.

(56) References Cited

FOREIGN PATENT DOCUMENTS

| WO | WO2014055657 | 4/2014 |
| WO | WO 2014065961 | 5/2014 |
| WO | 2015-513394 | 5/2015 |
| WO | WO2015075468 | 5/2015 |
| WO | WO2016102965 | 6/2016 |
| WO | WO 2017062952 | 4/2017 |
| WO | WO 2018045325 | 3/2018 |

OTHER PUBLICATIONS

Brentjens et al., Safety and persistence of adoptively transferred autologous CD19-targeted T cells in patients with relapsed or chemotherapy refractory B-cell leukemias, Blood, Nov. 3, 2011, pp. 4817-4828.*
Jensen et al., Antitransgene Rejection Responses Contribute to Attenuated Persistence of Adoptively Transferred CD20/CD19-Specific Chimeric Antigen Receptor Redirected T Cells in Humans, Biol Blood Marrow Transplant 16: 1245-1256 (2010).*
Zah et al, T Cells Expressing CD19/CD20 Bispecific Chimeric or Antigen Receptors Prevent Antigen Escape by Malignant B Cells, Cancer Immunol Res; 4(6); 498-508. 2016.*
Xiong et al., Mitigating Tumor Escape: Tandem Anti-CD20- and CD19 SCFV-Based Chimeric Antigen Receptors (CARs) in Leukemia/Lymphoma, Molecular Therapy vol. 24, Supplement 1, May 2016, S257 #648.*
Bielamowicz et al., "Multispecific CAR T cells for the treatment of high grade glioma", Neuro Oncol. 17(Suppl. 3): iii16, Jun. 2015.
Hedge et al., "Combinational targeting offsets antigen escape and enhances effector functions of adoptively transferred T cells in glioblastoma", Molecular Therapy 21(11): 2087-2101, 2013.
Chen, et al., "A compound chimeric antigen receptor strategy for targeting multiple myeloma," Leukemia, 2018, 32(2):402-412.
Mirzaei, et al, "Chimeric Antigen Receptors T Cell Therapy in Solid Tumor: Challenges and Clinical Applications," Frontiers in Immuology, 2017, 8:1850, 13 pages.
NEBiolabs, Recleavable Filled-in 5' Overhangs, downloaded Jan. 20, 2019, 2 pages.
Newick, et al, "Chimeric antigen receptor T-cell therapy for solid tumors," Molecular Therapy—Oncolytics, 2016, 3:16006, 7 pages.
Bielamowicz, et al., "Trivalent CAR T cells overcome interpatient antigenic variability in glioblastoma," Neuro-Oncology, Sep. 2017,20(4):506-518.
Fousek, et al., "Targeting CD19-negative relapsed B-acute lymphoblastic leukemia using trivalent CAR T cells," J. Clin. Oncol., Feb. 2018, 36(5 Suppl 1):121.
Fousek, et al., "Trivalent CAR T cells mitigate CD19-negative relapse and improve tumor control in primary pre-B cell acute lymphoblastic leukemia (B-ALL) (Abstract A50)," Proceedings of the AACR Special Conference on Tumor Immunology and Immunotherapy, Sep. 2018, 6(9):Suppl 1.
Eisenberg et al., "T-cells "àla CAR-T (e)"—Genetically engineering T-cell response against cancer," Advanced Drug Delivery—Reviews, Feb. 15, 2019, 141:23-40.
Office Action in Chinese Application No. 201780061243.8, dated Jan. 26, 2022, 21 pages (with English translation).
PCT International Preliminary Report on Patentability in International Application No. PCT/2020/061623, dated Jun. 2, 2022, 9 pages.

* cited by examiner

COMPOSITIONS AND METHODS FOR TREATING CANCER WITH DUOCARS

CROSS-REFERENCE TO RELATED APPLICATIONS

This application is a 371 U.S. National Phase Application of PCT/US2017/049923, filed on Sep. 1, 2017, which claims the benefit of priority under 35 U.S.C. Section 119(e) to U.S. Provisional Patent Application No. 62/382,791, filed on Sep. 2, 2016. The entire contents of each of the foregoing applications are incorporated herein by reference.

FIELD OF THE DISCLOSURE

This application relates to the field of cancer, particularly to a composition comprising at least two vectors encoding functional chimeric antigen receptors and methods of use of same in patient-specific immunotherapy.

SEQUENCE LISTING

The instant application contains a Sequence Listing which has been submitted electronically in ASCII format and is hereby incorporated by reference in its entirety. Said ASCII copy, created on Sep. 11, 2019, is named Sequence_Listing.txt and is 124 kilobytes in size.

BACKGROUND OF THE INVENTION

Cancer is one of the deadliest threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making treatment extremely difficult. One of the difficulties in modern cancer treatments is the amount of time that elapses between a biopsy and the diagnosis of cancer, and effective treatment of the patient. During this time, a patient's tumor may grow unimpeded, such that the disease has progressed further before treatment is applied. This negatively affects the prognosis and outcome of the cancer.

Chimeric Antigen Receptors (DuoCARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4): e23621). The antigen-binding motif of a CAR is commonly fashioned after a single chain Fragment variable (scFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al Clin Cancer Res. 2012; 18(8):2199-209; Lehner M et al. PLoS One. 2012; 7 (2): e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the scFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al J Immunol. 2009; 183 (9): 5563-74). With the advent of new technology, the activation of T cells with beads linked to anti-CD3 and anti-CD28 antibody, the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia. Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, La.; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

Current challenges in the more widespread and effective adaptation of CAR therapy for cancer relate to a paucity of compelling targets. Creating binders to cell surface antigens is now readily achievable, but discovering a cell surface antigen that is specific for tumor while sparing normal tissues remains a formidable challenge. One potential way to imbue greater target cell specificity to CAR-expressing T cells is to use combinatorial CAR approaches. In one system, the CD3-ζ and CD28 signal units are split between two different CAR constructs expressed in the same cell; in another, two DuoCARs are expressed in the same T cell, but one has a lower affinity and thus requires the alternate CAR to be engaged first for full activity of the second (Lanitis E et al. Cancer Immunol Res. 2013; 1(1):43-53; Kloss C C et al. Nat Biotechnol. 2013; 31(1):71-5). A second challenge for the generation of a single scFv-based CAR as an immunotherapeutic agent is tumor cell heterogeneity. At least one group has developed a CAR strategy for glioblastoma whereby the effector cell population targets multiple antigens (HER2, IL-13Ra, EphA2) at the same time in the hope of avoiding the outgrowth of target antigen-negative populations (Hegde M et al. Mol Ther. 2013; 21 (11):2087-101).

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-β by the expression of a decoy receptor further demonstrates that degree to which effector T cells can be engineered for optimal antitumor activity (Foster A E et al. J Immunother. 2008; 31(5):500-5).

Thus, while it appears that CARs can trigger T-cell activation in a manner similar to an endogenous T-cell receptor, a major impediment to the clinical application of CAR-based technology to date has been limited in vivo expansion of CAR+ T cells, rapid disappearance of the cells after infusion, disappointing clinical activity, relapse of the underlying medical disease or condition, and the undue length of time that elapses between diagnosis and timely treatment of cancer using such CAR+ T cells.

Accordingly, there is an urgent and long felt need in the art for discovering compositions and methods for treatment of cancer using a CAR-based therapy that can exhibit cancer-specific intended therapeutic attributes without the aforementioned short comings.

The present invention addresses these needs by providing compositions comprising at least two vectors encoding functional chimeric antigen receptors and methods of use of same in patient-specific immunotherapy that can be used to treat cancers and other diseases and/or conditions.

In particular, the present invention as disclosed and described herein provides an immunotherapy composition comprising one or more isolated nucleic acid molecules encoding at least two vectors, each vector encoding a functional DuoCAR, whereby the combination of vectors results in the expression of two or more non-identical binding domains, wherein each vector encoded binding domain(s) are covalently linked to a transmembrane domain and one or more non-identical intracellular signaling motifs, which immunotherapy composition may be used to transduce autologous lymphocytes to generate active patient-specific anti-tumor lymphocyte cell populations that can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

SUMMARY OF THE INVENTION

Novel adoptive immunotherapy compositions comprising two or more vector-transduced lymphocytes are provided herein as well as are methods of use of same in a patient-specific combination immunotherapy that can be used to treat cancers and other diseases and conditions.

Thus, in one aspect, lentiviral vectors expressing Duo chimeric antigen receptors (DuoCARs) are provided herein, as well as nucleic acid molecules encoding the lentiviral vectors expressing DuoCARs. Methods of using the disclosed lentiviral vectors expressing DuoCARs, host cells, and nucleic acid molecules are also provided, for example, to treat a cancer in a subject.

In one aspect, an immunotherapy composition is provided comprising one or more isolated nucleic acid molecules encoding at least two vectors (DuoCARs), each vector encoding a functional CAR, wherein at least one binding domain(s) in one of the vectors are non-identical, and whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least three vectors (TrioCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In one embodiment, an immunotherapy composition is provided comprising one or more isolated nucleic acid molecules encoding at least four vectors (QuatroCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In yet another embodiment, an immunotherapy composition is provided comprising one or more isolated nucleic acid molecules encoding at least two, three, four, five, six, seven, eight, nine, or ten vectors (e.g., an "nCAR"), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, wherein each unique member of the nCAR set when assembled into a CAR product constitutes a unique CAR composition referred to herein as "n-SET" (e.g., Duo-SET, Trio-SET, Quatro-SET, Penta-SET, Hexa-SET, Hepta-SET, Octa-SET, Nona-SET, and Deca-SET, etc.).

In one embodiment, an immunotherapy composition is provided comprising: (a) at least two vectors, each comprising nucleic acid sequences that are functional in cells; (b) wherein each vector encodes a functional CAR; (c) wherein each CAR comprises of at least one binding domain, a single transmembrane domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In another embodiment, an immunotherapy composition is provided comprising: (a) at least two vectors, each comprising nucleic acid sequences that are functional in cells; (b) wherein each vector encodes a functional CAR; (c) wherein each CAR comprises at least one binding domain, a single transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In one embodiment, an immunotherapy composition is provided wherein each vector encodes more than one functional CAR.

In another embodiment, an immunotherapy composition is provided wherein one or more signaling motifs combinations are identical on one or more vectors.

In another embodiment, an immunotherapy composition is provided wherein one or more multiple binding domains are identical on one or more vectors.

In another embodiment, an immunotherapy composition is provided wherein the lymphocyte population(s) comprise autologous T-cells or a mixture of peripheral blood derived lymphocytes.

In another embodiment, an immunotherapy composition is provided wherein the at least one extracellular antigen binding domain of the CAR comprises at least one single chain variable fragment of an antibody that binds to the antigen.

In another embodiment, an immunotherapy composition is provided wherein the at least one extracellular antigen binding domain of the CAR comprises at least one heavy chain variable region of an antibody that binds to the antigen.

In another embodiment, an immunotherapy composition is provided wherein the at least one extracellular antigen binding domain of the CAR, the at least one intracellular signaling domain of the CAR, or both are connected to the transmembrane domain by a linker or spacer domain.

In another embodiment, an immunotherapy composition is provided wherein the extracellular antigen binding domain of the CAR is preceded by a leader peptide.

In another embodiment, an immunotherapy composition is provided wherein the extracellular antigen binding domain of the CAR targets an antigen comprising CD19, CD20, CD22, ROR1, TSLPR, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1, MAGE-A3, PRAME peptides in combination with MHC, or any combination thereof.

In another embodiment, an immunotherapy composition is provided wherein the extracellular antigen binding domain of the CAR comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33 scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESO-1 TCR (including single chain TCR constructs) antigen binding domain, an anti-MAGE-A3 TCR, or an amino acid sequence with 85%, 90%, 95%, 96%, 97%, 98% or 99% identity thereof, or any combination thereof.

In another embodiment, an immunotherapy composition is provided wherein the linker or spacer domain of the CAR is derived from the extracellular domain of CD8, and is linked to the transmembrane domain.

In another embodiment, an immunotherapy composition is provided wherein the CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof.

In another embodiment, an immunotherapy composition is provided wherein the at least one intracellular signaling domain further comprises a CD3 zeta intracellular domain.

In another embodiment, an immunotherapy composition is provided wherein the at least one intracellular signaling domain is arranged on a C-terminal side relative to the CD3 zeta intracellular domain.

In another embodiment, an immunotherapy composition is provided wherein the at least one intracellular signaling domain comprises a costimulatory domain, a primary signaling domain, or any combination thereof.

In another embodiment, an immunotherapy composition is provided wherein the at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), PD-1, GITR, CTLA-4, or any combination thereof.

In another embodiment, an immunotherapy composition is provided wherein a single vector is used to encode all chimeric antigen receptors (e.g., retroviral, adenoviral, SV40, herpes vector, PDX vector, RNA, plasmid, cosmid, or any viral vector or non-viral vector), in combination with a CRISPR system for integration.

In another embodiment, an immunotherapy composition is provided wherein each vector is an RNA or DNA vector, alone or in combination with a transfection reagent or a method to deliver the RNA or DNA into the cell, a non-limiting example being electroporation.

In another embodiment, an immunotherapy composition is provided wherein at least one vector expresses a nucleic acid molecule that modulates the expression of a nucleic acid in the cell.

In another embodiment, an immunotherapy composition is provided wherein the nucleic acid molecule inhibits or deletes the expression of an endogenous gene.

In certain embodiments, an immunotherapy composition is provided wherein the active patient-specific autologous anti-tumor lymphocyte cell population is generated within one day, two days, three days, four days, five days, seven days, ten days, twelve days, fourteen days, twenty-one days, or one month of lymphocyte harvest or tumor biopsy and wherein the active patient-specific autologous anti-tumor lymphocyte cell population that can be infused back into a patient suffering from cancer and is capable of promoting in vivo expansion, persistence of patient-specific anti-tumor lymphocyte cells resulting in tumor stabilization, reduction, elimination, remission of cancer, or prevention or amelioration of relapse of cancer, or a combination thereof, in a patient-specific manner.

In one aspect, isolated nucleic acid molecules encoding the aforementioned chimeric antigen receptors are provided herein.

In one aspect of the DuoCARs used in the patient-specific autologous lymphocyte population(s) of the immunotherapy composition of the present invention, the DuoCARs are modified to express or contain a detectable marker for use in diagnosis, monitoring, and/or predicting the treatment outcome such as progression free survival of cancer patients or for monitoring the progress of such treatment. In one embodiment of the DuoCARs used in the patient-specific autologous anti-tumor lymphocyte cell population(s), the nucleic acid molecules encoding the disclosed DuoCARs can be contained in a vector, such as a viral or non-viral vector. The vector is a DNA vector, an RNA vector, a plasmid vector, a cosmid vector, a herpes virus vector, a measles virus vector, a lentiviral vector, adenoviral vector, or a retrovirus vector, or a combination thereof.

In certain embodiments of the DuoCARs used in the patient-specific autologous anti-tumor lymphocyte cell population(s), the two or more lentiviral vectors are pseudotyped with different viral glycoproteins (GPs) including for example, and not by way of limitation, amphotropic murine leukemia virus [MLV-A], a baboon endogenous virus (BaEV), GP164, gibbon ape leukemia virus [GALV], RD114, feline endogenous virus retroviral-derived GPs, and vesicular stomatitis virus [VSV], measles virus, fowl plague virus [FPV], Ebola virus [EboV], lymphocytic choriomeningitis virus [LCMV]) non retroviral-derived GPs, as well as chimeric variants thereof including, for example, and not by way of limitation, chimeric GPs encoding the extracellular and transmembrane domains of GALV or RD114 GPs fused to the cytoplasmic tail (designated TR) of MLV-A GP.

In certain embodiments of the DuoCARs used in the patient-specific autologous anti-tumor lymphocyte cell population(s), the vector further comprises a promoter wherein the promoter is an inducible promoter, a tissue specific promoter, a constitutive promoter, a suicide promoter or any combination thereof.

In yet another embodiment of the DuoCARs used in the patient-specific autologous anti-tumor lymphocyte cell population(s), the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect of the DuoCARs used in the patient-specific autologous anti-tumor lymphocyte cell population(s), host cells including the nucleic acid molecule(s) encoding the DuoCARs are also provided. In some embodiments, the host cell is a T cell, such as a primary T cell obtained from a subject. In one embodiment, the host cell is a CD8+ T cell. In one embodiment the host cell is a CD4+ T cell. In one embodiment the host cells are selected CD4+ and CD8+ lymphocytes purified directly from a patient product without regard to proportionality. In another embodiment the number of CD4+ and CD8+ T cells in the product are specific. In another embodiment specific subsets of T cells are utilized as identified by phenotypic markers including T naïve cells (Tn), T effector memory cells (Tem), T central memory cells (Tcm), T regulatory cells (Treg), induced T regulatory cells (iTreg), T suppressor cells (Ts), T stem cell memory cells (Tscm), Natural Killer (NK) cells, and lymphokine activated killer (LAK) cells.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising nucleic acid molecules encoding at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR; (c) wherein each CAR comprises of at least one binding domain, at least one transmembrane domain, at least one linker domain, and at least one intracellular signaling motif; (d) wherein the at least one binding domains in one of the vectors are non-identical; and (e) wherein the at least one binding domain, a single transmembrane domain, at least one linker domain, and at least one intracellular signaling motif are covalently linked in each said vector, wherein the combination of vectors are used to genetically modify one or more lymphocyte populations.

In yet another embodiment, a pharmaceutical composition is provided comprising an anti-tumor effective amount of an immunotherapy composition comprising a population of patient-specific autologous anti-tumor lymphocyte cell population(s) of a human having a cancer, wherein the cells of the population include cells comprising (a) nucleic acid molecules encoding two or more vectors; (b) wherein each vector encodes a functional CAR; (c) wherein each CAR comprises at least one binding domain, at least one transmembrane domain, at least one linker domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, at least one linker domain, and at least one intracellular signaling motif are covalently linked in each said vector, wherein the combination of two or more vectors are used to genetically modify one or more lymphocyte populations.

In one embodiment, the cancer is a refractory cancer non-responsive to one or more chemotherapeutic agents. The cancer includes hematopoietic cancer, myelodysplastic syndrome, pancreatic cancer, head and neck cancer, cutaneous tumors, minimal residual disease (MRD) in acute lymphoblastic leukemia (ALL), acute myeloid leukemia (AML), lung cancer, breast cancer, ovarian cancer, prostate cancer, colon cancer, melanoma or other hematological cancer and solid tumors, or any combination thereof. In another embodiment, the cancer includes a hematological cancer such as leukemia (e.g., chronic lymphocytic leukemia (CLL), acute lymphocytic leukemia (ALL), acute myeloid leukemia (AML), or chronic myelogenous leukemia (CML), lymphoma (e.g., mantle cell lymphoma, non-Hodgkin's lymphoma or Hodgkin's lymphoma) or multiple myeloma, or any combination thereof.

In yet another embodiment, the cancer includes an adult carcinoma comprising coral and pharynx cancer (tongue, mouth, pharynx, head and neck), digestive system cancers (esophagus, stomach, small intestine, colon, rectum, anus, liver, intrahepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In another aspect, a pharmaceutical composition is provided comprising an autologous lymphocyte cell population transduced with two or more lentiviral vectors encoding single or multiple chimeric antigen receptors (DuoCARs), thereby generating a patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a pharmaceutical composition is provided comprising an autologous T cell population transduced with one or more lentiviral vectors encoding single or multiple chimeric antigen receptors (DuoCARs) to generate an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, methods of making active patient-specific autologous anti-tumor Duo CAR-containing lymphocyte cells are provided. The methods include transducing a lymphocyte cell with two or more vectors or nucleic acid molecule encoding two or more chimeric antigen receptors (DuoCARs) that specifically bind an antigen, thereby making active patient-specific autologous anti-tumor Duo CAR-containing lymphocyte cells.

In yet another aspect, a method of generating a population of RNA-engineered lymphocyte cells is provided that comprises introducing an in vitro transcribed RNA or synthetic RNA of a nucleic acid molecule encoding a two or more chimeric antigen receptors (DuoCARs) into a cell population of a subject, thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with one or more lentiviral vectors encoding single or multiple chimeric antigen receptors (DuoCARs) thereby generating an patient-specific autologous anti-tumor lymphocyte cell population capable of promoting in vivo expansion, persistence of patient-specific anti-tumor T-cells resulting in tumor stabilization, reduction, elimination, remission of cancer, or prevention or amelioration of relapse of cancer, or a combination thereof, in a patient-specific manner.

In another aspect, a method is provided for treating a mammal having a disease, disorder or condition associated with an elevated expression of a tumor antigen, the method comprising administering to the subject a pharmaceutical composition comprising an anti-tumor effective amount of an autologous lymphocyte cell population transduced with two or more lentiviral vectors encoding single or multiple chimeric antigen receptors (DuoCARs) to generate an patient-specific autologous anti-tumor lymphocyte cell population which can be infused directly back into the patient to promote in vivo expansion, persistence of patient-specific anti-tumor T-cells resulting in tumor stabilization, reduction, elimination, or remission of cancer, or prevention or amelioration of relapse of cancer, or any combination thereof, in a patient-specific manner.

In one embodiment, a method is provided for treating a mammal having a disease, disorder or condition associated with an elevated expression of a tumor antigen, the method comprising administering to the subject a pharmaceutical composition comprising at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, and a pharmaceutically acceptable excipient, wherein the combination of vectors are used to genetically modify one or more lymphocyte populations.

In another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional CAR; (c) wherein each CAR comprises of at least one binding domain, at least one transmembrane domain, and at least one intracellular signaling motif; (d) wherein the at least one binding domains in one of the vectors are non-identical; and (e) wherein the at least one binding domain, a single transmembrane domain, and at least one intracellular signaling motif are covalently linked in each said vector, wherein the combination of vectors are used to genetically modify one or more lymphocyte populations.

In yet another embodiment, a method is provided for treating a mammal having a disease, disorder or condition associated with an elevated expression of a tumor antigen, the method comprising administering to the subject a pharmaceutical composition comprising (a) nucleic acid molecules encoding two or more vectors; (b) wherein each vector encodes a functional CAR; (c) wherein each CAR comprises at least one binding domain, at least one transmembrane domain, and at least one intracellular signaling motif; (d) wherein the at least one binding domain(s) in each vector are non-identical; (e) wherein the at least one signaling motif combinations are non-identical between each of the vectors; and (f) wherein the at least one binding domain, a single transmembrane domain, and at least one intracellular signaling motif are covalently linked in each said vector, wherein the combination of two or more vectors are used to genetically modify one or more lymphocyte populations.

In certain embodiments, the genetically modified lymphocytes are autologous T cell lymphocytes, and wherein the autologous or allogeneic T cell lymphocytes are infused directly back into the patient so as to prevent or ameliorate relapse of malignant disease.

In certain other embodiments, the genetically modified lymphocytes are autologous T cell lymphocytes, and wherein the autologous lymphocytes are infused directly back into the patient to promote in vivo expansion, persistence of patient-specific anti-tumor T-cell lymphocytes resulting in tumor stabilization, reduction, elimination, or remission of cancer, or prevention or amelioration of relapse of cancer, or any combination thereof, in a patient-specific manner.

In yet another embodiment, the T cell has been preselected by virtue of expressing specific activation or memory-associated surface markers.

In yet another embodiment, the T cell is derived from a hematopoietic stem cell donor, and wherein the procedure is carried out in the context of hematopoietic stem cell transplantation.

In certain embodiments, a method is provided wherein the lymphocyte cell has been preselected by virtue of expressing specific activation or memory-associated surface markers.

In certain embodiments, a method is provided herein wherein the lymphocyte cell is a T cell and is derived from a hematopoietic stem cell donor, and wherein the procedure is carried out in the context of hematopoietic stem cell transplantation.

In yet another aspect, a method is provided for generating a persisting population of genetically engineered patient-specific autologous anti-tumor lymphocyte cell population(s) in a human diagnosed with cancer. In one embodiment, the method comprises administering to a human patient in need thereof one or more patient-specific autologous anti-tumor lymphocyte cell population(s) described herein, wherein the persisting population of patient-specific autologous anti-tumor lymphocyte cell population(s), or the population of progeny of the lymphocyte cells, persists in the human for at least one month, two months, three months, four months, five months, six months, seven months, eight months, nine months, ten months, eleven months, twelve months, two years, or three years after administration.

In one embodiment, the progeny lymphocyte cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using a patient-specific autologous anti-tumor lymphocyte cell population(s) comprising one or more of the Duo Car immunotherapeutic compositions as disclosed herein.

In yet another aspect, a kit is provided for making a DuoCar immunotherapeutic composition comprising a patient-specific autologous anti-tumor lymphocyte cell population(s) as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

While the compositions and methods of the present invention have been illustrated with reference to the generation and utilization of DuoCARs, it is contemplated herein that the compositions and methods are specifically intended to include the generation and utilization of TrioCARs and QuatroCARs.

In yet another aspect, an immunotherapy composition comprising one or more isolated nucleic acids encoding at least one vector, wherein said vector contains a nucleic acid sequence that results in at least one messenger RNA (i.e., a multi-cistronic nucleic acid or a nucleic acid resulting in more than one transcript) encoding a Duo CAR, resulting in the ability to bind two or more non-identical antigen targets, thereby generating multiple antigen specificities residing in a single cell expressing said vector.

In yet another aspect, an immunotherapy composition comprising one or more isolated nucleic acids encoding at least two vectors, as described supra, wherein each vector further encodes a functional tag or anti-tag binding moiety (AT-CAR) that reconstitutes a functional chimeric antigen receptor upon co-incubation or co-administration of a soluble binder (such as a tagged scFv, or a scFv linked to an anti-tag binder), whereby the combination of the two vectors results in the ability to bind two or more non-identical antigen binding domains, resulting in multiple antigen specificities residing in a cell expressing these two vectors.

In yet another aspect, an immunotherapy composition comprising one or more isolated nucleic acids encoding at least two vectors, as described supra, wherein each vector encoding a functional tag or anti-tag binding moiety (AT-CAR) that reconstitutes a functional chimeric antigen receptor upon co-incubation or co-administration of a soluble binder (such as a tagged scFv, or a scFv linked to an anti-tag binder), wherein each vector expresses a unique tag (or anti-tag) that can bind soluble protein or protein modified structures resulting in multiple antigen specificities, or wherein each vector expresses a unique tag (or anti-tag) that binds only one of the soluble binding domains resulting in a specific linkage of the AT-CAR encoded intracellular signaling motifs to the antigen-binding domains of the tagged (or anti-tagged) binder.

In a non-limiting embodiment for the manufacture of DuoCAR vectors, the each of the compositions and methods disclosed in the embodiments and aspects referred to supra, the two vectors can be made separately and then added to the T cells sequentially or at the same time. In another non limiting embodiment, the plasmid DNA of the two or more vectors can be combined before or during transfection of production cells, or integrated in the production cells genome, to produce a mixture of viral vectors that contain the multiple DuoCAR vector particles, subsequently used for the transduction and genetic modification of patient T Cells.

It will be understood that the patient-specific autologous anti-tumor lymphocyte cell population(s), the two or more lentiviral vectors expressing chimeric antigen receptors (DuoCARs), host cells, and methods as described supra are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Definitions

Figure 1:
FIG. 1 depicts four (4) Products (Examples 1 through 4) that can be produced as discrete commercial entities. These DuoCARs sets can be created to target human B cell malignancies expressing three leukemia-associated antigens, CD19, CD20, and CD22. In Product 1, two gene vectors are used to co-transduce an activated T cell population. The first vector encodes two antigen binding domains (CD19, CD20) linked to a single intracellular domain (z, CD3 zeta chain) connected by virtue of a CD8 transmembrane region (8). The second vector encodes a CD22 binding domain and two signaling domains (BB, derived from CD137/4-1BB; and z). The second Product, Example 2, feature the first vector with CD19- and CD20-binding domains linked to CD28 and z signaling domains. The second vector encodes a CD22 binding domain and the BB and z signaling domains and essentially recapitulated the signaling package of a third generation CAR vector (three different signaling domains) In the third Product, Example 3, the first vector encodes CD20- and CD22-binding domain linked to BB and z signaling domains and the second vector encodes a CD19-binding domain linked to CD28 and z signaling domains. In the fourth Product, Example 4, the first vector encodes CD20- and CD22-binding domains and BB and z signaling domains. The second vector encodes a CD19 binding domains and a z signaling domain.
Figure 2:
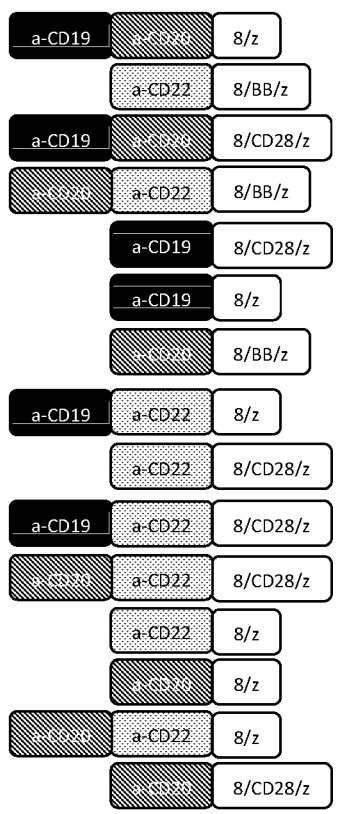
FIG. 2 depicts all potential single component that can be combined into DuoCAR sets for a therapeutic product targeting B cell malignancies. Nomenclature is identical to that in FIG. 1.
Figure 3:
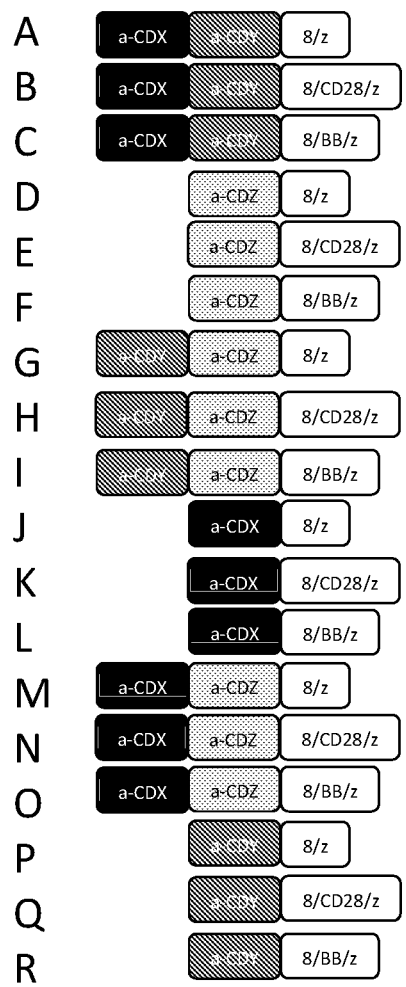
FIG. 3 depicts a generalized schema for DuoCAR sets that can be applied to multiple therapeutic needs, including inflammatory or autoimmune diseases and infectious diseases. In the Figure a-CDX, a-CDY, a-CDZ refer to antigen binding domains specific for three different target antigens, CDX, CDY, and CDZ, respectively. The intracellular aspect of the CARs all include the CD8 linker and transmembrane domain linked to either CD3-zeta, CD28, or 4-1BB signaling domains (as in FIG. 1). The specific combination of any of these two vectors (for example A plus F, wherein antigen X, Y, and Z would be targeted while providing intracellular signaling through CD3-zeta and 4-1BB) into a single vector will be defined according to the specific therapeutic need.
Figure 4:
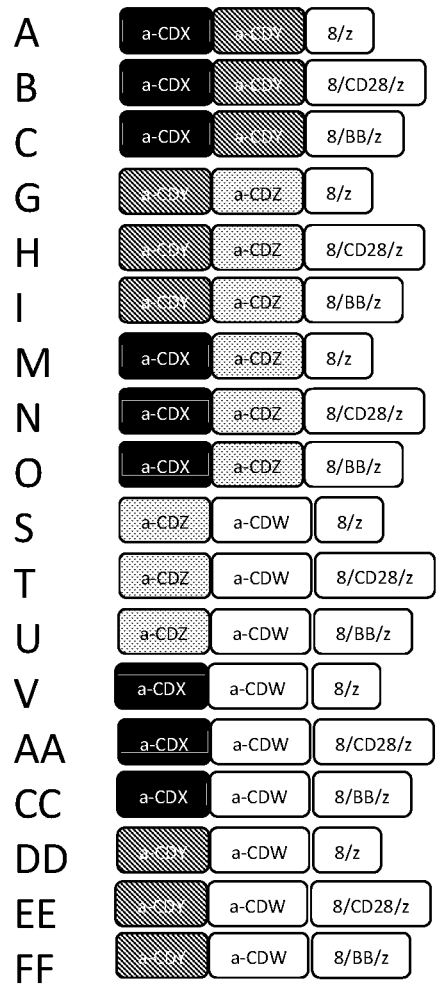
FIG. 4 depicts a generalized schema for DuoCAR sets in which two antigens are targeted by each vector. Vectors that are identical to those in FIG. 3 retain their specific letter designation (A in FIG. 3 and FIG. 4 are the same). The new, fourth, antigen binding domain is indicated by a-CDW. One product that would target 4 antigens be an A+T Duo CAR set. In this instance the extracellular antigens CDX, CDY, CDZ, and CDW would be targeted while providing both CD3-zeta and CD28 intracellular signals.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

The term "about" when referring to a measurable value such as an amount, a temporal duration, and the like, is meant to encompass variations of +/−20%, +/−10%, or more preferably +/−5%, or +/−1%, or still more preferably +/−0.1% from the specified value, as such variations are appropriate to perform the disclosed methods.

Unless otherwise noted, the technical terms herein are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

The present invention relates to compositions and methods for treating diseases and/or conditions, as well as cancers including, but not limited to, hematologic malignancies and solid tumors. The present invention relates to a patient-specific, tumor-specific strategy of adoptive cell transfer of T cells transduced with two or more vectors to express one or more DuoCARs.

The present invention relates more particularly to lentiviral vectors expressing chimeric antigen receptors (Duo-CARs), as well as host cells (e.g., lymphocytes, T cells) transduced with the lentiviral vectors expressing the CARS, nucleic acid molecules encoding the lentiviral vectors and chimeric antigen receptors, and methods of using same are also provided, for example, to treat a cancer in a subject.

Surprisingly and unexpectedly, it has now been discovered by the inventors that an immunotherapy composition comprising a patient-specific autologous anti-tumor lymphocyte cell population is much more effective as an anti-tumor immunotherapeutic if the autologous lymphocyte cell population is transduced with two or more lentiviral vectors encoding single or multiple chimeric antigen receptors (DuoCARs). The use of at least two or more lentiviral vectors expressing single or multiple CARS appears to promote in vivo expansion, persistence of patient-specific anti-tumor T-cells resulting in tumor stabilization, reduction, elimination, or remission of cancer, or prevention or amelioration of relapse of cancer, or any combination thereof, in a patient-specific manner.

Such active patient-specific anti-tumor T-cell populations as described herein can be infused directly back into the patient to promote in vivo expansion, persistence of patient-specific anti-tumor T-cells resulting in tumor stabilization, reduction, elimination, remission of cancer, or prevention or amelioration of relapse of cancer, or a combination thereof, in a patient-specific manner. This also includes effective expansion and rapid contraction of the therapeutic cell population.

Thus, in its broadest aspect, the novelty of this adoptive immunotherapy lies in the use of a combination of CAR-expression vectors. The differentiating feature is that contrary to the conventional use of a single vector expressing one or more chimeric antigen receptors, the Duo CAR approach confers both multiple antigen specificity and optimal signaling for anti-tumor T cell activity in vivo. Creating a system whereby three or more antigens are efficiently targeted is far superior to single or tandem approaches which allow for the tumor cancer cells to generate escape variants resulting in tumor metastasis and/or tumor relapse. The use of two or more vectors encoding single or multiple chimeric antigen receptors (DuoCARs) wherein the specific combination of least one binding domain(s) in each vector are non-identical coupled with the requirement that at least one signaling motif combination(s) are non-identical between each of the vectors, serves to ensure that genetically modified one or more lymphocyte populations transduced with such duo lentiviral vector-derived CARs generate a patient-specific autologous anti-tumor lymphocyte cell population capable of promoting in vivo expansion, persistence of patient-specific anti-tumor lymphocyte cells resulting in the stabilization, reduction, elimination, or remission of the tumor or cancer, and/or the prevention or amelioration of relapse of the tumor or cancer, or any combination thereof, in a patient-specific manner.

In one aspect, an immunotherapy composition is provided comprising one or more isolated nucleic acid molecules encoding at least two vectors (DuoCARs), each vector encoding a functional CAR, wherein at least one binding domain(s) in one of the vectors are non-identical, and whereby the combination of vectors results in the expression of two or more non-identical binding domains, wherein each vector encoded binding domain(s) are covalently linked to a transmembrane domain and one or more non-identical intracellular signaling motifs.

Figure 5:
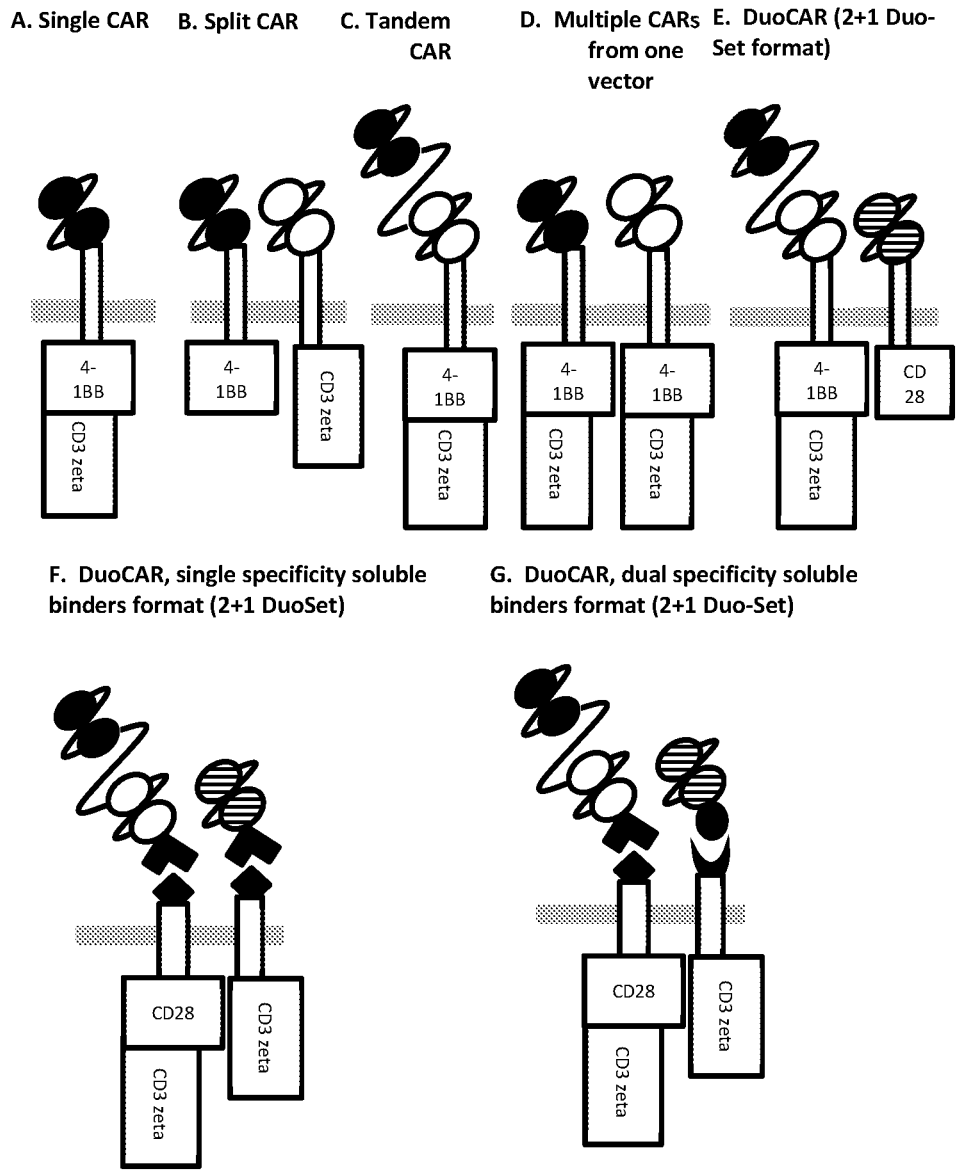
FIG. 5 depicts current CARs in the literature (A, B, C, D) in comparison to the DuoCARs of the present invention (E, F, G). CAR expression vectors can be created that induce expression of a single binding domain (paired black, open or striped spheres, each with separate specificities) connected to a linker and transmembrane domain (single open box). In the figure a thick gray line represents the plasma cell membrane. In this figure, the paired black spheres could represent anti-CD19 scFv, the paired open spheres represent anti-CD20 scFv and the paired striped spheres represent anti-CD22 scFv, all linked by joining amino acid sequences, for examples, multimers (1, 2, 3, 4, 5, or 6 repeats) of GGGGS. Intracellularly the lymphocyte signaling domains derived from 4-1BB (CD137), CD28, and the CD3-zeta chain can be combined as shown. (A) In Single CARs, a single binding domain is combined with a transmembrane and 2 signaling domains, created a second-generation CAR. (B) In Split CARs, two different binders are expressed with single signaling domains that must be combined to render effective T cell signaling upon recognition of two distinct antigens. (C) In Tandem CARS, two binding domains are linked to a single signaling domain. In this case binding of either domain induces full T cell activation. (D) In Multiple CARs from one vector, two fully functional CARs are expressed from a single vector, each able to bind only one antigen. (E) In contrast, DuoCARs are comprised of two vectors and express at least three binding domains, with multiple combinations of signaling domains possible. Essential features that differentiate the DuoCAR is the expression of two or more transcripts, the multiplicity of binding domains (at least one being multi-targeting), and the fully functional signaling characteristics of at least one of the two expressed cell surface proteins. (F) In a DuoCAR single-specificity soluble binder format, the CAR portion encoded by the vectors express a tag or an anti-tag motif that also encodes transmembrane and intracellular signaling motifs (CAR base vectors, non-identical with respect to intracellular motifs). The base vectors bind soluble proteins containing both the scFv domains that interact with antigen and a tag or anti-tag motif to mediate binding to the CAR base protein itself. Once the soluble proteins bind to the CAR base proteins, the same structural characteristics that mediate anti-tumor activity mediated by the DuoCAR [as in (E)] are reconstituted. (G) In a DuoCAR, dual-specificity soluble binder format, the dual specificity "tag"-"anti-tag" interactions are unique such that only one of the soluble binders can bind to only one of the base vectors. In this instance, the black diamond on the base vector and the angle-shaped binder on the soluble dual scFv protein may represent a "biotin"-"anti-biotin" interaction and the black crescent shape on the second CAR base vector interacts with the black oval on the single specificity scFv structure and may represent a "FITC"-"anti-FITC" interaction.

In another aspect, an immunotherapy composition is provided comprising one or more isolated nucleic acid molecules encoding at least two vectors (DuoCARs), each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, with the proviso that said immunotherapy composition specifically excludes the single CARs, the Split CARs, the Tandem CARs, or the Multiple CARs depicted in FIG. 5 (A), (B), (C), or (D), respectively.

The immunotherapeutic efficacy and prevention or amelioration of relapse of the tumor or cancer achieved with the Duo CAR Lentiviral vector-modified T cells of the present invention is significantly greater and synergistically more than that achieved with the singular conventional CAR design. It is this unique combination of biological therapeutic benefits that correlates with the increased in vivo expansion, persistence of patient-specific anti-tumor lymphocyte cells resulting in the stabilization, reduction, elimination, or remission of the tumor or cancer compared to conventional CAR-based T-cell immunotherapy.

CAR expression vectors can be created that induce expression of a single binding domain (black, open or striped spheres, each with separate specificities, FIG. 5) connected to a linker and transmembrane domain (single open box). FIG. 5, infra, depicts a comparison of the conventional CARs versus the DuoCARs of the present invention. In FIG. 5, a thick gray line represents the plasma cell membrane. Intracellularly the lymphocyte signaling domains derived from 4-1BB (CD137), CD28, and the CD3-zeta chain can be combined as shown. In all examples and uses of the CD3 signaling domain in this document, included are modifications of the CD3 zeta chain by the alteration of either one, two, or three of the immunoreceptor tyrosine-based activation motifs (ITAM) by selective mutagenesis of the tyrosine residue therein, or other such mutations that render that ITAM motif to no longer be a target for phosphorylation. In Single CARs (FIG. 5A), a single binding domain is combined with a transmembrane and 2 signaling domains. In Split CARs (FIG. 5B), two different binders are expressed with single signaling domains that must be combined to render effective signaling. In Tandem CARs (FIG. 5C), two binding domains are linked to a single signaling domain. In Multiple CARs from one vector (FIG. 5D), two fully functional CARs are expressed from a single vector. The Duo-CARs of the present invention (e.g., FIG. 5E) encode at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs. Essential features that differentiate the DuoCARs of the present invention is the use of two or more vectors, the multiplicity of binding domains, and the fully functional signaling characteristics (with regard to T cell expansion in vivo) of at least one of the two expressed cell surface proteins.

In another aspect, the DuoCARs are used to enhance the immune response to tumor mediated by the therapeutic T cell population. The immune response is enhanced in at least three ways.

Figure 6:
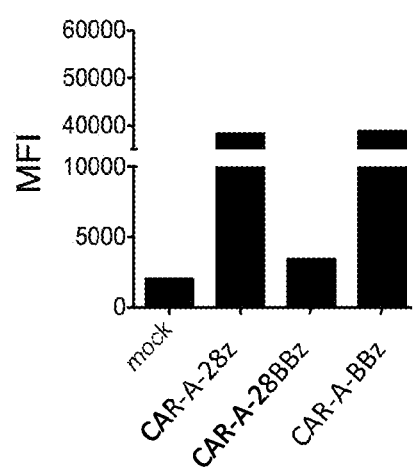
FIG. 6 depicts cell-surface expression levels of CAR constructs on primary human T cells transduced with CAR expression vectors that differ between second generation (two costimulatory domains) and third generation (three costimulatory domains) formats. T cells were transduced to express the following CARs: no CAR (mock), a second generation CAR (CAR-A-28z), a third generation CAR (CAR-A-28BBz), and an alternate second generation CAR (CAR-A-BBz). The level of surface expression of the CAR was detected by flow cytometry and is reported as mean fluorescence intensity (MF), y-axis. The MFI of both second generation CARs was much brighter, even though all construct expressed the very same CAR binding domain.

First, by providing the T cells an additional signal to expand and survive in the body, the DuoCARs of the present invention allow for the persistence of the therapeutic T cell population by virtue of stimulating the T cell population upon encountering self-antigen (for example CD19), whose loss can be tolerated by the patient, and yet which serves to provide a stimulatory signal for the therapeutic cellular population that does not reside in the tumor tissue itself. It is well known/established that third generation DuoCARs (expressing three co-stimulatory domains intracellularly, linked to a single extracellular Ig-like binder) are not expressed as well on therapeutic T cells compared to those DuoCARs expressing two intracellular co-stimulatory domains. For example, in FIG. 6 infra, the expression level of CAR constructs on primary human T cells differs between second generation (two costimulatory domains) and third generation (three costimulatory domains) constructs. T cells were transduced to express the following CARs: no CAR (mock), a second generation CAR (CAR-A-28z), a third generation CAR (CAR-A-28BBz), and an alternate second generation CAR (CAR-A-BBz). The level of surface expression of the CAR was detected by flow cytometry and is reported as mean fluorescence intensity (MF), y-axis. The MFI of both second-generation CARs was much brighter, even though all construct expressed the very same CAR binding domain.

By providing a third T cell activating sequence on a separate vector CAR construct, the inventors are able to regain the advantage of expressing three co-stimulatory domains, without incurring the disadvantage of the decreased expression of the CAR at the T cell surface.

In a second aspect, the DuoCARs of the present invention may target cell-types other than the tumor that mediate immunosuppressive effects. For example, if CD19-expressing B cells are present in the tumor lesion and also inhibit an anti-tumor immunity, as by the production of IL-4 or other mediators, the second benefit to the use of the DuoCAR-expressing tumor-specific T cell population is that the immunosuppressive cell population is also removed.

For example, if immunosuppressive B cells are present within a solid tumor lesion, these could be eliminated by the use of a B cell-specific DuoCAR (such as CD19-specific DuoCARs). If immunosuppressive fibroblast-like cells are present, these could be removed by stromal-specific DuoCARs (for example by targeting fibroblast activating protein-alpha (FAP)). If malformed vasculature is responsible for the lack of an efficacious immune response a DuoCAR specific for these types of vascular or lymph vessel specific targets (such as anti-VEGFR) may also improve therapeutic outcome.

In a third aspect, the DuoCARs of the present invention target an immunosuppressive population that is distal to the tumor, i.e. present in another compartment in the body. For example, using a DuoCAR to target myeloid derived suppressor cells (MDSCs), that may be present either in the tumor lesion itself or in the regional lymph nodes or bone marrow. It is well established that tumor-draining lymph nodes can either be loci of immune activation or immune suppression. This depends upon the overall inflammatory tone of the lymph node as well as distal dendritic cell differentiation prior to migration to the lymph node. If a tumor-draining lymph node is populated with myeloid-derived suppressor cells (MDSC) or miss-differentiated antigen presenting cells such as dendritic cells, a DuoCAR that targets these cell types, although distal to the tumor itself, may also improve therapeutic outcome. Beyond the cancer-specific DuoCAR immunotherapeutic applications, a second application of DuoCARs would be the prevention or treatment of autoimmune and/or inflammatory diseases. The difference from oncologic-based applications is that T-regulatory cells (Treg), or induced T-regulatory cells (iTreg), or other cells cultured in conditions that promote Th-2-like immune responses, would be the cellular substrate. For oncologic application Th-1 like cells are the cellular substrate. In therapeutic applications as diverse as graft-versus-host disease (GvHD) following hematopoietic stem cell transplantation (HSCT), allergic airway, gut, or other mucosal inflammation, or skin allergies, the presence of CAR-modified lymphocytes that produce immune-inhibitory cytokines, such as transforming growth factor-beta (TFG-beta), would serve to exert a broad tolerogenic signal that ameliorates the autoimmune- or inflammation-driven disease. This approach includes neurological inflammatory conditions of the periphery or central nervous system (CNS) such as Alzheimer's disease, multiple sclerosis, traumatic brain injury, Parkinson's disease, and CTE (chronic traumatic encephalopathy due to repeated concussions or microconcussions). This approach also includes progressive scarring diseases such as COPD (chronic obstructive pulmonary disease).

In the treatment of inflammatory diseases, lymphocytes specific for tissue antigens, distress markers on the surface of inflamed cells, or misfolded proteins (such as tau protein or beta-amyloid) would be created by generating DuoCAR expression vectors that are specific for these targets. Single antibody-based therapy for Alzheimer's is already in clinical development (i.e., Solanezumab by Eli Lilly and Company and Aducanumab by Biogen, Inc.). In Alzheimer's disease, antibody to monomeric or aggregated beta-amyloid could be used in a CAR format in lieu of binders to cell surface proteins. Binders to tau protein or tau-peptides bound by MHC molecules could also be used as binding motifs for CARS. Receptors that mediate the homing of lymphocytes to specific peripheral tissues can also be included in a CAR format, in order to render regional specificity to the CAR-expressing Treg population. Adhesion receptor domains known to drive lymphocyte infiltration into specific tissues and cytokine sequences or cytokine or chemokine receptors or binders could be used as part of the CAR domain. Adhesion molecules such as CD44 and integrin alpha-4 are known to target lymphocytes to the CNS, thus including domains from adhesion molecules know to mediate CNS migratory behavior of lymphocyte populations could also be used to target CAR-expressing lymphocytes to regions of disease. The same would hold true for the gut (i.e. binders to MAdCAm-1, expression of a CCR9, or anti-CCL25, etc.), lung (i.e. P-selectin or mesothelin), skin (i.e. binders to E-selectin), or other mucosal surfaces.

To use this approach, a patient with an inflammatory condition or whose disease could be treated by mitigation of inflammatory pathology, such as Alzheimer's disease, would be admitted to the clinic and peripheral blood harvested. Treg could be selected directly by immunomagnetic beads (Regulatory T cell isolation kit, Miltenyi Biotec), or induced by culture in the appropriate cytokine milieu. These Treg or iTreg would then be transduced with a DuoCAR vector and if required expanded in vitro (Treg expansion kit, Miltenyi Biotec). The DuoCAR binding domains would be derived from antibodies or receptors that mediate tissue specific homing and disease-associated binders, such as anti-beta amyloid. The engineered immune effector cells thus generated would be targeted to the appropriate site, and produce cytokines consistent with their Th2 or Treg differentiation pattern. It is also known that CAR-T cells can be engineered to secrete specific genetic payloads upon activation of the CAR receptor. In addition to the DuoCAR payload expressed from the vector, additional therapeutic proteins or peptides could be expressed or secreted by the engineered T cell populations such as: a) A-beta DPs (amyloid beta degrading proteases), b) matrix proteases (such as MMP-9 and MMP9 inhibitors in COPD), c) peptides or soluble antibody-like binders that interfere with plaque formation, and d) cytokines (such as TGF-beta, IL-4, IL-10).

MiRNAs could also be expressed within cells to modulate T cell function. Examples of miRNAs are miR-92a, miR-21, miR-155, miR-146a, miR-3162, miR-1202, miR-1246 and miR-4281, miR-142, miR-17-92. Also shRNAs to miRNAs could be developed. Examples are shRNAs targeted to miR-28, miR-150 and miR-107, which normally bind to PD1 and increase its expression.

Beyond oncology-based and inflammatory and autoimmune disease-based applications, a third application of the Duo CAR technology is the generation of therapeutic lymphocyte populations specific for viral, bacterial, or fungal antigens. Thus, as for oncology applications described for B cell malignancies, the targeting of infectious disease would allow the DuoCAR products to mediate immunoprotective or immunotherapeutic activity against the infective agents or the diseased tissues where they reside based upon recognition of microbial antigens. Unlike T cell receptor (TCR)-based approaches, where the T cell receptor itself mediates the recognition of pathogen encoded peptides, the Duo CAR approach would utilize binding proteins expressed in a CAR vector format that would give antibody-like recognition (that is, not requiring antigen processing) to the transduced T cell population. The activation of the therapeutic T cell population would result in an immune activating locus able to eliminate the infected cells, and if the microbial antigen is not cell associated, to release soluble mediators like interferon-gamma that would enable an effective immune response to be mounted against the infectious agent.

For example, HIV is known to be highly variable, and yet specific clades or families can be categorized and antibody to clade-specific viral envelope protein (env, gp120) created. Using the DuoCAR approach, three or more clade-specific antibody-like binders are included in the CAR constructs resulting in broad anti-HIV immune activity. In addition to viral proteins, bacterial protein can be targeted. A current medical challenge is the treatment of antibiotic resistant bacterial strains that often arise in healthcare settings. These include VRE (vancomycin resistant enterococci), MRSA (methicillin-resistant *Staphylococcus aureus*), KPC (*Klebsiella pneumoniae* carbapenemase producing gram-negative bacteria, also CRKP), and others. *Klebsiella* cell surface antigens include the O antigen (9 variants) and the K antigen (appx. 80 variants). The O antigen spectrum could readily be covered with a small DuoCAR library, as could a number of the K antigens. For use, CAR constructs would be created that feature antibodies that bind to different K or O serotypes, and these CAR vectors used to transduce a Th1-like effector cell population, isolated and activated as for oncology applications. In fungal diseases, the work of L. Cooper et al. (Kumasesan, P. R., 2014, PNAS USA, 111:10660) demonstrated that a fungal binding protein normally expressed on human cells, dectin-1, can be reconfigured as a CAR, and used to control fungal growth in vitro. The human disease aspergillosis occurs in severely immunosuppressed individuals and is caused by the fungus *A. fumigatus*. Multiple groups have produced monoclonal antibodies specific for the antigenic components of the *aspergillus* cell surface, thus opening the door to adoptive immunotherapy with DuoCARs that target three or more *aspergillus* antigens on the fungal surface. Thus, in all of these infectious disease applications, the ability to create immunoglobulin-like binders to microbial antigens allows a plurality of antigens to be targeted by CAR-expressing effector lymphocyte populations.

What follows is a detailed description of the DuoCARs that may be used in the patient-specific autologous anti-tumor lymphocyte cell population(s) disclosed herein, including a description of their extracellular domain, the transmembrane domain and the intracellular domain, along with additional description of the DuoCARs, antibodies and antigen binding fragments thereof, conjugates, nucleotides, expression, vectors, and host cells, methods of treatment, compositions, and kits employing the disclosed DuoCARs. While the compositions and methods of the present invention have been illustrated with reference to the generation and utilization of DuoCARs, it is contemplated herein that the compositions and methods are specifically intended to include the generation and utilization of TrioCARs and QuatroCARs.

A. Chimeric Antigen Receptors (as Present in DuoCARs)

The DuoCARs disclosed herein comprise at least two vectors, each vector encoding a functional CAR, whereby the combination of vectors results in the expression of two or more non-identical binding domains, wherein each vector encoded binding domain(s) are covalently linked to a transmembrane domain and one or more non-identical intracellular signaling motifs, at least one extracellular domain capable of binding to an antigen, at least one transmembrane domain, and at least one intracellular domain.

A CAR is an artificially constructed hybrid protein or polypeptide containing the antigen binding domains of an antibody (e.g., single chain variable fragment (scFv)) linked to T-cell signaling domains via a transmembrane domain. Characteristics of DuoCARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing DuoCARs the ability to recognize antigen independent of antigen processing, thus bypassing a major mechanism of tumor escape. Moreover, when expressed in T-cells, DuoCARs advantageously do not dimerize with endogenous T cell receptor (TCR) alpha and beta chains.

As disclosed herein, the intracellular T cell signaling domains of the DuoCARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen. In some instances the activation domains can be attenuated by the mutation of specific sites of phosphorylation, i.e. the ITAM motifs in the CD3 zeta chain, thus carefully modulating the degree of signal transduction mediated by that domain.

1. Extracellular Domain

In one embodiment, the CAR used in the patient-specific autologous anti-tumor lymphocyte cell population(s) as disclosed herein, comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens are well known in the art and include, for example, a glioma-associated antigen, carcinoembryonic antigen (CEA), beta-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I receptor, IGF-II receptor, IGF-I receptor and mesothelin. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20, CD22, and CD37 are other candidates for target antigens in B-cell lymphoma. Some of these antigens (CEA, HER-2, CD19, CD20, CD22, idiotype) have been used as targets for passive immunotherapy with monoclonal antibodies with limited success.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33, c-Met, PSMA, Glycolipid F77, EGFRvIII, GD-2, MY-ESO-1 TCR, MAGE A3 TCR, and the like. In yet another embodiment, a DuoCAR is provided herein comprising a Tag or anti-Tag binding domain.

Depending on the desired antigen to be targeted, the CAR can be engineered to include the appropriate antigen binding domain that is specific to the desired antigen target. For example, if CD19 is the desired antigen that is to be targeted, an antibody or the scFv subfragment thereof specific for CD19 can be used as the antigen bind domain incorporated into the CAR.

In one exemplary embodiment, the antigen binding domain portion of the CAR targets CD19. Preferably, the antigen binding domain in the CAR is anti-CD19 scFV, wherein the nucleic acid sequence of the anti-CD19 scFV comprises the sequence set forth in SEQ ID NO: 27. In one embodiment, the anti-CD19 scFV comprises the nucleic acid sequence that encodes the amino acid sequence of SEQ ID NO: 28. In another embodiment, the anti-CD19 scFV portion of the CAR comprises the amino acid sequence set forth in SEQ ID NO: 28. In a second exemplary embodiment, the antigen binding domain of the CAR targets CD20. Preferably, the antigen binding domains in the CAR is anti-CD20 scFv, wherein the nucleic acid sequence of the anti-CD20 scFv comprises the sequence set forth in SEQ ID NO: 1. In another embodiment, the anti-CD20 scFV portion of the CAR comprises the amino acid sequence set forth in SEQ ID NO: 2. In a third exemplary embodiment, the antigen binding domain of the CAR targets CD22. Preferably, the antigen binding domains in the CAR is anti-CD22 scFv, wherein the nucleic acid sequence of the anti-CD22 scFv comprises the sequence set forth in SEQ ID NO: 7. In another embodiment, the anti-CD22 scFV portion of the CAR comprises the amino acid sequence set forth in SEQ ID NO: 8.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus*, *Escherichia coli*, *Pseudomonas*, or *Salmonella*. Particularly, there is provided a CAR capable of binding to an antigen derived from an infectious bacterium, for example, *Helicobacter pyloris*, *Legionella* pneumophilia, a bacterial strain of Mycobacteria sps. (e.g. *M. tuberculosis*, *M. avium*, *M. intracellulare*, *M. kansaii*, or *M. gordonea*), *Staphylococcus aureus*, *Neisseria gonorrhoeae*, *Neisseria meningitides*, *Listeria monocytogenes*, *Streptococcus pyogenes*, Group A *Streptococcus*, Group B *Streptococcus* (*Streptococcus agalactiae*), *Streptococcus pneumoniae*, or *Clostridium tetani*, or a combination thereof 2. Transmembrane Domain In the DuoCARs used in the patient-specific autologous anti-tumor lymphocyte cell population(s) as disclosed herein, the CAR comprises one or more transmembrane domains fused to the extracellular domain of the CAR.

In one embodiment, an isolated nucleic acid molecule is provided wherein the encoded linker domain is derived from the extracellular domain of CD8, and is linked to the transmembrane domain.

In one embodiment, an isolated nucleic acid molecule is provided wherein the encoded linker domain is derived from the extracellular domain of the transmembrane domain and is linked to the transmembrane domain.

In some instances, the transmembrane domain can be selected or by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, CD271, TNFRSF19, Fc epsilon R, or any combination thereof. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet or a triple alanine motif provides a particularly suitable linker.

In one embodiment, the transmembrane domain in the CAR of the invention is the CD8 transmembrane domain. In one embodiment, the CD8 transmembrane domain comprises the nucleic acid sequence of SEQ ID NO: 11. In one embodiment, the CD8 transmembrane domain comprises the nucleic acid sequence that encodes the amino acid sequence of SEQ ID NO: 12. In another embodiment, the CD8 transmembrane domain comprises the amino acid sequence of SEQ ID NO: 12.

In some instances, the transmembrane domain of the CAR comprises the CD8.alpha.hinge domain. In one embodiment, the CD8 hinge domain comprises the nucleic acid sequence of SEQ ID NO: 13. In one embodiment, the CD8 hinge domain comprises the nucleic acid sequence that encodes the amino acid sequence of SEQ ID NO: 14. In another embodiment, the CD8 hinge domain comprises the amino acid sequence of SEQ ID NO: 14.

Without being intended to limit to any particular mechanism of action, it is believed that possible reasons for the enhanced therapeutic function associated with the exemplary DuoCARs used in the patient-specific autologous anti-tumor lymphocyte cell population(s) as disclosed herein include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

In one embodiment of the patient-specific autologous anti-tumor lymphocyte cell population(s) as disclosed herein, non-limiting exemplary transmembrane domains for use in the DuoCARs disclosed herein include the TNFRSF16 and TNFRSF19 transmembrane domains may be used to derive the TNFRSF transmembrane domains and/or linker or spacer domains as disclosed in Applicant's Provisional Patent Application No. 62/239,509, entitled CHIMERIC ANTIGEN RECEPTORS AND METHODS OF USE, as filed on Oct. 9, 2015, and assigned Lentigen Technology, Inc. matter number LEN_015PRO, including, in particular, those other TNFRSF members listed within the tumor necrosis factor receptor superfamily as listed in Table I therein.

3. Spacer Domain

In the DuoCARs used in the patient-specific autologous anti-tumor lymphocyte cell population(s) as disclosed herein, a spacer domain can be arranged between the extracellular domain and the TNFRSF transmembrane domain, or between the intracellular domain and the TNFRSF transmembrane domain. The spacer domain means any oligopeptide or polypeptide that serves to link the TNFRSF transmembrane domain with the extracellular domain and/or the TNFRSF transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 137 to 206 (SEQ ID NO: 15) which includes the hinge region of CD8.alpha. (NCBI RefSeq: NP.sub.—001759.3), amino acid numbers 135 to 195 of CD8.beta. (GenBank: AAA35664.1), amino acid numbers 315 to 396 of CD4 (NCBI RefSeq: NP.sub.—000607.1), or amino acid numbers 137 to 152 of CD28 (NCBI RefSeq: NP.sub.—006130.1) can be used. Also, as the spacer domain, a part of a constant region of an antibody H chain or L chain (CH1 region or CL region, for example, a peptide having an amino acid sequence shown in SEQ ID NO: 16) can be used. Further, the spacer domain may be an artificially synthesized sequence.

Further, in the CAR, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the nucleotide sequence of the leader (signal peptide) sequence shown in SEQ ID NO: 5. In one embodiment, the signal peptide comprises the amino acid sequence shown in SEQ ID NO: 6.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARS disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.—932170.1), amino acid numbers 45 to 86 of Fc.epsilon.RI.gamma. (NCBI RefSeq: NP.sub.—004097.1), amino acid numbers 201 to 244 of Fc.epsilon.RI.beta. (NCBI RefSeq: NP.sub.—000130.1), amino acid numbers 139 to 182 of CD3.gamma. (NCBI RefSeq: NP.sub.—000064.1), amino acid numbers 128 to 171 of CD3.delta. (NCBI RefSeq: NP.sub.—000723.1), amino acid numbers 153 to 207 of CD3.epsilon. (NCBI RefSeq: NP.sub.—000724.1), amino acid numbers 402 to 495 of CD5 (NCBI RefSeq: NP.sub.—055022.2), amino acid numbers 707 to 847 of 0022 (NCBI RefSeq: NP.sub.—001762.2), amino acid numbers 166 to 226 of CD79a (NCBI RefSeq: NP.sub.—001774.1), amino acid numbers 182 to 229 of CD79b (NCBI RefSeq: NP.sub.—000617.1), and amino acid numbers 177 to 252 of CD66d (NCBI RefSeq: NP.sub.—001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta. In another embodiment one, two, or three of the ITAM motifs in CD3 zeta are attenuated by mutation or substitution of the tyrosine residue by another amino acid.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.—001758.2), amino acid numbers 421 to 458 of CD4 (NCBI RefSeq: NP.sub.—000607.1), amino acid numbers 402 to 495 of CD5 (NCBI RefSeq: NP.sub.—055022.2), amino acid numbers 207 to 235 of CD8.alpha. (NCBI RefSeq: NP.sub.—001759.3), amino acid numbers 196 to 210 of CD83 (GenBank: AAA35664.1), amino acid numbers 181 to 220 of CD28 (NCBI RefSeq: NP.sub.—006130.1), amino acid numbers 214 to 255 of CD137 (4-1BB, NCBI RefSeq: NP.sub.—001552.2), amino acid numbers 241 to 277 of CD134 (OX40, NCBI RefSeq: NP.sub.—003318.1), and amino acid numbers 166 to 199 of ICOS (NCBI RefSeq: NP.sub.—036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 17 and the signaling domain of CD3-zeta comprises the nucleic acid sequence set forth in SEQ ID NO: 19.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 20.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 18 and the signaling domain of CD3-zeta comprises the amino acid sequence set forth in SEQ ID NO: 20.

5. Additional Description of DuoCARs

Also expressly included within the scope of the invention are functional portions of the DuoCARs used in the patient-specific autologous anti-tumor lymphocyte cell population (s) as disclosed herein. The term "functional portion" when used in reference to a CAR refers to any part or fragment of one or more of the DuoCARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the DuoCARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively, or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the DuoCARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The DuoCARs (including functional portions and functional variants) can be of any length, i.e., can comprise any number of amino acids, provided that the DuoCARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The DuoCARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, 5-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthyl alanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbornane)-carboxylic acid, γ-diaminobutyric acid, β-diaminopropionic acid, homophenylalanine, and a-tert-butylglycine.

The DuoCARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The DuoCARs (including functional portions and functional variants thereof) can be obtained by methods known in the art. The DuoCARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., Trends Biotechnol., 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) Blood, 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed CAR. In some embodiments, methods of using the chimeric antigen receptor include isolating T cells from a subject, transducing the T cells with an expression vector (such as a lentiviral vector) encoding the chimeric antigen receptor, and administering the CAR-expressing T cells to the subject for treatment, for example for treatment of a tumor in the subject.

B. Antibodies and Antigen Binding Fragments

One embodiment further provides a CAR used in the patient-specific autologous anti-tumor lymphocyte cell population(s) disclosed herein, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, scFv, dsFv or Fab. References to "VL" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273, 927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. scFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (scFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a scFv, is typically not decisive for scFvs. Thus, scFvs with both possible arrangements (VH-domain-linker domain-VL-domain; VL-domain-linker domain-VH-domain) may be used.

In a dsFv the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338, 929).

Also, a CAR, a T cell expressing a CAR, an antibody, or antigen binding portion thereof, can be to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

The DuoCARs used in the patient-specific autologous anti-tumor lymphocyte cell population(s) disclosed herein, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—NH₂) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, Ill. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,566, 7,498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.). Contemplated toxins also include variants of the toxins (see, for example, see, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87,1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

The CAR used in the patient-specific autologous antitumor lymphocyte cell population(s), a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the DuoCARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In one embodiment, an isolated nucleic acid molecule encoding a chimeric antigen receptor (DuoCARs) is provided comprising, from N-terminus to C-terminus, at least one extracellular antigen binding domain, at least one transmembrane domain, and at least one intracellular signaling domain.

In one embodiment of the CAR used in the patient-specific autologous anti-tumor lymphocyte cell population(s), an isolated nucleic acid molecule encoding the CAR is provided wherein the encoded extracellular antigen binding domain comprises at least one single chain variable fragment of an antibody that binds to the antigen.

In another embodiment of the CAR used in the patient-specific autologous anti-tumor lymphocyte cell population(s), an isolated nucleic acid molecule encoding the CAR is provided wherein the encoded extracellular antigen binding domain comprises at least one heavy chain variable region of an antibody that binds to the antigen.

In yet another embodiment of the CAR used in the patient-specific autologous anti-tumor lymphocyte cell population(s), an isolated nucleic acid molecule encoding the CAR is provided wherein the encoded CAR extracellular antigen binding domain comprises at least one lipocalin-based antigen binding antigen (anticalins) that binds to the antigen.

In one embodiment of the CAR used in the patient-specific autologous anti-tumor lymphocyte cell population(s), an isolated nucleic acid molecule is provided wherein the encoded extracellular antigen binding domain is connected to the transmembrane domain by a linker domain.

In another embodiment of the DuoCARs used in the patient-specific autologous anti-tumor lymphocyte cell population(s), an isolated nucleic acid molecule encoding the CAR is provided wherein the encoded extracellular antigen binding domain is preceded by a sequence encoding a leader or signal peptide.

In yet another embodiment of the DuoCARs used in the patient-specific autologous anti-tumor lymphocyte cell population(s), an isolated nucleic acid molecule encoding the CAR is provided wherein the encoded extracellular antigen binding domain targets an antigen that includes, but is not limited to, CD19, CD20, CD22, ROR1, mesothelin, CD33/IL3Ra, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments of the DuoCARs used in the patient-specific autologous anti-tumor lymphocyte cell population(s), an isolated nucleic acid molecule encoding the CAR is provided wherein the encoded extracellular antigen binding domain comprises an anti-CD19 scFV antigen binding domain, an anti-CD20 scFV antigen binding domain, an anti-CD22 scFV antigen binding domain, an anti-ROR1 scFV antigen binding domain, an anti-TSLPR scFV antigen binding domain, an anti-mesothelin scFV antigen binding domain, an anti-CD33/IL3Ra scFV antigen binding domain, an anti-CD38 scFV antigen binding domain, an anti-CD123 (IL3RA) scFV antigen binding domain, an anti-CD138 scFV antigen binding domain, an anti-BCMA (CD269) scFV antigen binding domain, an anti-GPC2 scFV antigen binding domain, an anti-GPC3 scFV antigen binding domain, an anti-FGFR4 scFV antigen binding domain, an anti-c-Met scFV antigen binding domain, an anti-PMSA scFV antigen binding domain, an anti-glycolipid F77 scFV antigen binding domain, an anti-EGFRvIII scFV antigen binding domain, an anti-GD-2 scFV antigen binding domain, an anti-NY-ESo-1 TCR scFV antigen binding domain, an anti-MAGE A3 TCR scFV antigen binding domain, or an amino acid sequence with 85%, 90%, 95%, 96%, 97%, 98% or 99% identity thereof, or any combination thereof.

In one aspect of the DuoCARs used in the patient-specific autologous anti-tumor lymphocyte cell population(s), the DuoCARs provided herein further comprise a linker domain.

In one embodiment of the DuoCARs used in the patient-specific autologous anti-tumor lymphocyte cell population(s), an isolated nucleic acid molecule encoding the CAR is provided wherein the extracellular antigen binding domain, the intracellular signaling domain, or both are connected to the transmembrane domain by a linker domain.

In one embodiment of the DuoCARs used in the patient-specific autologous anti-tumor lymphocyte cell population(s), an isolated nucleic acid molecule encoding the CAR is provided wherein the encoded linker domain is derived from the extracellular domain of CD8, and is linked to the transmembrane domain.

In yet another embodiment of the DuoCARs used in the patient-specific autologous anti-tumor lymphocyte cell population(s), an isolated nucleic acid molecule encoding the CAR is provided wherein the nucleic acid sequence encoding the transmembrane domain comprises a nucleotide sequence with 85%, 90%, 95%, 96%, 97%, 98% or 99% identity thereof.

In one embodiment of the DuoCARs used in the patient-specific autologous anti-tumor lymphocyte cell population(s), an isolated nucleic acid molecule encoding the CAR is provided wherein the encoded transmembrane domain comprises an amino acid sequence comprising at least one but not more than 10 modifications, or a sequence with 85%, 90%, 95%, 96%, 97%, 98% or 99% identity thereof.

In another embodiment of the DuoCARs used in the patient-specific autologous anti-tumor lymphocyte cell population(s), an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment of the DuoCARs used in the patient-specific autologous anti-tumor lymphocyte cell population(s), an isolated nucleic acid molecule encoding the CAR is provided wherein the encoded intracellular signaling domain further comprises a CD3 zeta intracellular domain.

In one embodiment of the CAR disclosed herein, an isolated nucleic acid molecule encoding the CAR is provided wherein the encoded intracellular signaling domain is arranged on a C-terminal side relative to the CD3 zeta intracellular domain.

In another embodiment of the DuoCARs used in the patient-specific autologous anti-tumor lymphocyte cell population(s), an isolated nucleic acid molecule encoding the CAR is provided wherein the encoded at least one intracellular signaling domain comprises a costimulatory domain, a primary signaling domain, or a combination thereof.

In further embodiments of the DuoCARs used in the patient-specific autologous anti-tumor lymphocyte cell population(s), an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment of the DuoCARs used in the patient-specific autologous anti-tumor lymphocyte cell population(s), an isolated nucleic acid molecule encoding the CAR is provided that further contains a leader sequence or signal peptide sequence.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the DuoCARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa, USA).

The nucleic acid can comprise any isolated or purified nucleotide sequence which encodes any of the DuoCARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions.

By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive DuoCARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.).

Bacteriophage vectors, such as λü TIO, λüTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2µ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4+/CD8+ double positive T cells, CD4+ helper T cells, e.g., Thi and Th2 cells, CD8+ T cells (e.g., cytotoxic T cells), tumor infiltrating cells, memory T cells, naive T cells, and the like. The T cell may be a CD8+ T cell or a CD4+ T cell.

In an embodiment, the DuoCARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

DuoCARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the DuoCARs used in the patient-specific autologous anti-tumor lymphocyte cell population(s) can be used in methods of treating or preventing a disease in a mammal. In this regard, an embodiment provides a method of treating or preventing cancer in a mammal, comprising administering to the mammal the DuoCARs, the nucleic acids, the recombinant expression vectors, the host cells, the population of cells, the antibodies and/or the antigen binding portions thereof, and/or the pharmaceutical compositions in an amount effective to treat or prevent cancer in the mammal. Additional methods of use of the aforementioned DuoCARs have been disclosed supra.

An embodiment further comprises lymphodepleting the mammal prior to administering the DuoCARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia (CLL), hairy cell leukemia, acute lymphocytic leukemia (ALL), acute myeloid leukemia (AML), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the DuoCARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the Duo-CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor α (TNF-a) or interleukin 2 (IL-2)). In addition, CAR function can be evaluated by measurement of cellular cytotoxicity, as described in Zhao et al, J. Immunol. 174: 4415-4423 (2005).

Another embodiment provides for the use of the Duo-CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a non-toxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, DuoCARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR– T cells, antibodies, antigen binding fragment, or conjugates disclosed herein. Methods and therapeutic dosages of such agents are known to those skilled in the art, and can be determined by a skilled clinician.

Additional chemotherapeutic agents for combination immunotherapy include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun 73:316-321, 1991; Bierer et al., Curr. Opin. Immun 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy, adoptive immunotherapy, and/or cell therapy that include one or more of the disclosed DuoCARs, or T cells expressing a CAR, antibodies, antigen binding fragments, conjugates, DuoCARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed DuoCARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington Pharmaceutical Science*, 19th ed., Mack Publishing Company, Easton, Pa. (1995).

A CAR, or T cell expressing a CAR, antibodies, antigen binding fragments, or conjugates may be provided in lyophilized form and rehydrated with sterile water before administration, although they are also provided in sterile solutions of known concentration. The DuoCARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the DuoCARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, Kits employing the DuoCARs disclosed herein are also provided. For example, kits for treating a tumor in a subject, or making a CAR T cell that expresses one or more of the DuoCARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, DuoCARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, DuoCARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, DuoCARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the examples of the DuoCARs depicted within the accompanying Figures infra and the disclosure at pages 17-27, inclusive supra, which examples are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

Two examples are provided whereby the expression of three functional binding domains on the surface of a LV-transduced human T cell population proves the feasibility of the DuoSet technology (Example 1), and the functional activity of this population against three different leukemia antigens proves its effectiveness (Example 2).

Examples of the single specificity CARs on which this technology is based and which may be included as a DuoSet component in a DuoCAR include the single CD20 targeting vector LTG1495, nucleotide sequence SEQ ID NO: 3 and amino acid sequence SEQ ID NO: 4. A second example is the single specificity CAR LTG2200, specific for CD22, nucleotide sequence SEQ ID NO: 9 and amino acid sequence SEQ ID NO: 10. An important molecular aspect in creating DuoCARs is the inclusion of non-redundant compatible sequences, and the evaluation of those sequence in transduced T cells such that no untoward recombination or intracellular association occurs. This can occur both in the producer cell line of the vector, or in the target cell population. For this reason, we include variant CAR structures that are known to be compatible in the DuoCAR setting. These include the CD19-specific CAR LTG1494 described in nucleotide sequence SEQ ID: 29 and amino acid sequence SEQ ID: 30, respectively. This sequence includes the well-described linker that joins the heavy and light chains of the scFv referred to as the Whitlow linker (amino acid sequence GSTSGSGKPGSGEGSTKG (SEQ ID NO: 53), see Whitlow M., et al., 1993, Protein Eng. 6:989-995). In some cases the Whitlow linker was substituted for a (GGGGS)$_n$ linker, for example in a CD19 CAR format, as in LTG1538, nucleotide sequence SEQ ID NO: 31 and amino acid sequence SEQ ID NO: 32, respectively. In another example CARS were created that have alternate transmembrane domains. The anti-CD19 CAR LTG1562, nucleotide sequence SEQ ID NO: 21 and amino acid sequence SEQ ID NO: 22, respectively, utilizes the CD4 (as opposed to CD8) transmembrane domain. Similarly the anti-CD19 CAR LTG1563 has an alternate transmembrane derived from TNFRSF19, nucleotide sequence SEQ ID NO: 49 and amino acid sequence SEQ ID NO:50, respectively. DuoCARs can also be targeted to solid tumors, for example those expressing the mesothelin tumor antigen. For example, scFV binders have been created for mesothelin, as disclosed in Applicant's Provisional Patent Application No. 62/444,201, entitled Compositions and Methods for Treating Cancer with Anti-Mesothelin Immunotherapy, as filed on Jan. 9, 2017, and assigned Lentigen Technology, Inc. matter number LEN 017, nucleotide sequence SEQ ID NO: 37 and amino acid sequence SEQ ID NO: 38, respectively, that can be incorporated into functional CARs, nucleotide sequence SEQ ID NO: 39 and amino acid sequence SEQ ID NO: 40, respectively, and that can thereby be incorporated into a DuoCAR therapy. In addition to scFv sequences, single chain antigen binders (as opposed to scFv) can be incorporated into a DuoCAR application. For example, the CD33-specific heavy chain only binder, as disclosed in Applicant's Provisional Patent Application No. 62/476,438, entitled Compositions and Methods For Treating Cancer With Anti-CD33 Immunotherapy, as filed on Mar. 24, 2017, and assigned Lentigen Technology, Inc. matter number LEN 018, nucleotide sequence SEQ ID NO: 41 and amino acid sequence SEQ ID NO: 42, respectively, can be incorporated into a functional CAR, LTG1906, nucleotide sequence SEQ ID NO: 43 and amino acid sequence SEQ ID NO: 44, respectively, that targets CD33-expressing malignancies. One example of a DuoCAR therapeutic application would be the treatment of leukemia that expresses the CD19, CD20, and TSLPR antigens. In this case, LTG1496 or LTG 1497 (SEQ ID NOs: 35, 26, respectively) could be combined with a TSLPR-specific CAR (LTG1789), SEQ ID NO: 47 and amino acid sequence SEQ ID NO: 48, respectively, that had been created from TSLPR-specific scFV domains, nucleotide sequence SEQ ID NO: 45 and amino acid sequence SEQ ID NO: 46.

Examples of tandem-CARs (containing 2 scFv domains, as described in nucleotide sequence SEQ ID: 23 and amino acid sequence SEQ ID:24) on which this technology is based include the CD20_CD19 CAR LTG1497, nucleotide sequence SEQ ID NO: 25 and amino acid sequence SEQ ID NO: 26. In some cases reversing the order of the two binders may provide a better DuoCAR expression in target cells. Thus, LTG1497, where the CD19 scFV is more proximal, as shown in nucleotide sequence SEQ ID NO: 25 and amino acid sequence SEQ ID NO: 26; and LTG1496 where the CD19 scFV is more distal to the membrane, as shown in nucleotide sequence SEQ ID NO: 33 and amino acid sequence SEQ ID NO: 34, can both be used as one of the members of a DuoSet comprising a DuoCAR.

Methods Utilized in Examples 1 and 2:

Cell Lines (PBMC and Targets)

All cell lines and reagents were purchased from American Tissue Culture Collection (ATCC, Manassas, Va.), unless otherwise noted. The Burkitt lymphoma cell line Raji, the acute lymphocytic leukemia cell lines REH, as well as the chronic myelogenous leukemia cell line K562, were cultured in RPMI-1640 medium supplemented with 10% heat-inactivated fetal bovine serum (FBS, Hyclone, Logan, Utah) and 2 mM L-Glutamax (Thermo Fisher Scientific, Grand Island, N.Y.). The human embryonic kidney cell line 293T was propagated in Dulbecco's modified Eagle medium supplemented with 10% heat-inactivated FBS.

Single-cell clones of luciferase-expressing cell lines were generated by stably transducing wild-type tumor lines with lentiviral vector encoding firefly luciferase (Lentigen Technology, Inc., Gaithersburg, Md.), followed by cloning and selection of luciferase-positive clones. The mouse-adapted Raji-luc line was generated by engrafting a Raji clone stably expressing firefly luciferase into NSG mice (NOD.Cg-Prkdcscid Il2rgtm1Wjl/SzJ), The Jackson Laboratory Sacramento, Calif.), isolating the engrafted Raji-luc tumor cells from mouse spleens by either positive (CD19 microBeads, human, Miltenyi Biotec, Bergisch Gladbach, Germany) or negative selection (mouse cell depletion kit, Miltenyi Biotec), expanding in culture, and re-cloning to facilitate the selection of clones with high expression of firefly luciferase. Whole blood was collected from healthy volunteers at Oklahoma Blood Institute (OBI, Oklahoma City, Okla.) with donors' written consent. Processed buffy coats were purchased from OBI. The CD4-positive and CD8-positive human T cells were purified from buffy coats via positive selection using a 1:1 mixture of CD4- and CD8-MicroBeads (Miltenyi Biotec) according to manufacturer's protocol.

Creation of Chimeric Antigen Receptor (CAR)—Expressing Vectors Comprising DuoSets CAR antigen-binding domains, scFv, sequences were derived from the mouse hybridoma FMC-63 for CD19 (FMC-63: AA 1-267, GenBank ID: HM852952.1) and Leu-16 for CD20 [1], entire sequence of VL and VH. The CD22 scFv binding was created from publicly available sequences. Tandem CAR19_20 or CAR20_19 were generated by linking scFv of each antibody in frame to CD8 hinge and transmembrane domains (AA 123-191, Ref sequence ID NP 001759.3), 4-1BB (CD137, AA 214-255, UniProt sequence ID Q07011) transactivation domain and CD3 zeta signaling domain (CD247, AA 52-163, Ref sequence ID: NP_000725.1.). The scFv regions of 19A and 20A were linked in sequence by a flexible interchain linker $(GGGGS)_5$ (SEQ ID NO: 54), followed by CD8, 4-1BB and CD3 zeta domains. Leader sequence from human granulocyte macrophage colony stimulating factor receptor alpha subunit was included in all constructs, as described in [2]. CAR constructs sequences were codon optimized (DNA2.0, Newark, Calif.) and cloned into a third generation lentiviral plasmid backbone (Lentigen Technology Inc., Gaithersburg, Md.) under the regulation of a human EF-1α promoter. Lentiviral vector (LV) containing supernatants were generated by transient transfection of HEK 293T cells, as previously described [3]. Harvested pelleted lentiviral supernatants were stored at −80° C.

Primary T Cell Transduction:

Selected CD4+ and CD8+ human primary T cells from normal donors were cultivated in TexMACS medium (serum-free) supplemented with 40 IU/ml IL-2 at a density of 0.3 to $2\times10^6$ cells/ml, activated with CD3/CD28 MACS® GMP TransAct reagent (Miltenyi Biotec) and transduced on day 3 with lentiviral vectors encoding CAR constructs in the presence of 10 ug/ml protamine sulfate (Sigma-Aldrich, St. Louis, Mo.) overnight, and media exchanged on day 4. On day 5, cultures were transferred to TexMACS medium supplemented with 200 IU/ml IL-2, and propagated until harvest on day 10-13.

Immune Effector Assays:

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison Wis.) was added to each well and the resulting luminescence was analyzed on an EnSpire plate reader (Perkin Elmer, Shelton, Conn.) and recorded as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)).

Flow Cytometric Analysis:

All cell staining reagents for flow cytometry were from Miltenyi Biotec, unless otherwise noted. One million CAR T transduced cells were harvested from culture, washed two times in cold staining buffer (AutoMACS solution with 0.5% bovine serum albumin) and pelleted at 350×g for 5 minutes at 4° C. CAR surface expression on transduced T cells was initially detected by staining with protein L-biotin conjugate (stock 1 mg/ml, 1:1000 dilution, GenScript, Piscataway, N.J.) for 30 minutes at 4° C., followed by two washes and staining with streptavidin-PE conjugate for 30 minutes at 4° C. (stock: 1.0 ml, 1:200 dilution, Jackson ImmunoResearch Laboratories, West Grove, Pa.). Non-transduced cells and transduced cells stained with streptavidin-PE only, were used as negative controls. Anti-CD4 antibody was employed to determine CD4 to CD8 ratio of CART positive population, and was added during the second incubation step. Dead cells were excluded by 7AAD staining (BD Biosciences, San Jose, Calif.). Cells were washed twice and resuspended in 200 ul Staining Buffer before quantitative analysis by flow cytometry. Specific DuoSet CAR T staining was carried out on Human T cells activated with CD3-CD28 nanomatrix (TransAct, Miltenyi Biotec) transduced with DuoSet vectors in the presence of IL-2, and analyzed for expression of CD19-, CD20-, or CD22-scFv domains by flow cytometry using recombinant CD19, CD20, or CD22 for staining, as for antibodies.

Anti-CD19 scFv activity was detected with CD19-Fc (R&D Biosystems), used at 1 ug/sample, and stained with goat anti-human Fc-gamma-R-PE (Jackson ImmuoResearch Laboratories, Inc.) at 0.75 ug/sample. Anti-CD20 scFv activity was detected with CD20-biotin (Miltenyi Biotech), 0.1 ug/sample, detected with streptavidinpAPC (Miltenyi Biotec) at 0.2 ug/sample. Anti-CD22 scFc activity was detected with CD22-His (Thermo Fisher) at 0.1 ug/sample, and detected with anti-His FITC (Miltenyi Biotec). Flow cytometric analysis was performed on a MACSQuant® 10 Analyzer (Miltenyi Biotec). Characterization of target tumor lines and luciferase-positive sub clones was performed using CD19-FITC, CD20 VioBlue, and CD22-APC antibodies. Dead cells were excluded from analysis by 7AAD staining (BD Biosciences, San Jose, Calif.).

Example 1

Expression of a DuoCAR (2+1 DuoSet) on Primary Human T Cells

Figure 7:
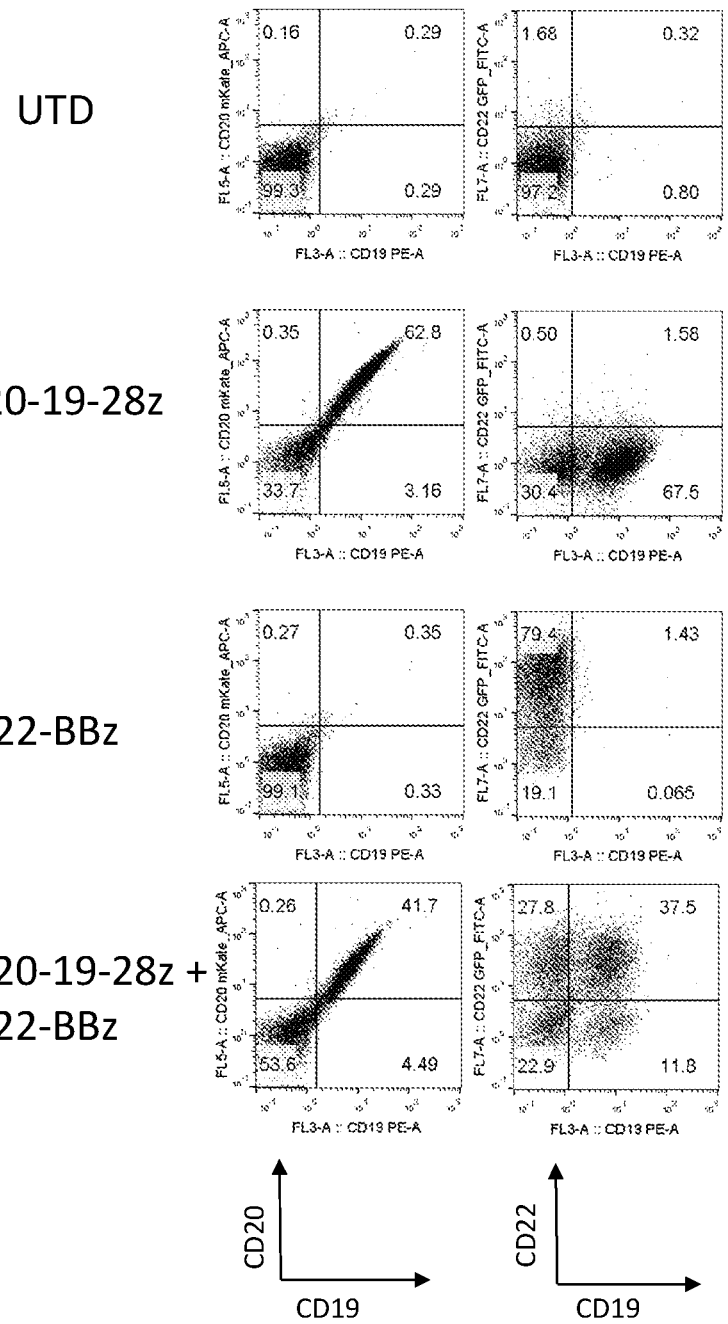
FIG. 7 depicts DuoCAR cell surface expression in human T cells. Human T cells were activated with CD3-CD28 nanomatrix (TransAct, Miltenyi Biotec) in the presence of IL-2, transduced with two vectors (one encoding a tandem CD20-CD19 CAR and one encoding a single CD22 CAR, thus a 2+1 Duo-Set format), and then analyzed for expression of CD19-, CD20-, or CD22-scFv domains by flow cytometry using recombinant CD19, CD20, or CD22 for staining. The paired columns show dual staining for CD20 and CD19 scFvs, left column, and CD22 and CD19 scFvs, right column. Row 1 shows T cells that were not transduced (UTD) and thus show no binding. Row 2 shows T cells transduced with LV encoding a CD20_CD19 CAR vector with a CD8 transmembrane and intracellular CD28 and CD3-zeta signaling domains (20-19-28z). While dual staining is seen for CD20 and CD19 binding (left panel), only CD19 binding is seen in the right panel. Row 3 shows T cells transduced with a CD22 CAR vector with a CD8 transmembrane and intracellular 4-1BB and CD3-zeta signaling domains (22-BBz). No dual staining is seen with CD19 or CD20 (left panel) and only a single population of cells able to bind CD22 is seen (right panel). In Row 4 T cells are transduced with a DuoSet comprised of both vectors in Row 2 and Row 3. Only the DuoSet express all three CAR-encoded binding domains (42% of the cells express CD20_19 (left panel), and 38% expresses CD22 and CD19 binding domains (right panel). As CD22 and CD19 scFv are on each of the two separate transmembrane proteins comprising the DuoSet, 38% represents the true DuoSet expressing population in this example.

As a proof of principle, a DuoSet comprised of two CAR-T vectors was created. One member of the set expressed a tandem CD20_CD19 binding domain linked to CD8 transmembrane and CD28 and CD3-zeta signaling domains (LTG2228), SEQ ID NO: 51 and SEQ ID NO: 52. The second member of the DuoSet was a CAR construct with a single CD22 binder linked to CD8 transmembrane and 4-1BB and CD3-zeta signaling domains (LTG2200), SEQ ID NO: 9 and SED ID NO: 10. In FIG. 7, the paired columns show dual staining for CD20 and CD19 scFvs, left column, and CD22 and CD19 scFvs, right column. Row 1 shows T cells that were not transduced (UTD) and thus show no binding. Row 2 shows T cells transduced with LV encoding a CD20_CD19 CAR vector with a CD8 transmembrane and intracellular CD28 and CD3-zeta signaling domains (20-19-28z). While dual staining is seen for CD20 and CD19 binding (left panel), only CD19 binding is seen in the right panel. Row 3 shows T cells transduced with a CD22 CAR vector with a CD8 transmembrane and intracellular 4-1BB and CD3-zeta signaling domains (22-BBz). No dual staining is seen with CD19 or CD20 (left panel) and only a single population of cells able to bind CD22 is seen (right panel). In Row 4 T cells are transduced with a DuoSet comprised of both vectors in Row 2 and Row 3. Only the DuoSet express all three CAR-encoded binding domains (42% of the cells express CD20_19 (left panel), and 38% expresses CD22 and CD19 bonding domains (right panel). As CD22 and CD19 scFv are on each of the two separate

Example 2

Anti-Leukemia Activity of a Human T Cell Preparation Expressing a DuoCAR

Figure 8:
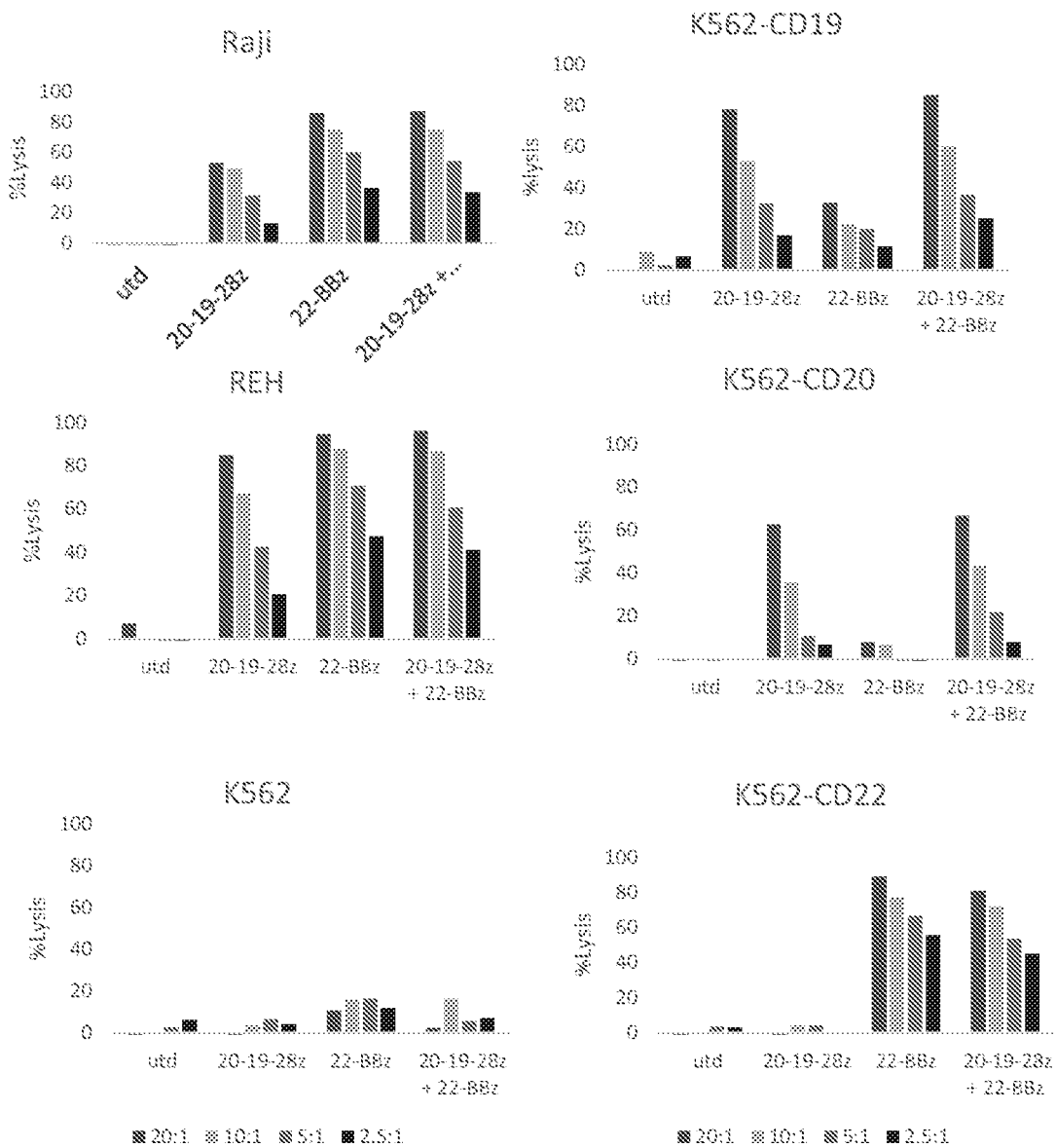
FIG. 8 depicts the anti-tumor cytolytic activity of Duo-CAR expressing T cells. Human T cells transduced with single CAR components (20_19-28z or 22-BBz) or DuoSets (20_19-28z+22-BBz), as described in FIG. 7, were used in cytotoxic T cells assay at four different effector to target ratios (20:1, 10:1, 5:1, 2.5:1, as indicated). The leukemia cell lines used as CAR-T targets were: Raji (expresses all three target antigens), REH (expresses all three target antigens), K562 (control, no targets expressed), K562-CD19 (expresses CD19), K562-CD20 (expresses CD20), and K562-CD22 (expresses CD22). Only the DuoCAR-transduced cells (20-19-28z+22-BBz, 2+1 DuoSet) exhibited high cytolytic activity against both leukemia cell lines (Raji and REH), and all three single-expressing K562 target cells lines (K562-CD19, K562-CD20, K562-CD22).

Anti-leukemia activity of a human T cell preparation expressing a DuoCAR that targets three leukemia antigens simultaneously (c.f., see FIG. 7 for DuoCAR expression characteristics). A DuoSet comprised of a CD20_19 tandem CAR and a CD22-specific single CAR (prepared as in Example 1) was used an effector T cell population in a cytotoxic T cell assay using leukemia cell line and model cell lines as targets. Human T cells transduced with single CAR components (20_19-28z or 22-BBz) or DuoSets (20_19-28z+22-BBz), were used in cytotoxic T cells assay at four different effector to target ratios (20:1, 10:1, 5:1, 2.5:1, as indicated) (c.f., see FIG. 8). The leukemia cell lines used as CAR-T targets were: Raji (expresses all three target antigens), REH (expresses all three target antigens), K562 (control, no targets expressed), K562-CD19 (expresses CD19), K562-CD20 (expresses CD20), and K562-CD22 (expresses CD22). Only the DuoCAR-transduced cells (20-19-28z+22-BBz) exhibited high cytolytic activity against both leukemia cell lines (Raji and REH), and all three single-expressing K562 target cells lines (K562-CD19, K562-CD20, K562-CD22). This demonstrates that the DuoCAR technology can uniquely target three leukemia antigens simultaneously, in the same effector T cell population, and thus demonstrates superior anti-neoplastic activity by being able to target more than one or two target antigens at a time, thus decreasing the possibility of the malignancy generating escape mutants (cells clones that have lost or down-modulate one or two antigens and this escaped immune-ablation. The end result will be higher cure rates for patients, due to escape and outgrowth of antigen-loss variants, which in the end is a relapse.

Example 3

DuoCAR Production Methods

Figure 9:
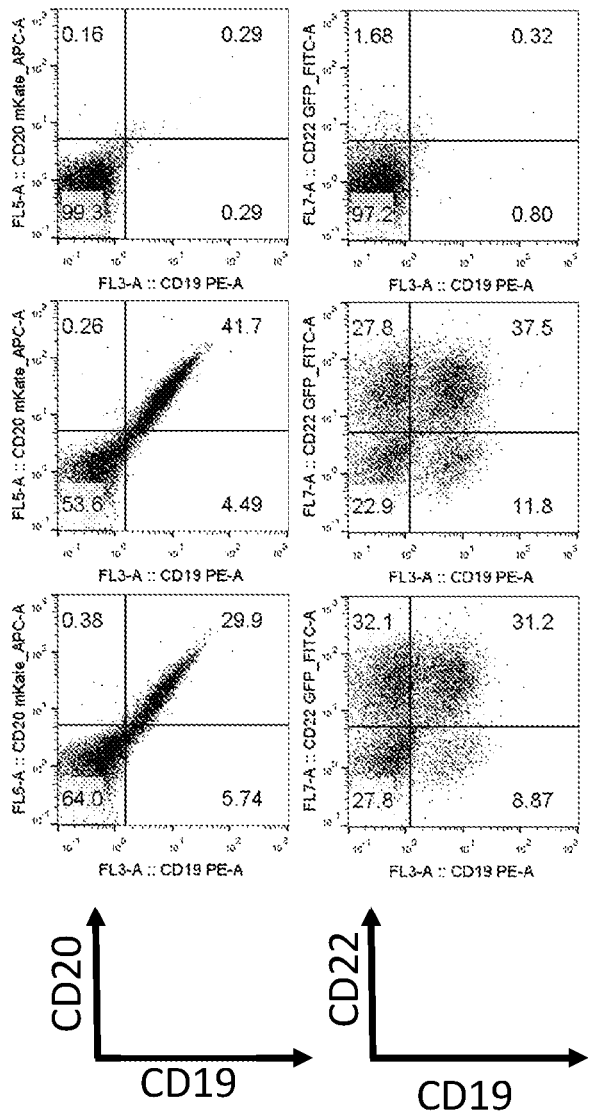
FIG. 9 depicts DuoCAR cell surface expression in primary human T cells, as achieved by two different methods of LV preparation. The same methods and data analyses were used as in FIG. 7, thus cells transduced with a DuoCAR specific for CD19, CD20, and CD22 (a 2+1 DuoSet where one CAR is a tandem CD20 and CD19 binder and the second CAR is comprised of a CD22 binder) were created. The first column of data shows flow cytometric analysis for the expression of CD19 and CD20 binders, whereas the second column shows flow cytometric analysis for CD22 and CD19 binders present as CARs in DuoCAR expressing cells for four distinct populations corresponding to the non-transduced, the singly CD22-CAR transduced, the dually transduced with CD22 and CD20_19 CARS, and singly transduced with the tandem CD20_CD19 CAR in the lower left, upper left, upper right, and lower right quadrants, respectively. Both the two LV transduction method (co-transduction) and the single LV transduction method (co-transfection) gave a similar DuoCAR staining pattern, where more than 30% of the T cell population was specific for CD19, CD20, and CD22, by virtue of expressing both CAR cell surface proteins.

The DuoCAR technology described in this application generates a population of therapeutic lymphocytes, in this example human T cells, that express more than two antigen specificities from more than one transmembrane protein encoded by a gene vector. In this example, this is achieved by two different means. FIG. 9 contains three rows of data, labeled "un-transduced," "co-transduction," and "co-transfection." FIG. 9 contains two columns of data, generated as in FIG. 7, wherein the first column is analyzed by flow cytometry for the expression of CD20- and CD19-specific specific binding, and the second column is analyzed by flow cytometry for the expression of CD22- and CD19-binding activity. In the first row of data, un-transduced human T cells are shown. No binding activity is exhibited for the CD19, CD20, or CD22 recombinant protein indicators of CAR-derived binding activity, demonstrating no DuoCAR expression. In the second row, "co-transduction" was used to generate DuoCARs. In this data set, two LV were used to simultaneously transduce activated T cells. As in FIG. 7, one CAR in the DuoSet comprising the DuoCAR was a tandem CD20 and CD19 binder linked to CD28 signaling and CD3-zeta signaling motifs; and the other CAR was a CD22 binder, linked to 4-1BB and CD3-zeta signaling motifs. The second quadrant (Q2) in column one shows a very specific pattern of unitary staining for CD20 and CD19-scFv activity. This is due to both binders being on the same surface glycoprotein, and thus they are co-expressed with equal intensity, generating the very specific linear pattern seen. In the second column of the co-transduction data, a more traditional pattern is seen when the two glycoproteins are not expressed in a uniform pattern on each cell. Thus a pattern of 4 distinct populations is seen. In the lower left quadrant, cells expressing neither binder are seen. In the upper left, cells expressing only the CD22 CAR are seen. In the lower right quadrant cells expressing only the CD20_CD19 tandem CAR are seen. Finally, in the upper right quadrant cells expressing both members of the CAR DuoSet, comprising the DuoCAR, are seen.

In the bottom row, cell populations expressing the DuoCAR are generated in a different manner. Unlike the co-transduction method, where 2 LV preparations created independently are used at the time of the T cell transduction, "co-transfection" refers to a method wherein two backbone plasmids (encoding the two CARs comprising the DuoCAR) are transfected into the 293T cells generating LV at the same time. The other plasmids comprising this third generation LV system are identical in both methods. The advantage of the co-transfection method is that a single preparation of LV, containing vectors encoding both CARs is created. As can be seen from the data, nearly identical patterns of CD20-CD19 CAR and CD22 CAR expression are seen, as compared to the co-transduction method in the second row. The staining pattern for both glycoproteins induced by LV generated by co-transfection (CD22 for the CD22-CAR and CD19 co-staining for the CD20_19 CAR) in the upper right quadrant of the data in the second column, demonstrates that both methods efficiently generate DuoCARs.

REFERENCED LITERATURE

1) Wu, A. M., et al., Multimerization of a chimeric anti-CD20 single-chain Fv-Fc fusion protein is mediated through variable domain exchange. Protein engineering, 2001. 14(12): p. 1025-1033.
2) Haso, W., et al., Anti-CD22-chimeric antigen receptors targeting B-cell precursor acute lymphoblastic leukemia. Blood, 2013. 121(7): p. 1165-1174.
3) Kuroda, H., et al., Simplified lentivirus vector production in protein-free media using polyethylenimine-mediated transfection. Journal of virological methods, 2009. 157 (2): p. 113-121.

SEQUENCE LISTING

The nucleic and amino acid sequences listed below are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

```
SEQ ID NO: 1 is the nucleotide sequence of
CD20-reactive scFv binding domain LTG1495):
GAGGTGCAGTTGCAACAGTCAGGAGCTGAACTGGTCAAGCCAGGAGCCAG

CGTGAAGATGAGCTGCAAGGCCTCCGGTTACACCTTCACCTCCTACAACA

TGCACTGGGTGAAACAGACCCCGGGACAAGGGCTCGAATGGATTGGCGCC

ATCTACCCCGGGAATGGCGATACTTCGTACAACCAGAAGTTCAAGGGAAA

GGCCACCCTGACCGCCGACAAGAGCTCCTCCACCGCGTATATGCAGTTGA
```

-continued
GCTCCCTGACCTCCGAGGACTCCGCCGACTACTACTGCGCACGGTCCAAC
TACTATGGAAGCTCGTACTGGTTCTTCGATGTCTGGGGGGCCGGCACCAC
TGTGACCGTCAGCTCCGGGGGCGGAGGATCCGGTGGAGGCGGAAGCGGGG
GTGGAGGATCCGACATTGTGCTGACTCAGTCCCCGGCAATCCTGTCGGCC
TCACCGGGCGAAAAGGTCACGATGACTTGTAGAGCGTCGTCCAGCGTGAA
CTACATGGATTGGTACCAAAAGAAGCCTGGATCGTCACCCAAGCCTTGGA
TCTACGCTACATCTAACCTGGCCTCCGGCGTGCCAGCGCGGTTCAGCGGG
TCCGGCTCGGGCACCTCATACTCGCTGACCATCTCCCGCGTGGAGGCTGA
GGACGCCGCGACCTACTACTGCCAGCAGTGGTCCTTCAACCCGCCGACTT
TTGGAGGCGGTACTAAGCTGGAGATCAAA SEQ ID NO: 2 is the amino acid sequence of
CD20-reactive scFv binding domain (LTG1495):
EVQLQQSGAELVKPGASVKMSCKASGYTFTSYNMHWVKQTPGQGLEWIGA
IYPGNGDTSYNQKFKGKATLTADKSSSTAYMQLSSLTSEDSADYYCARSN
YYGSSYWFFDVWGAGTTVTVSSGGGGSGGGGSGGGGSDIVLTQSPAILSA
SPGEKVTMTCRASSSVNYMDWYQKKPGSSPKPWIYATSNLASGVPARFSG
SGSGTSYSLTISRVEAEDAATYYCQQWSFNPPTFGGGTKLEIK SEQ ID NO: 3 nucleotide sequence of the CAR
LTG1495 (LP-1495-CD8 TM-41BB-CD3zeta):
ATGCTCCTTCTCGTGACCTCCCTGCTTCTCTGCGAACTGCCCCATCCTGC
CTTCCTGCTGATTCCCGAGGTGCAGTTGCAACAGTCAGGAGCTGAACTGG
TCAAGCCAGGAGCCAGCGTGAAGATGAGCTGCAAGGCCTCCGGTTACACC
TTCACCTCCTACAACATGCACTGGGTGAAACAGACCCCGGGACAAGGGCT
CGAATGGATTGGCGCCATCTACCCCGGGAATGGCGATACTTCGTACAACC
AGAAGTTCAAGGGAAAGGCCACCCTGACCGCCGACAAGAGCTCCTCCACC
GCGTATATGCAGTTGAGCTCCCTGACCTCCGAGGACTCCGCCGACTACTA
CTGCGCACGGTCCAACTACTATGGAAGCTCGTACTGGTTCTTCGATGTCT
GGGGGGCCGGCACCACTGTGACCGTCAGCTCCGGGGGCGGAGGATCCGGT
GGAGGCGGAAGCGGGGGTGGAGGATCCGACATTGTGCTGACTCAGTCCCC
GGCAATCCTGTCGGCCTCACCGGGCGAAAAGGTCACGATGACTTGTAGAG
CGTCGTCCAGCGTGAACTACATGGATTGGTACCAAAAGAAGCCTGGATCG
TCACCCAAGCCTTGGATCTACGCTACATCTAACCTGGCCTCCGGCGTGCC
AGCGCGGTTCAGCGGGTCCGGCTCGGGCACCTCATACTCGCTGACCATCT
CCCGCGTGGAGGCTGAGGACGCCGCGACCTACTACTGCCAGCAGTGGTCC
TTCAACCCGCCGACTTTTGGAGGCGGTACTAAGCTGGAGATCAAAGCGGC
CGCAACTACCACCCCTGCCCCTCGGCCGCCGACTCCGGCCCCAACCATCG
CAAGCCAACCCCTCTCCTTGCGCCCCGAAGCTTGCCGCCCGGCCGCGGGT
GGAGCCGTGCATACCCGGGGGCTGGACTTTGCCTGCGATATCTACATTTG
GGCCCCGCTGGCCGGCACTTGCGGCGTGCTCCTGCTGTCGCTGGTCATCA
CCCTTTACTGCAAGAGGGGCCGGAAGAAGCTGCTTTACATCTTCAAGCAG
CCGTTCATGCGGCCCGTGCAGACGACTCAGGAAGAGGACGGATGCTCGTG
CAGATTCCCTGAGGAGGAAGAGGGGGGATGCGAACTGCGCGTCAAGTTCT
CACGGTCCGCCGACGCCCCCGCATATCAACAGGGCCAGAATCAGCTCTAC -continued
AACGAGCTGAACCTGGGAAGGAGAGAGGAGTACGACGTGCTGGACAAGCG
ACGCGGACGCGACCCGGAGATGGGGGGGAAACCACGGCGGAAAAACCCTC
AGGAAGGACTGTACAACGAACTCCAGAAAGACAAGATGGCGGAAGCCTAC
TCAGAAATCGGGATGAAGGGAGAGCGGAGGAGGGGAAAGGGTCACGACGG
GCTGTACCAGGGACTGAGCACCGCCACTAAGGATACCTACGATGCCTTGC
ATATGCAAGCACTCCCACCCCGG SEQ ID NO: 4 amino acid sequence of CAR LTG1495
(LP-1495-CD8 TM-41BB-CD3zeta):
MLLLVTSLLLCELPHPAFLLIPEVQLQQSGAELVKPGASVKMSCKASGYT
FTSYNMHWVKQTPGQGLEWIGAIYPGNGDTSYNQKFKGKATLTADKSSST
AYMQLSSLTSEDSADYYCARSNYYGSSYWFFDVWGAGTTVTVSSGGGGSG
GGGSGGGGSDIVLTQSPAILSASPGEKVTMTCRASSSVNYMDWYQKKPGS
SPKPWIYATSNLASGVPARFSGSGSGTSYSLTISRVEAEDAATYYCQQWS
FNPPTFGGGTKLEIKAAATTTPAPRPPTPAPTIASQPLSLRPEACRPAAG
GAVHTRGLDFACDIYIWAPLAGTCGVLLLSLVITLYCKRGRKKLLYIFKQ
PFMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEAY
SEIGMKGERRRGKGHDGLYQGLSTATKDTYDALHMQALPPR SEQ ID NO: 5 is the nucleotide sequence of
leader/signal peptide sequence:
ATGCTGCTGCTGGTGACCAGCCTGCTGCTGTGCGAACTGCCGCATCCGGC
GTTTCTGCTGATTCCG SEQ ID NO: 6 is the amino acid sequence of
leader/signal peptide sequence:
MLLLVTSLLLCELPHPAFLLIP SEQ ID NO: 7 is the nucleotide sequence of
CD22-reactive scFv binding domain LTG2200):
CAGGTACAGCTCCAGCAGAGTGGCCCAGGGCTCGTGAAGCCAAGCCAGAC
GCTGTCCCTGACTTGTGCAATTTCAGGGGATTCAGTTTCATCAAATAGCG
CGGCGTGGAATTGGATTCGACAATCTCCTTCCCGAGGGTTGGAATGGCTT
GGACGAACATATTACAGATCCAAATGGTATAACGACTATGCGGTATCAGT
AAAGTCAAGAATAACCATTAACCCCGACACAAGCAAGAACCAATTCTCTT
TGCAGCTTAACTCTGTCACGCCAGAAGACACGGCAGTCTATTATTGCGCT
CGCGAGGTAACGGGTGACCTGGAAGACGCTTTTGACATTTGGGGGCAGGG
TACGATGGTGACAGTCAGTTCAGGGGCGGTGGGAGTGGGGAGGGGTA
GCGGGGGGGAGGGTCAGACATTCAGATGACCCAGTCCCCTTCATCCTTG
TCTGCCTCCGTCGGTGACAGGGTGACAATAACATGCAGAGCAAGCCAAAC
AATCTGGAGCTATCTCAACTGGTACCAGCAGCGACCAGGAAAAGCGCCAA
ACCTGCTGATTTACGCTGCTTCCTCCCTCCAATCAGGCGTGCCTAGTAGA
TTTAGCGGTAGGGGCTCCGGCACCGATTTTACGCTCACTATAAGCTCTCT
TCAAGCAGAAGATTTTGCGACTTATTACTGCCAGCAGTCCTATAGTATAC
CTCAGACTTTCGGACAGGGTACCAAGTTGGAGATTAAGGCGGCCGCA SEQ ID NO: 8 is the amino acid sequence of
CD22-reactive scFv binding domain (LTG2200):
QVQLQQSGPGLVKPSQTLSLTCAISGDSVSSNSAAWNIRQSPSRGLEWL
GRTYYRSKWYNDYAVSVKSRITINPDTSKNQFSLQLNSVTPEDTAVYYCA
REVTGLDEDAFDIWGQGTMVTVSSGGGGSGGGGSGGGGSDIQMTQSPSSL
SASVGDRVTITCRASQTIWSYLNWYQQRPGKAPNLLIYAASSLQSGVPSR
FSGRGSGTDFTLTISSLQAEDFATYYCQQSYSIPQTFGQGTKLEIKAAA SEQ ID NO: 9 nucleotide sequence of the CAR
LTG2200 (LP-2200-CD8 TM-41BB-CD3zeta):
ATGCTTCTTTTGGTGACTTCCCTTTTGCTGTGCGAGTTGCCACACCCCGC
CTTCCTGCTTATTCCCCAGGTACAGCTCCAGCAGAGTGGCCCAGGGCTCG
TGAAGCCAAGCCAGACGCTGTCCCTGACTTGTGCAATTTCAGGGGATTCA
GTTTCATCAAATAGCGCGGCGTGGAATTGGATTCGACAATCTCCTTCCCG
AGGGTTGGAATGGCTTGGACGAACATATTACAGATCCAAATGGTATAACG
ACTATGCGGTATCAGTAAAGTCAAGAATAACCATTAACCCCGACACAAGC
AAGAACCAATTCTCTTTGCAGCTTAACTCTGTCACGCCAGAAGACACGGC
AGTCTATTATTGCGCTCGCGAGGTAACGGGTGACCTGGAAGACGCTTTTG
ACATTTGGGGCAGGGTACGATGGTGACAGTCAGTTCAGGGGCGGTGGG
AGTGGGGAGGGGTAGCGGGGGGGAGGGTCAGACATTCAGATGACCCA
GTCCCCTTCATCCTTGTCTGCCTCCGTCGGTGACAGGGTGACAATAACAT
GCAGAGCAAGCCAAACAATCTGGAGCTATCTCAACTGGTACCAGCAGCGA
CCAGGAAAAGCGCCAAACCTGCTGATTTACGCTGCTTCCTCCCTCCAATC
AGGCGTGCCTAGTAGATTTAGCGGTAGGGGCTCCGGCACCGATTTTACGC
TCACTATAAGCTCTCTTCAAGCAGAAGATTTTGCGACTTATTACTGCCAG
CAGTCCTATAGTATACCTCAGACTTTCGGACAGGGTACCAAGTTGGAGAT
TAAGGCGGCCGCAACTACCACCCCTGCCCCTCGGCCGCCGACTCCGGCCC
CAACCATCGCAAGCCAACCCCTCTCCTTGCGCCCCGAAGCTTGCCGCCCG
GCCGCGGGTGGAGCCGTGCATACCCGGGGGCTGGACTTTGCCTGCGATAT
CTACATTTGGGCCCCGCTGGCCGGCACTTGCGGCGTGCTCCTGCTGTCGC
TGGTCATCACCCTTTACTGCAAGAGGGGCCGGAAGAAGCTGCTTTACATC
TTCAAGCAGCCGTTCATGCGGCCCGTGCAGACGACTCAGGAAGAGGACGG
ATGCTCGTGCAGATTCCCTGAGGAGGAAGAGGGGGATGCGAACTGCGCG
TCAAGTTCTCACGGTCCGCCGACGCCCCCGCATATCAACAGGGCCAGAAT
CAGCTCTACAACGAGCTGAACCTGGGAAGGAGAGAGGAGTACGACGTGCT
GGACAAGCGACGCGGACGCGACCCGGAGATGGGGGGGAAACCACGGCGGA
AAAACCCTCAGGAAGGACTGTACAACGAACTCCAGAAAGACAAGATGGCG
GAAGCCTACTCAGAAATCGGGATGAAGGGAGAGCGGAGGAGGGGAAAGGG
TCACGACGGGCTGTACCAGGGACTGAGCACCGCCACTAAGGATACCTACG
ATGCCTTGCATATGCAAGCACTCCCACCCCGG SEQ ID NO: 10 amino acid sequence of CAR LTG2200
(LP-2200-CD8 TM-41BB-CD3zeta):
MLLLVTSLLLCELPHPAFLLIPQVQLQQSGPGLVKPSQTLSLTCAISGDS
VSSNSAAWNWIRQSPSRGLEWLGRTYYRSKWYNDYAVSVKSRITINPDTS
KNQFSLQLNSVTPEDTAVYYCAREVTGLDEDAFDIWGQGTMVTVSSGGGG
SGGGGSGGGGSDIQMTQSPSSLSASVGDRVTITCRASQTIWSYLNWYQQR
PGKAPNLLIYAASSLQSGVPSRFSGRGSGTDFTLTISSLQAEDFATYYCQ
QSYSIPQTFGQGTKLEIKAAATTTPAPRPPTPAPTIASQPLSLRPEACRP
AAGGAVHTRGLDFACDIYIWAPLAGTCGVLLLSLVITLYCKRGRKKLLYI
FKQPFMRPVQTTQEEDGCSCRFPEEEEGGCELRVKFSRSADAPAYQQGQN
QLYNELNLGRREEYDVLDKRRGRDPEMGGKPRRKNPQEGLYNELQKDKMA
EAYSEIGMKGERRRGKGHDGLYQGLSTATKDTYDALHMQALPPR SEQ ID NO.: 11 is the nucleotide sequence of DNA
CD8 transmembrane domain:
ATCTACATCTGGGCGCCCTTGGCCGGGACTTGTGGGGTCCTTCTCCTGTC
ACTGGTTATCACCCTTTACTGC SEQ ID NO. 12 is the amino acid sequence of CD8
transmembrane domain:
IWAPLAGTCGVLLLSLVITLYC SEQ ID NO: 13 is the nucleotide sequence of DNA
CD8 hinge domain:
ACCACGACGCCAGCGCCGCGACCACCAACACCGGCGCCCACCATCGCGTC
GCAGCCCCTGTCCCTGCGCCCAGAGGCGTGCCGGCCAGCGGCGGGGGCG
CAGTGCACACGAGGGGCTGGACTTTGCCTGCGATATCTAC SEQ ID NO: 14 is the amino acid sequence of CD8
hinge domain:
TTTPAPRPPTPAPTIASQPLSLRPEACRPAAGGAVHTRGLDFACDIY SEQ ID NO: 15 is the amino acid sequence of
amino acid numbers 137 to 206 of the hinge and
transmembrane region of CD8.alpha. (NCBI RefSeq:
NP.sub.--001759.3):
TTTPAPRPPTPAPTIASQPLSLRPEACRPAAGGAVHTRGLDFACDIYIWA
PLAGTCGVLLLSLVITLYC SEQ ID NO: 16 is the amino acid sequence of
Human IgG CL sequence:
GQPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKTV
APTECS SEQ ID NO 17 is the nucleotide sequence of DNA
signaling domain of 4-1BB:
AAACGGGCAGAAAGAAACTCCTGTATATATTCAAACAACCATTTATGAG
ACCAGTACAAACTACTCAAGAGGAAGATGGCTGTAGCTGCCGATTTCCAG
AAGAAGAAGAAGGAGGATGTGAACTG SEQ ID NO: 18 is the amino acid sequence of
signaling domain of 4-1BB:
KRGRKKLLYIFKQPFMRPVQTTQEEDGCSCRFPEEEEGGCEL SEQ ID NO: 19 is the nucleotide sequence of DNA
signaling domain of CD3-zeta:
AGAGTGAAGTTCAGCAGGAGCGCAGACGCCCCCGCGTACAAGCAGGGCCA
GAACCAGCTCTATAACGAGCTCAATCTAGGACGAAGAGAGGAGTACGATG
TTTTGGACAAGAGACGTGGCCGGGACCCTGAGATGGGGGGAAAGCCGAGA
AGGAAGAACCCTCAGGAAGGCCTGTACAATGAACTGCAGAAAGATAAGAT
GGCGGAGGCCTACAGTGAGATTGGGATGAAAGGCGAGCGCCGGAGGGGCA
AGGGGCACGATGGCCTTTACCAGGGTCTCAGTACAGCCACCAAGGACACC
TACGACGCCCTTCACATGCAGGCCCTGCCCCCTCGC SEQ ID NO: 20 is the amino acid sequence of
CD3zeta:
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

SEQ ID NO: 21 is the nucleotide sequence of CAR
LTG1562 (LP-CD19binder-CD8linker-CD4tm-4-1BB-CD3-
zeta):
ATGCTGCTGCTGGTGACCAGCCTGCTGCTGTGCGAACTGCCGCATCCGGC

GTTTCTGCTGATTCCGGATATTCAGATGACCCAGACCACCAGCAGCCTGA

GCGCGAGCCTGGGCGATCGCGTGACCATTAGCTGCCGCGCGAGCCAGGAT

ATTAGCAAATATCTGAACTGGTATCAGCAGAAACCGGATGGCACCGTGAA

ACTGCTGATTTATCATACCAGCCGCCTGCATAGCGGCGTGCCGAGCCGCT

TTAGCGGCAGCGGCAGCGGCACCGATTATAGCCTGACCATTAGCAACCTG

GAACAGGAAGATATTGCGACCTATTTTTGCCAGCAGGGCAACACCCTGCC

GTATACCTTTGGCGGCGGCACCAAACTGGAAATTACCGGCGGCGGCGGCA

GCGGCGGCGGCGGCAGCGGCGGCGGCGGCAGCGAAGTGAAACTGCAGGAA

AGCGGCCCGGGCCTGGTGGCGCCGAGCCAGAGCCTGAGCGTGACCTGCAC

CGTGAGCGGCGTGAGCCTGCCGGATTATGGCGTGAGCTGGATTCGCCAGC

CGCCGCGCAAAGGCCTGGAATGGCTGGGCGTGATTTGGGGCAGCGAAACC

ACCTATTATAACAGCGCGCTGAAAAGCCGCCTGACCATTATTAAAGATAA

CAGCAAAAGCCAGGTGTTTCTGAAAATGAACAGCCTGCAGACCGATGATA

CCGCGATTTATTATTGCGCGAAACATTATTATTATGGCGGCAGCTATGCG

ATGGATTATTGGGGCCAGGGCACCAGCGTGACCGTGAGCAGCGCGGCGGC

GCCGGCGCCGCGCCCGCCGACCCCGGCGCCGACCATTGCGAGCCAGCCGC

TGAGCCTGCGCCCGGAAGCGTGCCGCCCGGCGGCGGGCGGCGCGGTGCAT

ACCCGCGGCCTGGATTTTGTGCAGCCGATGGCGCTGATTGTGCTGGGCGG

CGTGGCGGGCCTGCTGCTGTTTATTGGCCTGGGCATTTTTTTTGCGTGC

GCTGCCGCCCGCGCCGAAAAAACTGCTGTATATTTTTAAACAGCCGTTT

ATGCGCCCGGTGCAGACCACCCAGGAAGAAGATGGCTGCAGCTGCCGCTT

TCCGGAAGAAGAAGGCGGCTGCGAACTGCGCGTGAAATTTAGCCGCA

GCGCGGATGCGCCGGCGTATCAGCAGGGCCAGAACCAGCTGTATAACGAA

CTGAACCTGGGCCGCCGCGAAGAATATGATGTGCTGGATAAACGCCGCGG

CCGCGATCCGGAAATGGGCGGCAAACCGCGCCGCAAAAACCCGCAGGAAG

GCCTGTATAACGAACTGCAGAAAGATAAAATGGCGGAAGCGTATAGCGAA

ATTGGCATGAAAGGCGAACGCCGCCGCGGCAAAGGCCATGATGGCCTGTA

TCAGGGCCTGAGCACCGCGACCAAAGATACCTATGATGCG CTGCATATG

CAGGCGCTGCCGCCGCGC

SEQ ID NO: 22 is the amino acid sequence of the
CAR LTG1562 (LP-CD19binder-CD8link-CD4tm-41BB-
CD3zeta):
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGGGSGGGGSGGGGSEVKLQE

SGPGLVAPSQSLSVTCTVSGVSLPDYGVSWIRQPPRKGLEWLGVIWGSET

TYYNSALKSRLTIIKDNSKSQVFLKMNSLQTDDTAIYYCAKHYYYGGSYA

MDYWGQGTSVTVSSAAAPAPRPPTPAPTIASQPLSLRPEACRPAAGGAVH

TRGLDFVQPMALIVLGGVAGLLLFIGLGIFFCVRCRPRRKKLLYIFKQPF

MRPVQTTQEEDGCSCRFPEEEEGGCELRVKFSRSADAPAYQQGQNQLYNE

LNLGRREEYDVLDKRRGRDPEMGGKPRRKNPQEGLYNELQKDKMAEAYSE

IGMKGERRRGKGHDGLYQGLSTATKDTYDALHMQALPPR

SEQ ID NO: 23 is the nucleotide sequence of
CD20_19-reactive scFv binding domain (LTG1497
dual specific binder):
GAGGTGCAGTTGCAACAGTCAGGAGCTGAACTGGTCAAGCCAGGAGCCAG

CGTGAAGATGAGCTGCAAGGCCTCCGGTTACACCTTCACCTCCTACAACA

TGCACTGGGTGAAACAGACCCCGGGACAAGGGCTCGAATGGATTGGCGCC

ATCTACCCCGGGAATGGCGATACTTCGTACAACCAGAAGTTCAAGGGAAA

GGCCACCCTGACCGCCGACAAGAGCTCCTCCACCGCGTATATGCAGTTGA

GCTCCCTGACCTCCGAGGACTCCGCCGACTACTACTGCGCACGGTCCAAC

TACTATGGAAGCTCGTACTGGTTCTTCGATGTCTGGGGGGCCGGCACCAC

TGTGACCGTCAGCTCCGGGGGCGGAGGATCCGGTGGAGGCGGAAGCGGGG

GTGGAGGATCCGACATTGTGCTGACTCAGTCCCCGGCAATCCTGTCGGCC

TCACCGGGCGAAAAGGTCACGATGACTTGTAGAGCGTCGTCCAGCGTGAA

CTACATGGATTGGTACCAAAAGAAGCCTGGATCGTCACCCAAGCCTTGGA

TCTACGCTACATCTAACCTGGCCTCCGGCGTGCCAGCGCGGTTCAGCGGG

TCCGGCTCGGGCACCTCATACTCGCTGACCATCTCCCGCGTGGAGGCTGA

GGACGCCGCGACCTACTACTGCCAGCAGTGGTCCTTCAACCCGCCGACTT

TTGGAGGCGGTACTAAGCTGGAGATCAAAGGAGGCGGCGGCAGCGGCGGG

GGAGGGTCCGGAGGGGGTGGTTCTGGTGGAGGAGGATCGGGAGGCGGTGG

CAGCGACATTCAGATGACTCAGACCACCTCCTCCCTGTCCGCCTCCCTGG

GCGACCGCGTGACCATCTCATGCCGCGCCAGCCAGGACATCTCGAAGTAC

CTCAACTGGTACCAGCAGAAGCCCGACGGAACCGTGAAGCTCCTGATCTA

CCACACCTCCCGGCTGCACAGCGGAGTGCCGTCTAGATTCTCGGGTTCGG

GGTCGGGAACTGACTACTCCCTTACTATTTCCAACCTGGAGCAGGAGGAT

ATTGCCACCTACTTCTGCCAACAAGGAAACACCCTGCCGTACACTTTTGG

CGGGGGAACCAAGCTGGAAATCACTGGCAGCACATCCGGTTCCGGGAAGC

CCGGCTCCGGAGAGGGCAGCACCAAGGGGGAAGTCAAGCTGCAGGAATCA

GGACCTGGCCTGGTGGCCCCGAGCCAGTCACTGTCCGTGACTTGTACTGT

GTCCGGAGTGTCGCTCCCGGATTACGGAGTGTCCTGGATCAGGCAGCCAC

CTCGGAAAGGATTGGAATGGCTCGGAGTCATCTGGGGTTCCGAAACCACC

TATTACAACTCGGCACTGAAATCCAGGCTCACCATTATCAAGGATAACTC

CAAGTCACAAGTGTTCCTGAAGATGAATAGCCTGCAGACTGACGACACGG

CGATCTACTATTGCGCCAAGCACTACTACTACGGCGGATCCTACGCTATG

GACTACTGGGGCCAGGGGACCAGCGTGACCGTGTCATCCGCGGCCGCA

SEQ ID NO: 24 is the amino acid sequence of CD20 19-reactive scFv binding domain (LTG1497 dual specific binder):

EVQLQQSGAELVKPGASVKMSCKASGYTFTSYNMHWVKQTPGQGLEWIGA

IYPGNGDTSYNQKFKGKATLTADKSSSTAYMQLSSLTSEDSADYYCARSN

YYGSSYWFFDVWGAGTTVTVSSGGGGSGGGGSGGGGSDIVLTQSPAILSA

SPGEKVTMTCRASSSVNYMDWYQKKPGSSPKPWIYATSNLASGVPARFSG

SGSGTSYSLTISRVEAEDAATYYCQQWSFNPPTFGGGTKLEIKGGGGSGG

GGSGGGGSGGGGSGGGGSDIQMTQTTSSLSASLGDRVTISCRASQDISKY

LNWYQQKPDGTVKLLIYHTSRLHSGVPSRFSGSGSGTDYSLTISNLEQED

IATYFCQQGNTLPYTFGGGTKLEITGSTSGSGKPGSGEGSTKGEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSSAAA

SEQ ID NO: 25 is the nucleotide sequence of the CAR LTG1497 (LP-LTG1497-CD8 TM-41BB-CD3zeta) or (LP-CD20 VH-(GGGGS)₃-CD20 VL-(GGGGS)₅-CD19VL-Whitlow linker-CD19 VH-CD8 hinge + TM-41BB-CD3zeta):

ATGCTCCTTCTCGTGACCTCCCTGCTTCTCTGCGAACTGCCCCATCCTGC

CTTCCTGCTGATTCCCGAGGTGCAGTTGCAACAGTCAGGAGCTGAACTGG

TCAAGCCAGGAGCCAGCGTGAAGATGAGCTGCAAGGCCTCCGGTTACACC

TTCACCTCCTACAACATGCACTGGGTGAAACAGACCCCGGGACAAGGGCT

CGAATGGATTGGCGCCATCTACCCCGGGAATGGCGATACTTCGTACAACC

AGAAGTTCAAGGGAAAGGCCACCCTGACCGCCGACAAGAGCTCCTCCACC

GCGTATATGCAGTTGAGCTCCCTGACCTCCGAGGACTCCGCCGACTACTA

CTGCGCACGGTCCAACTACTATGGAAGCTCGTACTGGTTCTTCGATGTCT

GGGGGGCCGGCACCACTGTGACCGTCAGCTCCGGGGGCGGAGGATCCGGT

GGAGGCGGAAGCGGGGGTGGAGGATCCGACATTGTGCTGACTCAGTCCCC

GGCAATCCTGTCGGCCTCACCGGGCGAAAAGGTCACGATGACTTGTAGAG

CGTCGTCCAGCGTGAACTACATGGATTGGTACCAAAAGAAGCCTGGATCG

TCACCCAAGCCTTGGATCTACGCTACATCTAACCTGGCCTCCGGCGTGCC

AGCGCGGTTCAGCGGGTCCGGCTCGGGCACCTCATACTCGCTGACCATCT

CCCGCGTGGAGGCTGAGGACGCCGCGACCTACTACTGCCAGCAGTGGTCC

TTCAACCCGCCGACTTTTGGAGGCGGTACTAAGCTGGAGATCAAAGGAGG

CGGCGGCAGCGGCGGGGAGGGTCCGGAGGGGGTGGTTCTGGTGGAGGAG

GATCGGGAGGCGGTGGCAGCGACATTCAGATGACTCAGACCACCTCCTCC

CTGTCCGCCTCCCTGGGCGACCGCGTGACCATCTCATGCCGCGCCAGCCA

GGACATCTCGAAGTACCTCAACTGGTACCAGCAGAAGCCCGACGGAACCG

TGAAGCTCCTGATCTACCACACCTCCCGGCTGCACAGCGGAGTGCCGTCT

AGATTCTCGGGTTCGGGGTCGGGAACTGACTACTCCCTTACTATTTCCAA

CCTGGAGCAGGAGGATATTGCCACCTACTTCTGCCAACAAGGAAACACCC

TGCCGTACACTTTTGGCGGGGGAACCAAGCTGGAAATCACTGGCAGCACA

TCCGGTTCCGGGAAGCCCGGCTCCGGAGAGGGCAGCACCAAGGGGGAAGT

CAAGCTGCAGGAATCAGGACCTGGCCTGGTGGCCCCGAGCCAGTCACTGT

CCGTGACTTGTACTGTGTCCGGAGTGTCGCTCCCGGATTACGGAGTGTCC

TGGATCAGGCAGCCACCTCGGAAAGGATTGGAATGGCTCGGAGTCATCTG

GGGTTCCGAAACCACCTATTACAACTCGGCACTGAAATCCAGGCTCACCA

TTATCAAGGATAACTCCAAGTCACAAGTGTTCCTGAAGATGAATAGCCTG

CAGACTGACGACACGGCGATCTACTATTGCGCCAAGCACTACTACTACGG

CGGATCCTACGCTATGGACTACTGGGGCCAGGGGACCAGCGTGACCGTGT

CATCCGCGGCCGCAACTACCACCCCTGCCCCTCGGCCGCCGACTCCGGCC

CCAACCATCGCAAGCCAACCCCTCTCCTTGCGCCCCGAAGCTTGCCGCCC

GGCCGCGGGTGGAGCCGTGCATACCCGGGGGCTGGACTTTGCCTGCGATA

TCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACAT

CTTCAAGCAGCCGTTCATGCGGCCCGTGCAGACGACTCAGGAAGAGGACG

GATGCTCGTGCAGATTCCCTGAGGAGGAAGAGGGGGATGCGAACTGCGC

GTCAAGTTCTCACGGTCCGCCGACGCCCCCGCATATCAACAGGGCCAGAA

TCAGCTCTACAACGAGCTGAACCTGGGAAGGAGAGAGGAGTACGACGTGC

TGGACAAGCGACGCGGACGCGACCCGGAGATGGGGGGGAAACCACGGCGG

AAAAACCCTCAGGAAGGACTGTACAACGAACTCCAGAAAGACAAGATGGC

GGAAGCCTACTCAGAAATCGGGATGAAGGGAGAGCGGAGGAGGGGAAAGG

GTCACGACGGGCTGTACCAGGGACTGAGCACCGCCACTAAGGATACCTAC

GATGCCTTGCATATGCAAGCACTCCCACCCCGG

SEQ ID NO: 26 is the amino acid sequence of the CAR LTG1497 (LP-LTG1497-CD8 TM-41BB-CD3zeta) or (LP-CD20 VH (GGGGS)₃-CD20 VL-(GGGGS)₅-CD19 VL-Whitlow linker-CD19 VH-CD8 hinge + TM-41BB-CD3zeta):

MLLLVTSLLLCELPHPAFLLIPEVQLQQSGAELVKPGASVKMSCKASGYT

FTSYNMHWVKQTPGQGLEWIGAIYPGNGDTSYNQKFKGKATLTADKSSST

AYMQLSSLTSEDSADYYCARSNYYGSSYWFFDVWGAGTTVTVSSGGGGSG

GGGSGGGGSDIVLTQSPAILSASPGEKVTMTCRASSSVNYMDWYQKKPGS

SPKPWIYATSNLASGVPARFSGSGSGTSYSLTISRVEAEDAATYYCQQWS

FNPPTFGGGTKLEIKGGGGSGGGGSGGGGSGGGGSGGGGSDIQMTQTTSS

LSASLGDRVTISCRASQDISKYLNWYQQKPDGTVKLLIYHTSRLHSGVPS

RFSGSGSGTDYSLTISNLEQEDIATYFCQQGNTLPYTFGGGTKLEITGST

SGSGKPGSGEGSTKGEVKLQESGPGLVAPSQSLSVTCTVSGVSLPDYGVS

WIRQPPRKGLEWLGVIWGSETTYYNSALKSRLTIIKDNSKSQVFLKMNSL

QTDDTAIYYCAKHYYYGGSYAMDYWGQGTSVTVSSAAATTTPAPRPPTPA

PTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR

SEQ ID NO: 27 is the nucleotide sequence of scFV for CD19:
GACATCCAGATGACACAGACTACATCCTCCCTGTCTGCCTCTCTGGGAGA
CAGAGTCACCATCAGTTGCAGGGCAAGTCAGGACATTAGTAAATATTTAA
ATTGGTATCAGCAGAAACCAGATGAACTGTTAAACTCCTGATCTACCAT
ACATCAAGATTACACTCAGGAGTCCCATCAAGGTTCAGTGGCAGTGGGTC
TGGAACAGATTATTCTCTCACCATTAGCAACCTGGAGCAAGAAGATATTG
CCACTTACTTTTGCCAACAGGGTAATACGCTTCCGTACACGTTCGGAGGG
GGGACCAAGCTGGAGATCACAGGTGGCGGTGGCTCGGGCGGTGGTGGGTC
GGGTGGCGGCGGATCTGAGGTGAAACTGCAGGAGTCAGGACCTGGCCTGG
TGGCGCCCTCACAGAGCCTGTCCGTCACATGCACTGTCTCAGGGGTCTCA
TTACCCGACTATGGTGTAAGCTGGATTCGCCAGCCTCCACGAAAGGGTCT
GGAGTGGCTGGGAGTAATATGGGGTAGTGAAACCACATACTATAATTCAG
CTCTCAAATCCAGACTGACCATCATCAAGGACAACTCCAAGAGCCAAGTT
TTCTTAAAAATGAACAGTCTGCAAACTGATGACACAGCCATTTACTACTG
TGCCAAACATTATTACTACGGTGGTAGCTATGCTATGGACTACTGGGGCC
AAGGAACCTCAGTCACCGTCTCCTCA SEQ ID NO: 28 is the amino acid sequence of scFV for CD19:
DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEITGGGSGGGGSGGGGSEVKLQESGPGLVAPSQSLSVTCTVSGVS
LPDYGVSWIRQPPRKGLEWLGVIWGSETTYYNSALKSRLTIIKDNSKSQV
FLKMNSLQTDDTAIYYCAKHYYYGGSYAMDYWGQGTSVTVSS SEQ ID NO: 29 is the nucleotide sequence of the CAR LTG 1494 (LP-CD19binder-CD8link-CD8tm-41BB-CD3zeta):
ATGCTTCTCCTGGTCACCTCCCTGCTCCTCTGCGAACTGCCTCACCCTGC
CTTCCTTCTGATTCCTGACACTGACATTCAGATGACTCAGACCACCTCTT
CCTTGTCCGCGTCACTGGGAGACAGAGTGACCATCTCGTGTCGCGCAAGC
CAGGATATCTCCAAGTACCTGAACTGGTACCAACAGAAGCCCGACGGGAC
TGTGAAGCTGCTGATCTACCACACCTCACGCCTGCACAGCGGAGTGCCAA
GCAGATTCTCCGGCTCCGGCTCGGGAACCGATTACTCGCTTACCATTAGC
AACCTCGAGCAGGAGGACATCGCTACCTACTTCTGCCAGCAAGGAAATAC
CCTGCCCTACACCTTCGGCGGAGGAACCAAATTGGAAATCACCGGCTCCA
CGAGCGGCTCCGGGAAGCCTGGTTCCGGGGAAGGCTCCACTAAGGGTGAA
GTGAAGCTCCAGGAGTCCGGCCCCGGCCTGGTGGCGCCGTCGCAATCACT
CTCTGTGACCTGTACCGTGTCGGGAGTGTCCCTGCCTGATTACGGCGTGA
GCTGGATTCGGCAGCCGCCGCGGAAGGGCCTGGAATGGCTGGGTGTCATC
TGGGGATCCGAGACTACCTACTACAACTCGGCCCTGAAGTCCCGCCTGAC
TATCATCAAAGACAACTCGAAGTCCCAGGTCTTTCTGAAGATGAACTCCC
TGCAAACTGACGACACCGCCATCTATTACTGTGCTAAGCACTACTACTAC
GGTGGAAGCTATGCTATGGACTACTGGGGCCAGGGACATCCGTGACAGT
CAGCTCCGCGGCCGCAACTACCACCCCTGCCCCTCGGCCGCCGACTCCGG CCCCAACCATCGCAAGCCAACCCCTCTCCTTGCGCCCCGAAGCTTGCCGC
CCGGCCGCGGGTGGAGCCGTGCATACCCGGGGGCTGGACTTTGCCTGCGA
TATCTACATTTGGGCCCCGCTGGCCGGCACTTGCGGCGTGCTCCTGCTGT
CGCTGGTCATCACCCTTTACTGCAAGAGGGGCCGGAAGAAGCTGCTTTAC
ATCTTCAAGCAGCCGTTCATGCGGCCCGTGCAGACGACTCAGGAAGAGGA
CGGATGCTCGTGCAGATTCCCTGAGGAGGAAGAGGGGGGATGCGAACTGC
GCGTCAAGTTCTCACGGTCCGCCGACGCCCCCGCATATCAACAGGGCCAG
AATCAGCTCTACAACGAGCTGAACCTGGGAAGGAGAGAGGAGTACGACGT
GCTGGACAAGCGACGCGGACGCGACCCGGAGATGGGGGGGAAACCACGGC
GGAAAAACCCTCAGGAAGGACTGTACAACGAACTCCAGAAAGACAAGATG
GCGGAAGCCTACTCAGAAATCGGGATGAAGGGAGAGCGGAGGAGGGGAAA
GGGTCACGACGGGCTGTACCAGGGACTGAGCACCGCCACTAAGGATACCT
ACGATGCCTTGCATATGCAAGCACTCCCACCCCGG SEQ ID NO: 30 is the amino acid sequence of the CAR LTG1494 (LP-CD19binder-CD8link-CD8tm-41BB-CD3zeta):
MLLLVTSLLLCELPHPAFLLIPDTDIQMTQTTSSLSASLGDRVTISCRAS
QDISKYLNWYQQKPDGTVKLLIYHTSRLHSGVPSRFSGSGSGTDYSLTIS
NLEQEDIATYFCQQGNTLPYTFGGGTKLEITGSTSGSGKPGSGEGSTKGE
VKLQESGPGLVAPSQSLSVTCTVSGVSLPDYGVSWIRQPPRKGLEWLGVI
WGSETTYYNSALKSRLTIIKDNSKSQVFLKMNSLQTDDTAIYYCAKHYYY
GGSYAMDYWGQGTSVTVSSAAATTTPAPRPPTPAPTIASQPLSLRPEACR
PAAGGAVHTRGLDFACDIYIWAPLAGTCGVLLLSLVITLYCKRGRKKLLY
IFKQPFMRPVQTTQEEDGCSCRFPEEEEGGCELRVKFSRSADAPAYQQGQ
NQLYNELNLGRREEYDVLDKRRGRDPEMGGKPRRKNPQEGLYNELQKDKM
AEAYSEIGMKGERRRGKGHDGLYQGLSTATKDTYDALHMQALPPR SEQ ID NO: 31 is the nucleotide sequence of the CAR LTG1538 (LP-CD19binder-CD8link-CD8tm-signals (LTI re-engineered CD19 CAR):
ATGCTTCTCCTGGTCACCTCCCTGCTCCTCTGCGAACTGCCTCACCCTGC
CTTCCTTCTGATTCCTGACATTCAGATGACTCAGACCACCTCTTCCTTGT
CCGCGTCACTGGGAGACAGAGTGACCATCTCGTGTCGCGCAAGCCAGGAT
ATCTCCAAGTACCTGAACTGGTACCAACAGAAGCCCGACGGGACTGTGAA
GCTGCTGATCTACCACACCTCACGCCTGCACAGCGGAGTGCCAAGCAGAT
TCTCCGGCTCCGGCTCGGGAACCGATTACTCGCTTACCATTAGCAACCTC
GAGCAGGAGGACATCGCTACCTACTTCTGCCAGCAAGGAAATACCCTGCC
CTACACCTTCGGCGGAGGAACCAAATTGGAAATCACCGGCGGAGGAGCT
CCGGGGGAGGAGGTTCCGGGGCGGGGGTTCCGAAGTGAAGCTCCAGGAG
TCCGGCCCCGGCCTGGTGGCGCCGTCGCAATCACTCTCTGTGACCTGTAC
CGTGTCGGGAGTGTCCCTGCCTGATTACGGCGTGAGCTGGATTCGGCAGC
CGCCGCGGAAGGGCCTGGAATGGCTGGGTGTCATCTGGGGATCCGAGACT
ACCTACTACAACTCGGCCCTGAAGTCCCGCCTGACTATCATCAAAGACAA
CTCGAAGTCCCAGGTCTTTCTGAAGATGAACTCCCTGCAAACTGACGACA

CCGCCATCTATTACTGTGCTAAGCACTACTACTACGGTGGAAGCTATGCT

ATGGACTACTGGGGGCAAGGCACTTCGGTGACTGTGTCAAGCGCGGCCGC

AACTACCACCCCTGCCCCTCGGCCGCCGACTCCGGCCCCAACCATCGCAA

GCCAACCCCTCTCCTTGCGCCCCGAAGCTTGCCGCCCGGCCGCGGGTGGA

GCCGTGCATACCCGGGGGCTGGACTTTGCCTGCGATATCTACATTTGGGC

CCCGCTGGCCGGCACTTGCGGCGTGCTCCTGCTGTCGCTGGTCATCACCC

TTTACTGCAAGAGGGGCCGGAAGAAGCTGCTTTACATCTTCAAGCAGCCG

TTCATGCGGCCCGTGCAGACGACTCAGGAAGAGGACGGATGCTCGTGCAG

ATTCCCTGAGGAGGAAGAGGGGGGATGCGAACTGCGCGTCAAGTTCTCAC

GGTCCGCCGACGCCCCCGCATATCAACAGGGCCAGAATCAGCTCTACAAC

GAGCTGAACCTGGGAAGGAGAGAGGAGTACGACGTGCTGGACAAGCGACG

CGGACGCGACCCGGAGATGGGGGGAAACCACGGCGGAAAAACCCTCAGG

AAGGACTGTACAACGAACTCCAGAAAGACAAGATGGCGGAAGCCTACTCA

GAAATCGGGATGAAGGGAGAGCGGAGGAGGGGAAAGGGTCACGACGGGCT

GTACCAGGGACTGAGCACCGCCACTAAGGATACCTACGATGCCTTGCATA

TGCAAGCACTCCCACCCCGG

SEQ ID NO: 32 is the amino acid sequence of the
CAR LTG1538 (LP-CD19binder-CD8link-CD8tm-signals
(LTI re-engineered CD19 CAR):
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGGGSGGGGSGGGGSEVKLQE

SGPGLVAPSQSLSVTCTVSGVSLPDYGVSWIRQPPRKGLEWLGVIWGSET

TYYNSALKSRLTIIKDNSKSQVFLKMNSLQTDDTAIYYCAKHYYYGGSYA

MDYWGQGTSVTVSSAAATTTPAPRPPTPAPTIASQPLSLRPEACRPAAGG

AVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID NO: 33 is the nucleotide sequence of
CD19_20-reactive scFv binding domain (LTG1496):
GACATTCAGATGACTCAGACCACCTCCTCCCTGTCCGCCTCCCTGGGCGA

CCGCGTGACCATCTCATGCCGCGCCAGCCAGGACATCTCGAAGTACCTCA

ACTGGTACCAGCAGAAGCCCGACGGAACCGTGAAGCTCCTGATCTACCAC

ACCTCCCGGCTGCACAGCGGAGTGCCGTCTAGATTCTCGGGTTCGGGTC

GGGAACTGACTACTCCCTTACTATTTCCAACCTGGAGCAGGAGGATATTG

CCACCTACTTCTGCCAACAAGGAAACACCCTGCCGTACACTTTTGGCGGG

GGAACCAAGCTGGAAATCACTGGCAGCACATCCGGTTCCGGGAAGCCCGG

CTCCGGAGAGGGCAGCACCAAGGGGGAAGTCAAGCTGCAGGAATCAGGAC

CTGGCCTGGTGGCCCCGAGCCAGTCACTGTCCGTGACTTGTACTGTGTCC

GGAGTGTCGCTCCCGGATTACGGAGTGTCCTGGATCAGGCAGCCACCTCG

GAAAGGATTGGAATGGCTCGGAGTCATCTGGGGTTCCGAAACCACCTATT

ACAACTCGGCACTGAAATCCAGGCTCACCATTATCAAGGATAACTCCAAG

TCACAAGTGTTCCTGAAGATGAATAGCCTGCAGACTGACGACACGGCGAT

CTACTATTGCGCCAAGCACTACTACTACGGCGGATCCTACGCTATGGACT

ACTGGGGCCAGGGGACCAGCGTGACCGTGTCATCCGGAGGCGGCGGCAGC

GGCGGGGGAGGGTCCGGAGGGGGTGGTTCTGGTGGAGGAGGATCGGAGG

CGGTGGCAGCGAGGTGCAGTTGCAACAGTCAGGAGCTGAACTGGTCAAGC

CAGGAGCCAGCGTGAAGATGAGCTGCAAGGCCTCCGGTTACACCTTCACC

TCCTACAACATGCACTGGGTGAAACAGACCCCGGACAAGGGCTCGAATG

GATTGGCGCCATCTACCCCGGGAATGGCGATACTTCGTACAACCAGAAGT

TCAAGGGAAAGGCCACCCTGACCGCCGACAAGAGCTCCTCCACCGCGTAT

ATGCAGTTGAGCTCCCTGACCTCCGAGGACTCCGCCGACTACTACTGCGC

ACGGTCCAACTACTATGGAAGCTCGTACTGGTTCTTCGATGTCTGGGGGG

CCGGCACCACTGTGACCGTCAGCTCCGGGGGCGGAGGATCCGGTGGAGGC

GGAAGCGGGGGTGGAGGATCCGACATTGTGCTGACTCAGTCCCCGGCAAT

CCTGTCGGCCTCACCGGGCGAAAAGGTCACGATGACTTGTAGAGCGTCGT

CCAGCGTGAACTACATGGATTGGTACCAAAAGAAGCCTGGATCGTCACCC

AAGCCTTGGATCTACGCTACATCTAACCTGGCCTCCGGCGTGCCAGCGCG

GTTCAGCGGGTCCGGCTCGGGCACCTCATACTCGCTGACCATCTCCCGCG

TGGAGGCTGAGGACGCCGCGACCTACTACTGCCAGCAGTGGTCCTTCAAC

CCGCCGACTTTTGGAGGCGGTACTAAGCTGGAGATCAAAGCGGCCGCA

SEQ ID NO: 34 is the amino acid sequence of
CD19_20-reactive scFv binding domain (LTG1496):
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGSTSGSGKPGSGEGSTKGEVKLQESGPGLVAPSQSLSVTCTVS

GVSLPDYGVSWIRQPPRKGLEWLGVIWGSETTYYNSALKSRLTIIKDNSK

SQVFLKMNSLQTDDTAIYYCAKHYYYGGSYAMDYWGQGTSVTVSSGGGGS

GGGGSGGGGSGGGGSGGGGSEVQLQQSGAELVKPGASVKMSCKASGYTFT

SYNMHWVKQTPGQGLEWIGAIYPGNGDTSYNQKFKGKATLTADKSSTAY

MQLSSLTSEDSADYYCARSNYYGSSYWFFDVWGAGTTVTVSSGGGGSGGG

GSGGGGSDIVLTQSPAILSASPGEKVTMTCRASSSVNYMDWYQKKPGSSP

KPWIYATSNLASGVPARFSGSGSGTSYSLTISRVEAEDAATYYCQQWSFN

PPTFGGGTKLEIKAAA

SEQ ID NO: 35 is the nucleotide sequence of the
CAR LTG1496 (LP-LTG1496-CD8 TM-41BB-CD3zeta) or
(LP-CD19 VL-Whitlow linker-CD19 VH (GGGGS)5 CD20
VH (GGGGS)3-CD20 VL CD8 hinge + TM-41BB-CD3zeta):
ATGCTCCTTCTCGTGACCTCCCTGCTTCTCTGCGAACTGCCCCATCCTGC

CTTCCTGCTGATTCCCGACATTCAGATGACTCAGACCACCTCCTCCCTGT

CCGCCTCCCTGGGCGACCGCGTGACCATCTCATGCCGCGCCAGCCAGGAC

ATCTCGAAGTACCTCAACTGGTACCAGCAGAAGCCCGACGGAACCGTGAA

GCTCCTGATCTACCACACCTCCCGGCTGCACAGCGGAGTGCCGTCTAGAT

TCTCGGGTTCGGGTCGGGAACTGACTACTCCCTTACTATTTCCAACCTGG

AGCAGGAGGATATTGCCACCTACTTCTGCCAACAAGGAAACACCCTGCC

GTACACTTTTGGCGGGGGAACCAAGCTGGAAATCACTGGCAGCACATCCG

```
GTTCCGGGAAGCCCGGCTCCGGAGAGGGCAGCACCAAGGGGGAAGTCAAG

CTGCAGGAATCAGGACCTGGCCTGGTGGCCCCGAGCCAGTCACTGTCCGT

GACTTGTACTGTGTCCGGAGTGTCGCTCCCGGATTACGGAGTGTCCTGGA

TCAGGCAGCCACCTCGGAAAGGATTGGAATGGCTCGGAGTCATCTGGGGT

TCCGAAACCACCTATTACAACTCGGCACTGAAATCCAGGCTCACCATTAT

CAAGGATAACTCCAAGTCACAAGTGTTCCTGAAGATGAATAGCCTGCAGA

CTGACGACACGGCGATCTACTATTGCGCCAAGCACTACTACTACGGCGGA

TCCTACGCTATGGACTACTGGGGCCAGGGGACCAGCGTGACCGTGTCATC

CGGAGGCGGCGGCAGCGGCGGGGAGGGTCCGGAGGGGGTGGTTCTGGTG

GAGGAGGATCGGGAGGCGGTGGCAGCGAGGTGCAGTTGCAACAGTCAGGA

GCTGAACTGGTCAAGCCAGGAGCCAGCGTGAAGATGAGCTGCAAGGCCTC

CGGTTACACCTTCACCTCCTACAACATGCACTGGGTGAAACAGACCCCGG

GACAAGGGCTCGAATGGATTGGCGCCATCTACCCCGGGAATGGCGATACT

TCGTACAACCAGAAGTTCAAGGGAAAGGCCACCCTGACCGCCGACAAGAG

CTCCTCCACCGCGTATATGCAGTTGAGCTCCCTGACCTCCGAGGACTCCG

CCGACTACTACTGCGCACGGTCCAACTACTATGGAAGCTCGTACTGGTTC

TTCGATGTCTGGGGGGCCGGCACCACTGTGACCGTCAGCTCCGGGGGCGG

AGGATCCGGTGGAGGCGGAAGCGGGGGTGGAGGATCCGACATTGTGCTGA

CTCAGTCCCCGGCAATCCTGTCGGCCTCACCGGGCGAAAAGGTCACGATG

ACTTGTAGAGCGTCGTCCAGCGTGAACTACATGGATTGGTACCAAAAGAA

GCCTGGATCGTCACCCAAGCCTTGGATCTACGCTACATCTAACCTGGCCT

CCGGCGTGCCAGCGCGGTTCAGCGGGTCCGGCTCGGGCACCTCATACTCG

CTGACCATCTCCCGCGTGGAGGCTGAGGACGCCGCGACCTACTACTGCCA

GCAGTGGTCCTTCAACCCGCCGACTTTTGGAGGCGGTACTAAGCTGGAGA

TCAAAGCGGCCGCAACTACCACCCCTGCCCCTCGGCCGCCGACTCCGGCC

CCAACCATCGCAAGCCAACCCCTCTCCTTGCGCCCCGAAGCTTGCCGCCC

GGCCGCGGGTGGAGCCGTGCATACCCGGGGCTGGACTTTGCCTGCGATA

TCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACAT

CTTCAAGCAGCCGTTCATGCGGCCCGTGCAGACGACTCAGGAAGAGGACG

GATGCTCGTGCAGATTCCTGAGGAGGAAGAGGGGGGATGCGAACTGCGC

GTCAAGTTCTCACGGTCCGCCGACGCCCCCGCATATCAACAGGGCCAGAA

TCAGCTCTACAACGAGCTGAACCTGGAAGGAGAGAGGAGTACGACGTGC

TGGACAAGCGACGCGGACGCGACCCGGAGATGGGGGGGAAACCACGGCGG

AAAAACCCTCAGGAAGGACTGTACAACGAACTCCAGAAAGACAAGATGGC

GGAAGCCTACTCAGAAATCGGGATGAAGGGAGAGCGGAGGAGGGGAAAGG

GTCACGACGGGCTGTACCAGGGACTGAGCACCGCCACTAAGGATACCTAC

GATGCCTTGCATATGCAAGCACTCCCACCCCGG
```

SEQ ID NO: 36 amino acid sequence of the CAR LTG1496 (LP-LTG1496-CD8 TM-41BB-CD3zeta) or (LP-CD19 VL-Whitlow linker-CD19 VH-(GGGGS)$_5$-CD20 VH (GGGGS)$_3$-CD20 VL-CD8 hinge + TM-41BB-CD3zeta):
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSGGGGSGGGGSGGGGSGGGGSGGGGSEVQLQQSG
AELVKPGASVKMSCKASGYTFTSYNMHWVKQTPGQGLEWIGAIYPGNGDT
SYNQKFKGKATLTADKSSSTAYMQLSSLTSEDSADYYCARSNYYGSSYWF
FDVWGAGTTVTVSSGGGGSGGGGSGGGGSDIVLTQSPAILSASPGEKVTM
TCRASSSVNYMDWYQKKPGSSPKPWIYATSNLASGVPARFSGSGSGTSYS
LTISRVEAEDAATYYCQQWSFNPPTFGGGTKLEIKAAATTTPAPRPPTPA
PTIASQPLSLRPEACRPAAGGAVHTRGLDFACDIYIWAPLAGTCGVLLLS
LVITLYCKRGRKKLLYIFKQPFMRPVQTTQEEDGCSCRFPEEEEGGCELR
VKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTY
DALHMQALPPR SEQ ID NO: 37 is the nucleotide sequence of mesothelin-reactive scFv binding domain (LTG1904):
GAGGTCCAGCTGGTACAGTCTGGGGGAGGCTTGGTACAGCCTGGGGGGTC
CCTGAGACTCTCCTGTGCAGCCTCTGGATTCACCTTTGATGATTATGCCA
TGCACTGGGTCCGGCAAGCTCCAGGGAAGGGCCTGGAGTGGGTCTCAGGT
ATTAGTTGGAATAGTGGTAGCATAGGCTATGCGGACTCTGTGAAGGGCCG
ATTCACCATCTCCAGAGACAACGCCAAGAACTCCCTGTATCTGCAAATGA
ACAGTCTGAGAGCTGAGGACACGGCCTTGTATTACTGTGCAAAAGATTTA
TCGTCAGTGGCTGGACCCTTTAACTACTGGGGCCAGGGCACCCTGGTCAC
CGTCTCCTCAGGAGGTGGCGGGTCTGGTGGAGGCGGTAGCGGCGGTGGCG
GATCCTCTTCTGAGCTGACTCAGGACCCTGCTGTGTCTGTGGCCTTGGGA
CAGACAGTCAGGATCACATGCCAAGGAGACAGCCTCAGAAGCTATTATGC
AAGCTGGTACCAGCAGAAGCCAGGACAGGCCCCTGTACTTGTCATCTATG
GTAAAAACAACCGGCCCTCAGGGATCCCAGACCGATTCTCTGGCTCCAGC
TCAGGAAACACAGCTTCCTTGACCATCACTGGGGCTCAGGCGGAGGATGA
GGCTGACTATTACTGTAACTCCCGGGACAGCAGTGGTAACCATCTGGTAT
TCGGCGGAGGCACCCAGCTGACCGTCCTCGGT SEQ ID NO: 38 is the amino acid sequence of mesothelin-reactive scFv binding domain (LTG1904):
EVQLVQSGGGLVQPGGSLRLSCAASGFTFDDYAMHWVRQAPGKGLEWVSG
ISWNSGSIGYADSVKGRFTISRDNAKNSLYLQMNSLRAEDTALYYCAKDL
SSVAGPFNYWGQGTLVTVSSGGGGSGGGGSGGGGSSSELTQDPAVSVALG

QTVRITCQGDSLRSYYASWYQQKPGQAPVLVIYGKNNRPSGIPDRFSGSS

SGNTASLTITGAQAEDEADYYCNSRDSSGNHLVFGGGTQLTVLG

SEQ ID NO: 39 nucleotide sequence of the CAR
LTG1904 (LP-LTG1904-CD8 TM-41BB-CD3 zeta):
ATGCTGCTGCTGGTGACCAGCCTGCTGCTGTGCGAACTGCCGCATCCGGC

GTTTCTGCTGATTCCGGAGGTCCAGCTGGTACAGTCTGGGGGAGGCTTGG

TACAGCCTGGGGGGTCCCTGAGACTCTCCTGTGCAGCCTCTGGATTCACC

TTTGATGATTATGCCATGCACTGGGTCCGGCAAGCTCCAGGGAAGGGCCT

GGAGTGGGTCTCAGGTATTAGTTGGAATAGTGGTAGCATAGGCTATGCGG

ACTCTGTGAAGGGCCGATTCACCATCTCCAGAGACAACGCCAAGAACTCC

CTGTATCTGCAAATGAACAGTCTGAGAGCTGAGGACACGGCCTTGTATTA

CTGTGCAAAAGATTTATCGTCAGTGGCTGGACCCTTTAACTACTGGGGCC

AGGGCACCCTGGTCACCGTCTCCTCAGGAGGTGGCGGGTCTGGTGGAGGC

GGTAGCGGCGGTGGCGGATCCTCTTCTGAGCTGACTCAGGACCCTGCTGT

GTCTGTGGCCTTGGGACAGACAGTCAGGATCACATGCCAAGGAGACAGCC

TCAGAAGCTATTATGCAAGCTGGTACCAGCAGAAGCCAGGACAGGCCCCT

GTACTTGTCATCTATGGTAAAAACAACCGGCCCTCAGGGATCCCAGACCG

ATTCTCTGGCTCCAGCTCAGGAAACACAGCTTCCTTGACCATCACTGGGG

CTCAGGCGGAGGATGAGGCTGACTATTACTGTAACTCCCGGGACAGCAGT

GGTAACCATCTGGTATTCGGCGGAGGCACCCAGCTGACCGTCCTCGGTGC

GGCCGCAACTACCACCCCTGCCCCTCGGCCGCCGACTCCGGCCCCAACCA

TCGCAAGCCAACCCCTCTCCTTGCGCCCCGAAGCTTGCCGCCCGGCCGCG

GGTGGAGCCGTGCATACCCGGGGGCTGGACTTTGCCTGCGATATCTACAT

TTGGGCCCCGCTGGCCGGCACTTGCGGCGTGCTCCTGCTGTCGCTGGTCA

TCACCCTTTACTGCAAGAGGGGCCGGAAGAAGCTGCTTTACATCTTCAAG

CAGCCGTTCATGCGGCCCGTGCAGACGACTCAGGAAGAGGACGGATGCTC

GTGCAGATTCCCTGAGGAGGAAGAGGGGGGATGCGAACTGCGCGTCAAGT

TCTCACGGTCCGCCGACGCCCCCGCATATCAACAGGGCCAGAATCAGCTC

TACAACGAGCTGAACCTGGGAAGGAGAGAGGAGTACGACGTGCTGGACAA

GCGACGCGGACGCGACCCGGAGATGGGGGGGAAACCACGGCGGAAAAACC

CTCAGGAAGGACTGTACAACGAACTCCAGAAAGACAAGATGGCGGAAGCC

TACTCAGAAATCGGGATGAAGGAGAGCGGAGGAGGGGAAAGGGTCACGA

CGGGCTGTACCAGGGACTGAGCACCGCCACTAAGGATACCTACGATGCCT

TGCATATGCAAGCACTCCCACCCCGG

SEQ ID NO: 40 amino acid sequence of the CAR
LTG1904 (LP-LTG1904-CD8 TM-41BB-CD3zeta):
MLLLVTSLLLCELPHPAFLLIPEVQLVQSGGGLVQPGGSLRLSCAASGFT

FDDYAMHWVRQAPGKGLEWVSGISWNSGSIGYADSVKGRFTISRDNAKNS

LYLQMNSLRAEDTALYYCAKDLSSVAGPFNYWGQGTLVTVSSGGGGSGGG

GSGGGGSSSELTQDPAVSVALGQTVRITCQGDSLRSYYASWYQQKPGQAP

VLVIYGKNNRPSGIPDRFSGSSSGNTASLTITGAQAEDEADYYCNSRDSS

GNHLVFGGGTQLTVLGAAATTTPAPRPPTPAPTIASQPLSLRPEACRPAA

GGAVHTRGLDFACDIYIWAPLAGTCGVLLLSLVITLYCKRGRKKLLYIFK

QPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEA

YSEIGMKGERRRGKGHDGLYQGLSTATKDTYDALHMQALPPR

SEQ ID NO: 41 is the nucleotide sequence of
CD33-reactive single chain binding domain
VH-4 (LTG1906):
GAGGTGCAGCTGGTGGAGTCTGGGGGAGGCTTGGTACAGCCTGGAGGGTC

CCTGAGACTCTCCTGTGCAGCCTCTGGATTCACCTTCAGTAGCTATGGCA

TGAGCTGGGTCCGCCAGGCTCCAAGACAAGGGCTTGAGTGGGTGGCCAAC

ATAAAGCAAGATGGAAGTGAGAAATACTATGCGGACTCAGTGAAGGGCCG

ATTCACCATCTCCAGAGACAATTCCAAGAACACGCTGTATCTGCAAATGA

ACAGCCTGAGAGCCGAGGACACAGCCACGTATTACTGTGCGAAAGAAAAT

GTGGACTGGGGCCAGGGCACCCTGGTCACCGTCTCCTCA

SEQ ID NO: 42 is the amino acid sequence of
CD33-reactive single chain binding domain
VH-4 (LTG1906):
EVQLVESGGGLVQPGGSLRLSCAASGFTFSSYGMSWVRQAPRQGLEWVAN

IKQDGSEKYYADSVKGRFTISRDNSKNTLYLQMNSLRAEDTATYYCAKEN

VDWGQGTLVTVSS

SEQ ID NO: 43 is the nucleotide sequence of the
CAR LTG1906 (LP-VH4-CD8 TM-41BB-CD3zeta):
ATGCTGCTGCTGGTGACCAGCCTGCTGCTGTGCGAACTGCCGCATCCGGC

GTTTCTGCTGATTCCGGAGGTGCAGCTGGTGGAGTCTGGGGGAGGCTTGG

TACAGCCTGGAGGGTCCCTGAGACTCTCCTGTGCAGCCTCTGGATTCACC

TTCAGTAGCTATGGCATGAGCTGGGTCCGCCAGGCTCCAAGACAAGGGCT

TGAGTGGGTGGCCAACATAAAGCAAGATGGAAGTGAGAAATACTATGCGG

ACTCAGTGAAGGGCCGATTCACCATCTCCAGAGACAATTCCAAGAACACG

CTGTATCTGCAAATGAACAGCCTGAGAGCCGAGGACACAGCCACGTATTA

CTGTGCGAAAGAAAATGTGGACTGGGGCCAGGGCACCCTGGTCACCGTCT

CCTCAGCGGCCGCAACTACCACCCCTGCCCCTCGGCCGCCGACTCCGGCC

CCAACCATCGCAAGCCAACCCCTCTCCTTGCGCCCCGAAGCTTGCCGCCC

GGCCGCGGGTGGAGCCGTGCATACCCGGGGGCTGGACTTTGCCTGCGATA

TCTACATTTGGGCCCCGCTGGCCGGCACTTGCGGCGTGCTCCTGCTGTCG

CTGGTCATCACCCTTTACTGCAAGAGGGGCCGGAAGAAGCTGCTTTACAT

CTTCAAGCAGCCGTTCATGCGGCCCGTGCAGACGACTCAGGAAGAGGACG

GATGCTCGTGCAGATTCCCTGAGGAGGAAGAGGGGGGATGCGAACTGCGC

GTCAAGTTCTCACGGTCCGCCGACGCCCCCGCATATCAACAGGGCCAGAA

TCAGCTCTACAACGAGCTGAACCTGGGAAGGAGAGAGGAGTACGACGTGC

TGGACAAGCGACGCGGACGCGACCCGGAGATGGGGGGGAAACCACGGCGG

AAAAACCCTCAGGAAGGACTGTACAACGAACTCCAGAAAGACAAGATGGC

GGAAGCCTACTCAGAAATCGGGATGAAGGAGAGCGGAGGAGGGGAAAGG

GTCACGACGGGCTGTACCAGGGACTGAGCACCGCCACTAAGGATACCTAC

GATGCCTTGCATATGCAAGCACTCCCACCCCGG

SEQ ID NO: 44 is the amino acid sequence of the
CAR LTG1906 (LP-VH4-CD8 TM-41BB-CD3 zeta):
MLLLVTSLLLCELPHPAFLLIPEVQLVESGGGLVQPGGSLRLSCAASGFT

FSSYGMSWVRQAPRQGLEWVANIKQDGSEKYYADSVKGRFTISRDNSKNT

LYLQMNSLRAEDTATYYCAKENVDWGQGTLVTVSSAAATTTPAPRPPTPA

PTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR

SEQ ID NO: 45 is the nucleotide sequence of
TSLPR-reactive scFv binding domain (LTG1789):
ATGGCACTGCCCGTGACCGCCCTGCTTCTGCCGCTTGCACTTCTGCTGCA

CGCCGCTAGGCCCCAAGTCACCCTCAAAGAGTCAGGGCCAGGAATCCTCA

AGCCCTCACAGACTCTGTCTCTTACTTGCTCATTCAGCGGATTCAGCCTT

TCCACCTCTGGTATGGGCGTGGGGTGGATTAGGCAACCTAGCGGAAAGGG

GCTTGAATGGCTGGCCCACATCTGGTGGGACGACGACAAGTACTACAACC

CCTCACTGAAGTCCCAGCTCACTATTTCCAAAGATACTTCCCGGAATCAG

GTGTTCCTCAAGATTACCTCTGTCGACACCGCTGATACCGCCACTTACTA

TTGTTCACGCAGACCGAGAGGTACCATGGACGCAATGGACTACTGGGGAC

AGGGCACCAGCGTGACCGTGTCATCTGGCGGTGGAGGGTCAGGAGGTGGA

GGTAGCGGAGGCGGTGGGTCCGACATTGTCATGACCCAGGCCGCCAGCAG

CCTGAGCGCTTCACTGGGCGACAGGGTGACCATCAGCTGTCGCGCATCAC

AAGATATCTCTAAGTATCTTAATTGGTACCAGCAAAAGCCGGATGGAACC

GTGAAGCTGCTGATCTACTACACCTCACGGCTGCATTCTGGAGTGCCTAG

CCGCTTTAGCGGATCTGGGTCCGGTACTGACTACAGCCTCACCATTAGAA

ACCTTGAACAGGAGGACATCGCAACTTATTTCTGCCAACAGGTCTATACT

CTGCCGTGGACCTTCGGCGGAGGTACCAAACTGGAGATTAAGTCCGG

SEQ ID NO: 46 is the amino acid sequence of
TSLPR-reactive scFv binding domain (LTG1789):
MALPVTALLLPLALLLHAARPQVTLKESGPGILKPSQTLSLTCSFSGFSL

STSGMGVGWIRQPSGKGLEWLAHIWWDDDKYYNPSLKSQLTISKDTSRNQ

VFLKITSVDTADTATYYCSRRPRGTMDAMDYWGQGTSVTVSSGGGGSGGG

GSGGGGSDIVMTQAASSLSASLGDRVTISCRASQDISKYLNWYQQKPDGT

VKLLIYYTSRLHSGVPSRFSGSGSGTDYSLTIRNLEQEDIATYFCQQVYT

LPWTFGGGTKLEIKS

SEQ ID NO: 47 is the nucleotide sequence of the
CAR LTG1789 (LP-3G11-CD8 TM-41BB-CD3 zeta):
ATGGCACTGCCCGTGACCGCCCTGCTTCTGCCGCTTGCACTTCTGCTGCA

CGCCGCTAGGCCCCAAGTCACCCTCAAAGAGTCAGGGCCAGGAATCCTCA

AGCCCTCACAGACTCTGTCTCTTACTTGCTCATTCAGCGGATTCAGCCTT

TCCACCTCTGGTATGGGCGTGGGGTGGATTAGGCAACCTAGCGGAAAGGG

GCTTGAATGGCTGGCCCACATCTGGTGGGACGACGACAAGTACTACAACC

CCTCACTGAAGTCCCAGCTCACTATTTCCAAAGATACTTCCCGGAATCAG

GTGTTCCTCAAGATTACCTCTGTCGACACCGCTGATACCGCCACTTACTA

TTGTTCACGCAGACCGAGAGGTACCATGGACGCAATGGACTACTGGGGAC

AGGGCACCAGCGTGACCGTGTCATCTGGCGGTGGAGGGTCAGGAGGTGGA

GGTAGCGGAGGCGGTGGGTCCGACATTGTCATGACCCAGGCCGCCAGCAG

CCTGAGCGCTTCACTGGGCGACAGGGTGACCATCAGCTGTCGCGCATCAC

AAGATATCTCTAAGTATCTTAATTGGTACCAGCAAAAGCCGGATGGAACC

GTGAAGCTGCTGATCTACTACACCTCACGGCTGCATTCTGGAGTGCCTAG

CCGCTTTAGCGGCACTTGCGCGTGCTCCTGCTGTCGCTGGTCATCACCC

TTTACTGCAAGAGGGGCCGGAAGAAGCTGCTTTACATCTTCAAGCAGCCG

TTCATGCGCCCGTGCAGACGACTCAGGAAGAGGACGGATGCTCGTGCAG

ATTCCCTGAGGAGGAAGAGGGGGGATGCGAACTGCGCGTCAAGTTCTCAC

GGTCCGCCGACGCCCCCGCATATCAACAGGGCCAGAATCAGCTCTACAAC

GAGCTGAACCTGGGAAGGAGAGAGGAGTACGACGTGCTGGACAAGCGACG

CGGACGCGACCCGGAGATGGGGGGGAAACCACGGCGGAAAAACCCTCAGG

AAGGACTGTACAACGAACTCCAGAAAGACAAGATGGCGGAAGCCTACTCA

GAAATCGGGATGAAGGGAGAGCGGAGGAGGGGAAAGGGTCACGACGGGCT

GTACCAGGGACTGAGCACCGCCACTAAGGATACCTACGATGCCTTGCATA

TGCAAGCACTCCCACCCCGG

SEQ ID NO: 48 is the amino acid sequence of the
CAR LTG1789 (LP-3G11-CD8 TM-41BB-CD3 zeta):
MALPVTALLLPLALLLHAARPQVTLKESGPGILKPSQTLSLTCSFSGFSL

STSGMGVGWIRQPSGKGLEWLAHIWWDDDKYYNPSLKSQLTISKDTSRNQ

VFLKITSVDTADTATYYCSRRPRGTMDAMDYWGQGTSVTVSSGGGGSGGG

GSGGGGSDIVMTQAASSLSASLGDRVTISCRASQDISKYLNWYQQKPDGT

VKLLIYYTSRLHSGVPSRFSGSGSGTDYSLTIRNLEQEDIATYFCQQVYT

LPWTFGGGTKLEIKAAATTTPAPRPPTPAPTIASQPLSLRPEACRPAAGG

AVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYN

ELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID NO: 49 is the nucleotide sequence of the
CAR LTG1563 (LP-CD19-TNFRSF19TM-41BB-CD3zeta):
ATGCTGCTGCTGGTCACCAGCCTGCTGCTGTGCGAGCTCCCTCACCCCGC

CTTTCTGCTTATCCCGGACATTCAGATGACACAGACCACCTCGAGCTTGT

CCGCGTCGCTGGGCGATCGCGTGACCATCTCCTGCCGGGCCTCCCAAGAC

ATTTCAAAGTATCTCAACTGGTACCAGCAGAAGCCGGACGGAACCGTGAA

ACTGCTGATCTACCATACCAGCCGCCTGCACTCCGGCGTGCCGTCCCGCT

TCTCCGGATCGGGTTCCGAACTGACTACTCACTGACTATCTCCAACTTG

GAACAAGAGGACATCGCCACTTACTTCTGTCAACAAGGAAATACCCTTCC

CTACACCTTCGGGGGGGTACCAAGCTGGAGATCACTGGGGCGGAGGCT

CCGGTGGAGGCGGATCCGGCGGTGGAGGGAGCGAAGTCAAGCTGCAGGAA

TCAGGACCAGGACTCGTGCGCCATCCCAGTCCCTGTCGGTGACCTGTAC

TGTCTCCGGAGTCAGCCTCCCCGATTACGGAGTGTCATGGATTAGGCAAC

-continued

```
CCCCAAGAAAAGGGCTGGAATGGCTCGGAGTGATCTGGGGCTCCGAAACC
ACCTACTACAACTCGGCGCTGAAGTCCCGGCTGACCATCATCAAGGACAA
CTCCAAGAGCCAAGTGTTCTTGAAGATGAACAGCTTGCAGACCGACGATA
CCGCAATCTACTACTGTGCCAAGCACTATTACTACGGGGGGTCTTACGCC
ATGGACTACTGGGGACAGGGCACCTCCGTGACTGTGTCGTCCGCGGCCGC
GCCCGCCCCTCGGCCCCCGACTCCTGCCCCGACGATCGCTTCCCAACCTC
TCTCGCTGCGCCCGGAAGCATGCCGGCCCGCCGCCGGTGGCGCTGTCCAC
ACTCGCGGACTGGACTTTGATACCGCACTGGCGGCCGTGATCTGTAGCGC
CCTGGCCACCGTGCTGCTGGCGCTGCTCATCCTTTGCGTGATCTACTGCA
AGCGGCAGCCTAGGCGAAAGAAGCTCCTCTACATTTTCAAGCAACCCTTC
ATGCGCCCCGTGCAAACCACCCAGGAGGAGGATGGATGCTCATGCCGGTT
CCCTGAGGAAGAAGAGGGCGGTTGCGAGCTCAGAGTGAAATTCAGCCGGT
CGGCTGACGCCCCGGCGTACCAGCAGGGCCAGAACCAGCTGTACAATGAG
CTCAACCTGGGGCGCCGCGAAGAGTACGACGTGCTGGACAAGAGGAGAGG
CAGAGATCCGGAAATGGGCGGAAAGCCAAGGCGGAAGAACCCGCAGGAAG
GTCTTTACAACGAACTGCAGAAGGACAAGATGGCCGAGGCCTACTCCGAG
ATTGGGATGAAGGGAGAAAGACGGAGGGGAAAGGGACATGACGGACTTTA
CCAGGGCCTGAGCACTGCCACGAAGGACACCTATGATGCCCTGCACATGC
AGGCGCTGCCGCCTCGG
```

SEQ ID NO: 50 is the amino acid sequence of the CAR LTG1563 (LP-CD19-TNFRSF19TM-41BB-CD3zeta):
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGGGGSGGGGSGGGGSEVKLQE
SGPGLVAPSQSLSVTCTVSGVSLPDYGVSWIRQPPRKGLEWLGVIWGSET
TYYNSALKSRLTIIKDNSKSQVFLKMNSLQTDDTAIYYCAKHYYYGGSYA
MDYWGQGTSVTVSSAAAPAPRPPTPAPTIASQPLSLRPEACRPAAGGAVH
TRGLDFDTALAAVICSALATVLLALLILCVIYCKRQPRRKKLLYIFKQPF
MRPVQTTQEEDGCSCRFPEEEEGGCELRVKFSRSADAPAYQQGQNQLYNE
LNLGRREEYDVLDKRRGRDPEMGGKPRRKNPQEGLYNELQKDKMAEAYSE
IGMKGERRRGKGHDGLYQGLSTATKDTYDALHMQALPPR SEQ ID NO: 51 is the amino acid sequence of the CAR LTG2228 (LP-CD20_CD19-CD8TM-CD28-CD3zeta):
ATGCTCCTTCTCGTGACCTCCCTGCTTCTCTGCGAACTGCCCCATCCTGC
CTTCCTGCTGATTCCCGAGGTGCAGTTGCAACAGTCAGGAGCTGAACTGG
TCAAGCCAGGAGCCAGCGTGAAGATGAGCTGCAAGGCCTCCGGTTACACC
TTCACCTCCTACAACATGCACTGGGTGAAACAGACCCCGGGACAAGGGCT
CGAATGGATTGGCGCCATCTACCCCGGGAATGGCGATACTTCGTACAACC
AGAAGTTCAAGGGAAAGGCCACCCTGACCGCCGACAAGAGCTCCTCCACC
GCGTATATGCAGTTGAGCTCCCTGACCTCCGAGGACTCCGCCGACTACTA
CTGCGCACGGTCCAACTACTATGGAAGCTCGTACTGGTTCTTCGATGTCT
GGGGGGCCGGCACCACTGTGACCGTCAGCTCCGGGGGCGGAGGATCCGGT GGAGGCGGAAGCGGGGGTGGAGGATCCGACATTGTGCTGACTCAGTCCCC
GGCAATCCTGTCGGCCTCACCGGGCGAAAAGGTCACGATGACTTGTAGAG
CGTCGTCCAGCGTGAACTACATGGATTGGTACCAAAAGAAGCCTGGATCG
TCACCCAAGCCTTGGATCTACGCTACATCTAACCTGGCCTCCGGCGTGCC
AGCGCGGTTCAGCGGGTCCGGCTCGGGCACCTCATACTCGCTGACCATCT
CCCGCGTGGAGGCTGAGGACGCCGCGACCTACTACTGCCAGCAGTGGTCC
TTCAACCCGCCGACTTTTGGAGGCGGTACTAAGCTGGAGATCAAAGGAGG
CGGCGGCAGCGGCGGGGGAGGGTCCGGAGGGGGTGGTTCTGGTGGAGGAG
GATCGGGAGGCGGTGGCAGCGACATTCAGATGACTCAGACCACCTCCTCC
CTGTCCGCCTCCCTGGGCGACCGCGTGACCATCTCATGCCGCGCCAGCCA
GGACATCTCGAAGTACCTCAACTGGTACCAGCAGAAGCCCGACGGAACCG
TGAAGCTCCTGATCTACCACACCTCCCGGCTGCACAGCGGAGTGCCGTCT
AGATTCTCGGGTTCGGGGTCGGGAACTGACTACTCCCTTACTATTTCCAA
CCTGGAGCAGGAGGATATTGCCACCTACTTCTGCCAACAAGGAAACACCC
TGCCGTACACTTTTGGCGGGGGAACCAAGCTGGAAATCACTGGCAGCACA
TCCGGTTCCGGGAAGCCCGGCTCCGGAGAGGGCAGCACCAAGGGGGAAGT
CAAGCTGCAGGAATCAGGACCTGGCCTGGTGGCCCCGAGCCAGTCACTGT
CCGTGACTTGTACTGTGTCCGGAGTGTCGCTCCCGGATTACGGAGTGTCC
TGGATCAGGCAGCCACCTCGGAAAGGATTGGAATGGCTCGGAGTCATCTG
GGGTTCCGAAACCACCTATTACAACTCGGCACTGAAATCCAGGCTCACCA
TTATCAAGGATAACTCCAAGTCACAAGTGTTCCTGAAGATGAATAGCCTG
CAGACTGACGACACGGCGATCTACTATTGCGCCAAGCACTACTACTACGG
CGGATCCTACGCTATGGACTACTGGGGCCAGGGGACCAGCGTGACCGTGT
CATCCGCGGCCGCGACTACCACTCCTGCACCACGGCCACCTACCCCAGCC
CCCACCATTGCAAGCCAGCCACTTTCACTGCGCCCCGAAGCGTGTAGACC
AGCTGCTGGAGGAGCCGTGCATACCCGAGGGCTGGACTTCGCCTGTGACA
TCTACATCTGGGCCCCATTGGCTGGAACTTGCGGCGTGCTGCTCTTGTCT
CTGGTCATTACCCTGTACTGCCGGTCGAAGAGGTCCAGACTCTTGCACTC
CGACTACATGAACATGACTCCTAGAAGGCCCGGACCCACTAGAAAGCACT
ACCAGCCGTACGCCCCTCCTCGGGATTTCGCCGCATACCGGTCCAGAGTG
AAGTTCAGCCGCTCAGCCGATGCACCGGCCTACCAGCAGGGACAGAACCA
GCTCTACAACGAGCTCAACCTGGGTCGGCGGGAAGAATATGACGTGCTGG
ACAAACGGCGCGGCAGAGATCCGGAGATGGGGGAAAGCCGAGGAGGAAG
AACCCTCAAGAGGGCCTGTACAACGAACTGCAGAAGGACAAGATGGCGGA
AGCCTACTCCGAGATCGGCATGAAGGGAGAACGCCGAGAGGGAAGGGTC
ATGACGGACTGTACCAGGGCCTGTCAACTGCCACTAAGGACACTTACGAT
GCGCTCCATATGCAAGCTTTGCCCCCGCGG SEQ ID NO: 52 is the amino acid sequence of the CAR LTG2228 (LP-CD20_CD19-CD8TM-CD28-CD3zeta):
MLLLVTSLLLCELPHPAFLLIPEVQLQQSGAELVKPGASVKMSCKASGYT
FTSYNMHWVKQTPGQGLEWIGAIYPGNGDTSYNQKFKGKATLTADKSSST
AYMQLSSLTSEDSADYYCARSNYYGSSYWFFDVWGAGTTVTVSSGGGGSG -continued

GGGSGGGGSDIVLTQSPAILSASPGEKVTMTCRASSSVNYMDWYQKKPGS

SPKPWIYATSNLASGVPARFSGSGSGTSYSLTISRVEAEDAATYYCQQWS

FNPPTFGGGTKLEIKGGGGSGGGGSGGGGSGGGGSGGGGSDIQMTQTTSS

LSASLGDRVTISCRASQDISKYLNWYQQKPDGTVKLLIYHTSRLHSGVPS

RFSGSGSGTDYSLTISNLEQEDIATYFCQQGNTLPYTFGGGTKLEITGST

SGSGKPGSGEGSTKGEVKLQESGPGLVAPSQSLSVTCTVSGVSLPDYGVS

WIRQPPRKGLEWLGVIWGSETTYYNSALKSRLTIIKDNSKSQVFLKMNSL

QTDDTAIYYCAKHYYYGGSYAMDYWGQGTSVTVSSAAATTTPAPRPPTPA

PTIASQPLSLRPEACRPAAGGAVHTRGLDFACDIYIWAPLAGTCGVLLLS

LVITLYCRSKRSRLLHSDYMNMTPRRPGPTRKHYQPYAPPRDFAAYRSRV

KFSRSADAPAYQQGQNQLYNELNLGRREEYDVLDKRRGRDPEMGGKPRRK

NPQEGLYNELQKDKMAEAYSEIGMKGERRRGKGHDGLYQGLSTATKDTYD

ALHMQALPPR

SEQ ID NO: 53 is the amino acid sequence of the Whitlow linker:
GSTSGSGKPGSGEGSTKG SEQ ID NO: 54 is the amino acid sequence of a flexible interchain linker:
GGGGSGGGGSGGGGSGGGGSGGGGS

---

What is claimed is:

1. A method of treating a subject having a CD19+, a CD20+, a CD22+ or a CD19+ and CD20+ lymphoma, the method comprising administering to the subject having the CD19+, the CD20+, the CD22+ or the CD19+ and CD20+ lymphoma a pharmaceutical composition comprising an antitumor effective amount of a population of human T cells,
wherein the population of human T-cells are autologous to the subject, and wherein each cell of the population of human T-cells comprises at least one multi-cistronic vector, each of the at least one multi-cistronic vector comprises a promoter operably linked to a multi-cistronic nucleic acid sequence encoding two or more functional CARs, wherein at least one of the two or more functional CARs comprises two non-identical extracellular antigen binding domains, a transmembrane domain, and one or more non-identical intracellular signaling motifs,
and comprises an amino acid sequence selected from the group consisting of SEQ ID NO: 10 and SEQ ID NO: 52, and
the combination of the vectors results in the expression of at least two non-identical extracellular binding domains directed to the CD19+, the CD20+, the CD22+ or the CD19+ and CD20+ lymphoma thereby treating the subject.

2. The method of claim 1, wherein the population of human T-cells are infused directly into the subject.

3. The method of claim 1, wherein the population of human T-cells express activation or memory-associated surface markers.

4. The method of claim 1, wherein the lymphoma is mantle cell lymphoma, non-Hodgkin's lymphoma or Hodgkin's lymphoma.

5. A method of treating a subject having a lymphoma, the method comprising administering to the subject having the lymphoma a pharmaceutical composition comprising an antitumor effective amount of a population of human T-cells autologous to the subject,
wherein each cell of the population of human T-cells autologous to the subject comprises at least one multi-cistronic vector, wherein the at least one multi-cistronic vector comprises a promoter operably linked to a multi-cistronic nucleic acid sequence encoding two or more functional CARs, wherein at least one of the two or more functional CARs comprises two non-identical extracellular antigen binding domains, a transmembrane domain, and one or more non-identical intracellular signaling motifs, and comprises non-identical amino acid sequences that are independently selected from the group consisting of the amino acid sequences of SEQ ID NO: 4; SEQ ID NO: 10; SEQ ID NO: 22; SEQ ID NO: 24; SEQ ID NO: 26; SEQ ID NO: 30; SEQ ID NO: 32; SEQ ID NO: 34; SEQ ID NO: 36; SEQ ID NO: 44; SEQ ID NO: 48; SEQ ID NO: 50; and SEQ ID NO: 52, and the combination of the vectors results in the expression of at least two non-identical extracellular binding domains, thereby treating the lymphoma in the subject.

6. The method of claim 5, wherein the population of human T-cells are infused directly into the subject.

7. The method of claim 5, wherein the population of human T-cells express activation or memory-associated surface markers.

8. The method of claim 5, wherein the lymphoma is mantle cell lymphoma, non-Hodgkin's lymphoma or Hodgkin's lymphoma.

* * * * *

SEQUENCE LISTING

<160> NUMBER OF SEQ ID NOS: 54

<210> SEQ ID NO 1
<211> LENGTH: 729
<212> TYPE: DNA
<213> ORGANISM: Artificial Sequence
<220> FEATURE:
<223> OTHER INFORMATION: CD20-reactive scFv binding domain

<400> SEQUENCE: 1

```
gaggtgcagt tgcaacagtc aggagctgaa ctggtcaagc caggagccag cgtgaagatg      60
agctgcaagg cctccggtta caccttcacc tcctacaaca tgcactgggt gaaacagacc     120
ccgggacaag ggctcgaatg gattggcgcc atctaccccg gaatggcga tacttcgtac     180 aaccagaagt tcaaggaaa ggccaccctg accgccgaca gagctcctc caccgcgtat     240 atgcagttga gctccctgac ctccgaggac tccgccgact actactgcgc acggtccaac     300
tactatggaa gctcgtactg gttcttcgat gtctggggg ccggcaccac tgtgaccgtc     360
agctccgggg gcggaggatc cggtggaggc ggaagcgggg gtggaggatc cgacattgtg     420
ctgactcagt ccccggcaat cctgtcggcc tcaccgggcg aaaaggtcac gatgacttgt     480
agagcgtcgt ccagcgtgaa ctacatggat tggtaccaaa agaagcctgg atcgtcaccc     540
aagccttgga tctacgctac atctaacctg gcctccggcg tgccagcgcg gttcagcggg     600
tccggctcgg gcacctcata ctcgctgacc atctcccgcg tggaggctga ggacgccgcg     660
acctactact gccagcagtg gtccttcaac ccgccgactt ttggaggcgg tactaagctg     720
gagatcaaa                                                              729
```

<210> SEQ ID NO 2
<211> LENGTH: 243
<212> TYPE: PRT
<213> ORGANISM: Artificial Sequence
<220> FEATURE:
<223> OTHER INFORMATION: CD20-reactive scFv binding domain

<400> SEQUENCE: 2

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
```

| | | | | | | 50 | | | 55 | | | | 60 | | |
|---|---|---|---|---|---|---|---|---|---|---|---|---|---|---|---|

Lys Gly Lys Ala Thr Leu Thr Ala Asp Lys Ser Ser Thr Ala Tyr
65                       70                    75                    80

Met Gln Leu Ser Ser Leu Thr Ser Glu Asp Ser Ala Asp Tyr Tyr Cys
                    85                    90                    95

Ala Arg Ser Asn Tyr Tyr Gly Ser Ser Tyr Trp Phe Phe Asp Val Trp
              100                    105                    110

Gly Ala Gly Thr Thr Val Thr Val Ser Ser Gly Gly Gly Gly Ser Gly
              115                    120                    125

Gly Gly Gly Ser Gly Gly Gly Ser Asp Ile Val Leu Thr Gln Ser
        130                    135                    140

Pro Ala Ile Leu Ser Ala Ser Pro Gly Glu Lys Val Thr Met Thr Cys
145                     150                    155                    160

Arg Ala Ser Ser Ser Val Asn Tyr Met Asp Trp Tyr Gln Lys Lys Pro
              165                    170                    175

Gly Ser Ser Pro Lys Pro Trp Ile Tyr Ala Thr Ser Asn Leu Ala Ser
                    180                    185                    190

Gly Val Pro Ala Arg Phe Ser Gly Ser Gly Ser Gly Thr Ser Tyr Ser
              195                    200                    205

Leu Thr Ile Ser Arg Val Glu Ala Glu Asp Ala Ala Thr Tyr Tyr Cys
        210                    215                    220

Gln Gln Trp Ser Phe Asn Pro Pro Thr Phe Gly Gly Gly Thr Lys Leu
225                     230                    235                    240

Glu Ile Lys

<210> SEQ ID NO 3
<211> LENGTH: 1473
<212> TYPE: DNA
<213> ORGANISM: Artificial Sequence
<220> FEATURE:
<223> OTHER INFORMATION: LP-1495-CD8 TM-41BB-CD3zeta

<400> SEQUENCE: 3

```
atgctccttc tcgtgacctc cctgcttctc tgcgaactgc cccatcctgc cttcctgctg      60
attcccgagg tgcagttgca acagtcagga gctgaactgg tcaagccagg agccagcgtg     120
aagatgagct gcaaggcctc cggttacacc ttcacctcct acaacatgca ctgggtgaaa     180
cagaccccgg acaagggct cgaatggatt ggcgccatct accccgggaa tggcgatact     240
tcgtacaacc agaagttcaa gggaaaggcc accctgaccg ccgacaagag ctcctccacc     300
gcgtatatgc agttgagctc cctgacctcc gaggactccg ccgactacta ctgcgcacgg     360
tccaactact atggaagctc gtactggttc ttcgatgtct ggggggccgg caccactgtg     420
accgtcagct ccgggggcgg aggatccggt ggaggcggaa gcggggtgg aggatccgac     480
attgtgctga ctcagtcccc ggcaatcctg tcggcctcac cgggcgaaaa ggtcacgatg     540
acttgtagag cgtcgtccag cgtgaactac atggattggt accaaaagaa gcctggatcg     600
tcacccaagc cttggatcta cgctacatct aacctggcct ccggcgtgcc agcgcggttc     660
agcgggtccg gctcgggcac ctcatactcg ctgaccatct cccgcgtgga ggctgaggac     720
gccgcgacct actactgcca gcagtggtcc ttcaacccgc cgacttttgg aggcggtact     780
aagctggaga tcaaagcggc cgcaactacc accctgccc tcggccgcc gactccggcc     840
ccaaccatcg caagccaacc cctctccttg cgccccgaag cttgccgcc ggccgcgggt     900
ggagccgtgc ataccgggg gctggacttt gcctgcgata tctacatttg gccccgctg     960
```

```
gccggcacttt gcggcgtgct cctgctgtcg ctggtcatca cccttttactg caagaggggc    1020 cggaagaagc tgctttacat cttcaagcag ccgttcatgc ggcccgtgca gacgactcag    1080
gaagaggacg gatgctcgtg cagattccct gaggaggaag agggggggatg cgaactgcgc    1140 gtcaagttct cacggtccgc cgacgccccc gcatatcaac agggccagaa tcagctctac    1200
aacgagctga acctgggaag gagagaggag tacgacgtgc tggacaagcg acgcggacgc    1260
gacccggaga tggggggggaa ccacggcgg aaaaaccctc aggaaggact gtacaacgaa    1320
ctccagaaag acaagatggc ggaagcctac tcagaaatcg ggatgaaggg agagcggagg    1380
aggggaaagg gtcacgacgg gctgtaccag ggactgagca ccgccactaa ggataccctac    1440 gatgccttgc atatgcaagc actcccaccc cgg                                 1473
```

<210> SEQ ID NO 4
<211> LENGTH: 491
<212> TYPE: PRT
<213> ORGANISM: Artificial Sequence
<220> FEATURE:
<223> OTHER INFORMATION: LP-1495-CD8 TM-41BB-CD3zeta

<400> SEQUENCE: 4

```
Met Leu Leu Leu Val Thr Ser Leu Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Ser Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Ala Ala Ala Thr Thr Thr Pro
            260                 265                 270
```

```
Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490

<210> SEQ ID NO 5
<211> LENGTH: 66
<212> TYPE: DNA
<213> ORGANISM: Artificial Sequence
<220> FEATURE:
<223> OTHER INFORMATION: leader/signal peptide sequence

<400> SEQUENCE: 5
atgctgctgc tggtgaccag cctgctgctg tgcgaactgc cgcatccggc gtttctgctg     60
attccg                                                               66

<210> SEQ ID NO 6
<211> LENGTH: 22
<212> TYPE: PRT
<213> ORGANISM: Artificial Sequence
<220> FEATURE:
<223> OTHER INFORMATION: leader/signal peptide sequence

<400> SEQUENCE: 6

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 7
<211> LENGTH: 747
<212> TYPE: DNA
<213> ORGANISM: Artificial Sequence
<220> FEATURE:
<223> OTHER INFORMATION: CD22-reactive scFv binding domain
```

<400> SEQUENCE: 7

```
caggtacagc tccagcagag tggcccaggg ctcgtgaagc caagccagac gctgtccctg    60
acttgtgcaa tttcagggga ttcagtttca tcaaatagcg cggcgtggaa ttggattcga   120
caatctcctt cccgagggtt ggaatggctt ggacgaacat attacagatc caaatggtat   180
aacgactatg cggtatcagt aaagtcaaga ataaccatta accccgacac aagcaagaac   240
caattctctt tgcagcttaa ctctgtcacg ccagaagaca cggcagtcta ttattgcgct   300
cgcgaggtaa cgggtgacct ggaagacgct tttgacattt gggggcaggg tacgatggtg   360
acagtcagtt caggggcgg tgggagtggg ggaggggta gcgggggggg agggtcagac   420
attcagatga cccagtcccc ttcatccttg tctgcctccg tcggtgacag ggtgacaata   480
acatgcagag caagccaaac aatctggagc tatctcaact ggtaccagca gcgaccagga   540
aaagcgccaa acctgctgat ttacgctgct tcctcccctcc aatcaggcgt gcctagtaga   600
tttagcggta ggggctccgg caccgatttt acgctcacta taagctctct tcaagcagaa   660
gattttgcga cttattactg ccagcagtcc tatagtatac ctcagacttt cggacagggt   720
accaagttgg agattaaggc ggccgca                                      747
```

<210> SEQ ID NO 8
<211> LENGTH: 249
<212> TYPE: PRT
<213> ORGANISM: Artificial Sequence
<220> FEATURE:
<223> OTHER INFORMATION: CD22-reactive scFv binding domain

<400> SEQUENCE: 8

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Thr Ile Trp Ser Tyr Leu Asn Trp Tyr Gln
                165                 170                 175

Gln Arg Pro Gly Lys Ala Pro Asn Leu Leu Ile Tyr Ala Ala Ser Ser
            180                 185                 190

Leu Gln Ser Gly Val Pro Ser Arg Phe Ser Gly Arg Gly Ser Gly Thr
        195                 200                 205

Asp Phe Thr Leu Thr Ile Ser Ser Leu Gln Ala Glu Asp Phe Ala Thr
```

```
            210                 215                 220
Tyr Tyr Cys Gln Gln Ser Tyr Ser Ile Pro Gln Thr Phe Gly Gln Gly
225                 230                 235                 240

Thr Lys Leu Glu Ile Lys Ala Ala Ala
            245

<210> SEQ ID NO 9
<211> LENGTH: 1482
<212> TYPE: DNA
<213> ORGANISM: Artificial Sequence
<220> FEATURE:
<223> OTHER INFORMATION: LP-2200-CD8 TM-41BB-CD3zeta

<400> SEQUENCE: 9
atgcttcttt tggtgacttc ccttttgctg tgcgagttgc cacacccgc  cttcctgctt      60 attccccagg tacagctcca gcagagtggg ccagggctcg tgaagccaag ccagacgctg     120
tccctgactt gtgcaatttc aggggattca gtttcatcaa atagcgcggc gtggaattgg     180
attcgacaat ctccttcccg agggttggaa tggcttggac gaacatatta cagatccaaa     240
tggtataacg actatgcggt atcagtaaag tcaagaataa ccattaaccc cgacacaagc     300
aagaaccaat tctctttgca gcttaactct gtcacgccag aagacacggc agtctattat     360
tgcgctcgcg aggtaacggg tgacctggaa gacgcttttg acatttgggg cagggtacg      420 atggtgacag tcagttcagg gggcggtggg agtgggggag gggtagcgg  gggggaggg      480 tcagacattc agatgaccca gtccccttca tccttgtctg cctccgtcgg tgacagggtg     540
acaataacat gcagagcaag ccaaacaatc tggagctatc tcaactggta ccagcagcga     600
ccaggaaaag cgccaaacct gctgattac gctgcttcct ccctccaatc aggcgtgcct      660
agtagattta gcgtaggggg ctccggcacc gattttacgc tcactataag ctctcttcaa     720
gcagaagatt ttgcgactta ttactgccag cagtcctata gtatacctca gactttcgga    780
cagggtacca agttggagat taaggcggcc gcaactacca cccctgcccc tcggccgccg     840
actccggccc caaccatcgc aagccaaccc ctctccttgc gccccgaagc ttgccgcccg     900
gccgcgggtg gagccgtgca tacccggggg ctggactttg cctgcgatat ctacatttgg     960
gccccgctgg ccggcacttg cggcgtgctc ctgctgtcgc tggtcatcac ccttactgc      1020 aagaggggcc ggaagaagct gctttacatc ttcaagcagc cgttcatgcg gcccgtgcag    1080
acgactcagg aagaggacgg atgctcgtgc agattccctg aggaggaaga ggggggatgc    1140
gaactgcgcg tcaagttctc acggtccgcc gacgccccg catatcaaca gggccagaat     1200
cagctctaca acgagctgaa cctgggaagg agagaggagt acgacgtgct ggacaagcga    1260
cgcggacgcg acccggagat ggggggaaa ccacggcgga aaaccctca ggaaggactg      1320 tacaacgaac tccagaaaga caagatggcg gaagcctact cagaaatcgg gatgaaggga    1380
gagcggagga gggaaagggg tcacgacggg ctgtaccagg gactgagcac cgccactaag    1440 gataccctacg atgccttgca tatgcaagca ctcccacccc gg                     1482

<210> SEQ ID NO 10
<211> LENGTH: 494
<212> TYPE: PRT
<213> ORGANISM: Artificial Sequence
<220> FEATURE:
<223> OTHER INFORMATION: LP-2200-CD8 TM-41BB-CD3zeta

<400> SEQUENCE: 10

Met Leu Leu Leu Val Thr Ser Leu Leu Leu Cys Glu Leu Pro His Pro
```

-continued

```
  1               5                  10                 15
Ala Phe Leu Leu Ile Pro Gln Val Gln Leu Gln Gln Ser Gly Pro Gly
                20                 25                 30

Leu Val Lys Pro Ser Gln Thr Leu Ser Leu Thr Cys Ala Ile Ser Gly
                35                 40                 45

Asp Ser Val Ser Ser Asn Ser Ala Ala Trp Asn Trp Ile Arg Gln Ser
 50                     55                     60

Pro Ser Arg Gly Leu Glu Trp Leu Gly Arg Thr Tyr Tyr Arg Ser Lys
 65                 70                 75                     80

Trp Tyr Asn Asp Tyr Ala Val Ser Val Lys Ser Arg Ile Thr Ile Asn
                85                 90                 95

Pro Asp Thr Ser Lys Asn Gln Phe Ser Leu Gln Leu Asn Ser Val Thr
                100                105                110

Pro Glu Asp Thr Ala Val Tyr Tyr Cys Ala Arg Glu Val Thr Gly Asp
                115                120                125

Leu Glu Asp Ala Phe Asp Ile Trp Gly Gln Gly Thr Met Val Thr Val
 130                    135                    140

Ser Ser Gly Gly Gly Gly Ser Gly Gly Gly Gly Ser Gly Gly Gly Gly
 145                    150                    155                160

Ser Asp Ile Gln Met Thr Gln Ser Pro Ser Ser Leu Ser Ala Ser Val
                165                170                175

Gly Asp Arg Val Thr Ile Thr Cys Arg Ala Ser Gln Thr Ile Trp Ser
                180                185                190

Tyr Leu Asn Trp Tyr Gln Gln Arg Pro Gly Lys Ala Pro Asn Leu Leu
                195                200                205

Ile Tyr Ala Ala Ser Ser Leu Gln Ser Gly Val Pro Ser Arg Phe Ser
 210                    215                    220

Gly Arg Gly Ser Gly Thr Asp Phe Thr Leu Thr Ile Ser Ser Leu Gln
 225                    230                    235                240

Ala Glu Asp Phe Ala Thr Tyr Tyr Cys Gln Gln Ser Tyr Ser Ile Pro
                245                250                255

Gln Thr Phe Gly Gln Gly Thr Lys Leu Glu Ile Lys Ala Ala Ala Thr
                260                265                270

Thr Thr Pro Ala Pro Arg Pro Pro Thr Pro Ala Pro Thr Ile Ala Ser
                275                280                285

Gln Pro Leu Ser Leu Arg Pro Glu Ala Cys Arg Pro Ala Ala Gly Gly
                290                295                300

Ala Val His Thr Arg Gly Leu Asp Phe Ala Cys Asp Ile Tyr Ile Trp
 305                    310                    315                320

Ala Pro Leu Ala Gly Thr Cys Gly Val Leu Leu Leu Ser Leu Val Ile
                325                330                335

Thr Leu Tyr Cys Lys Arg Gly Arg Lys Lys Leu Leu Tyr Ile Phe Lys
                340                345                350

Gln Pro Phe Met Arg Pro Val Gln Thr Thr Gln Glu Glu Asp Gly Cys
                355                360                365

Ser Cys Arg Phe Pro Glu Glu Glu Gly Gly Cys Glu Leu Arg Val
 370                    375                    380

Lys Phe Ser Arg Ser Ala Asp Ala Pro Ala Tyr Gln Gln Gly Gln Asn
 385                    390                    395                400

Gln Leu Tyr Asn Glu Leu Asn Leu Gly Arg Arg Glu Glu Tyr Asp Val
                405                410                415

Leu Asp Lys Arg Arg Gly Arg Asp Pro Glu Met Gly Gly Lys Pro Arg
                420                425                430
```

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 11
<211> LENGTH: 72
<212> TYPE: DNA
<213> ORGANISM: Homo sapiens

<400> SEQUENCE: 11
atctacatct gggcgccctt ggccgggact tgtggggtcc ttctcctgtc actggttatc     60 acccttact gc                                                         72

<210> SEQ ID NO 12
<211> LENGTH: 22
<212> TYPE: PRT
<213> ORGANISM: Homo sapiens

<400> SEQUENCE: 12

Ile Trp Ala Pro Leu Ala Gly Thr Cys Gly Val Leu Leu Leu Ser Leu
1               5                   10                  15

Val Ile Thr Leu Tyr Cys
            20

<210> SEQ ID NO 13
<211> LENGTH: 141
<212> TYPE: DNA
<213> ORGANISM: Homo sapiens

<400> SEQUENCE: 13
accacgacgc cagcgccgcg accaccaaca ccggcgccca ccatcgcgtc gcagcccctg     60
tccctgcgcc cagaggcgtg ccggccagcg gcgggggggcg cagtgcacac gagggggctg    120
gactttgcct gcgatatcta c                                              141

<210> SEQ ID NO 14
<211> LENGTH: 47
<212> TYPE: PRT
<213> ORGANISM: Homo sapiens

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
            35                  40                  45

<210> SEQ ID NO 15
<211> LENGTH: 69
<212> TYPE: PRT
<213> ORGANISM: Homo sapiens

<400> SEQUENCE: 15

Thr Thr Thr Pro Ala Pro Arg Pro Pro Thr Pro Ala Pro Thr Ile Ala

```
                1               5                  10                 15
Ser Gln Pro Leu Ser Leu Arg Pro Glu Ala Cys Arg Pro Ala Ala Gly
                    20                 25                 30

Gly Ala Val His Thr Arg Gly Leu Asp Phe Ala Cys Asp Ile Tyr Ile
            35                 40                 45

Trp Ala Pro Leu Ala Gly Thr Cys Gly Val Leu Leu Leu Ser Leu Val
    50                 55                 60

Ile Thr Leu Tyr Cys
65
```

<210> SEQ ID NO 16
<211> LENGTH: 106
<212> TYPE: PRT
<213> ORGANISM: Homo sapiens

<400> SEQUENCE: 16

```
Gly Gln Pro Lys Ala Ala Pro Ser Val Thr Leu Phe Pro Pro Ser Ser
1               5                  10                 15

Glu Glu Leu Gln Ala Asn Lys Ala Thr Leu Val Cys Leu Ile Ser Asp
                    20                 25                 30

Phe Tyr Pro Gly Ala Val Thr Val Ala Trp Lys Ala Asp Ser Ser Pro
            35                 40                 45

Val Lys Ala Gly Val Glu Thr Thr Thr Pro Ser Lys Gln Ser Asn Asn
    50                 55                 60

Lys Tyr Ala Ala Ser Ser Tyr Leu Ser Leu Thr Pro Glu Gln Trp Lys
65                 70                  75                 80

Ser His Arg Ser Tyr Ser Cys Gln Val Thr His Glu Gly Ser Thr Val
                85                 90                 95

Glu Lys Thr Val Ala Pro Thr Glu Cys Ser
            100                105
```

<210> SEQ ID NO 17
<211> LENGTH: 126
<212> TYPE: DNA
<213> ORGANISM: Homo sapiens

<400> SEQUENCE: 17

```
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126
```

<210> SEQ ID NO 18
<211> LENGTH: 42
<212> TYPE: PRT
<213> ORGANISM: Homo sapiens

<400> SEQUENCE: 18

```
Lys Arg Gly Arg Lys Lys Leu Leu Tyr Ile Phe Lys Gln Pro Phe Met
1               5                  10                 15

Arg Pro Val Gln Thr Thr Gln Glu Glu Asp Gly Cys Ser Cys Arg Phe
                    20                 25                 30

Pro Glu Glu Glu Glu Gly Gly Cys Glu Leu
            35                 40
```

<210> SEQ ID NO 19
<211> LENGTH: 336
<212> TYPE: DNA
<213> ORGANISM: Artificial Sequence

```
<220> FEATURE:
<223> OTHER INFORMATION: signaling domain of CD3-zeta

<400> SEQUENCE: 19
agagtgaagt tcagcaggag cgcagacgcc ccgcgtaca agcagggcca gaaccagctc      60
tataacgagc tcaatctagg acgaagagag gagtacgatg ttttggacaa gagacgtggc    120
cgggaccctg agatggggga aaagccgaga aggaagaacc ctcaggaagg cctgtacaat    180
gaactgcaga aagataagat ggcggaggcc tacagtgaga ttgggatgaa aggcgagcgc    240 cggagggggca aggggcacga tggccttttac cagggtctca gtacagccac caaggacacc    300
tacgacgccc ttcacatgca ggccctgccc cctcgc                              336

<210> SEQ ID NO 20
<211> LENGTH: 112
<212> TYPE: PRT
<213> ORGANISM: Homo sapiens

<400> SEQUENCE: 20

Arg Val Lys Phe Ser Arg Ser Ala Asp Ala Pro Ala Tyr Lys Gln Gly
 1               5                  10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
    65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 21
<211> LENGTH: 1467
<212> TYPE: DNA
<213> ORGANISM: Artificial Sequence
<220> FEATURE:
<223> OTHER INFORMATION: LP-CD19binder-CD8linker-CD4tm-4-1BB-CD3-zeta

<400> SEQUENCE: 21
atgctgctgc tggtgaccag cctgctgctg tgcgaactgc cgcatccggc gtttctgctg      60
attccggata ttcagatgac ccagaccacc agcagcctga gcgcgagcct gggcgatcgc    120
gtgaccatta gctgccgcgc gagccaggat attagcaaat atctgaactg gtatcagcag    180
aaaccggatg gcaccgtgaa actgctgatt tatcatacca gccgcctgca tagcggcgtg    240
ccgagccgct ttagcggcag cggcagcggc accgattata gcctgaccat tagcaacctg    300
gaacaggaag atattgcgac ctatttttgc cagcagggca cacccctgcc gtatacccttt    360 ggcggcggca ccaaactgga aattaccggc ggcggcggca gcggcggcgg cggcagcggc    420
ggcggcggca gcgaagtgaa actgcaggaa agcggcccgg gcctggtggc gccgagccag    480
agcctgagcg tgacctgcac cgtgagcggc gtgagcctgc cggattatgg cgtgagctgg    540
attcgccagc cgccgcgcaa aggcctggaa tggctgggcg tgatttgggg cagcgaaacc    600
acctattata acagcgcgct gaaaagccgc ctgaccatta ttaaagataa cagcaaaagc    660
caggtgtttc tgaaaatgaa cagcctgcag accgatgata ccgcgattta ttattgcgcg    720
```

-continued

```
aaacattatt attatggcgg cagctatgcg atggattatt ggggccaggg caccagcgtg    780
accgtgagca gcgcggcggc gccggcgccg cgcccgccga ccccggcgcc gaccattgcg    840
agccagccgc tgagcctgcg cccggaagcg tgccgcccgg cggcgggcgg cgcggtgcat    900
acccgcggcc tggattttgt gcagccgatg gcgctgattg tgctgggcgg cgtggcgggc    960
ctgctgctgt ttattggcct gggcattttt ttttgcgtgc gctgccgccc gcgccgcaaa   1020
aaactgctgt atattttaa acagccgttt atgcgcccgg tgcagaccac ccaggaagaa    1080
gatggctgca gctgccgctt ccggaagaa gaagaaggcg gctgcgaact gcgcgtgaaa    1140
tttagccgca gcgcggatgc gccggcgtat cagcagggcc agaaccagct gtataacgaa    1200
ctgaacctgg gccgccgcga agaatatgat gtgctggata acgccgcgg ccgcgatccg    1260 gaaatgggcg gcaaaccgcg ccgcaaaaac ccgcaggaag gcctgtataa cgaactgcag    1320
aaagataaaa tggcggaagc gtatagcgaa attggcatga aaggcgaacg ccgccgcggc    1380
aaaggccatg atggcctgta tcagggcctg agcaccgcga ccaaagatac ctatgatgcg    1440
ctgcatatgc aggcgctgcc gccgcgc                                       1467
```

<210> SEQ ID NO 22
<211> LENGTH: 489
<212> TYPE: PRT
<213> ORGANISM: Artificial Sequence
<220> FEATURE:
<223> OTHER INFORMATION: LP-CD19binder-CD8linker-CD4tm-4-1BB-CD3-zeta

<400> SEQUENCE: 22

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220
```

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
            245                 250                 255

Gly Thr Ser Val Thr Val Ser Ser Ala Ala Pro Ala Pro Arg Pro
        260                 265                 270

Pro Thr Pro Ala Pro Thr Ile Ala Ser Gln Pro Leu Ser Leu Arg Pro
    275                 280                 285

Glu Ala Cys Arg Pro Ala Ala Gly Gly Ala Val His Thr Arg Gly Leu
    290                 295                 300

Asp Phe Val Gln Pro Met Ala Leu Ile Val Leu Gly Gly Val Ala Gly
305                 310                 315                 320

Leu Leu Leu Phe Ile Gly Leu Gly Ile Phe Phe Cys Val Arg Cys Arg
            325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
    355                 360                 365

Glu Glu Glu Glu Gly Gly Cys Glu Leu Arg Val Lys Phe Ser Arg Ser
370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
            405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
            485

<210> SEQ ID NO 23
<211> LENGTH: 1548
<212> TYPE: DNA
<213> ORGANISM: Artificial Sequence
<220> FEATURE:
<223> OTHER INFORMATION: CD20_19-reactive scFv binding domain

<400> SEQUENCE: 23
gaggtgcagt tgcaacagtc aggagctgaa ctggtcaagc caggagccag cgtgaagatg      60
agctgcaagg cctccggtta caccttcacc tcctacaaca tgcactgggt gaaacagacc     120
ccgggacaag gctcgaatg gattggcgcc atctacccg ggaatggcga tacttcgtac      180
aaccagaagt tcaagggaaa ggccaccctg accgccgaca gagctcctc caccgcgtat     240 atgcagttga gctccctgac ctccgaggac tccgccgact actactgcgc acggtccaac     300
tactatggaa gctcgtactg gttcttcgat gtctgggggg ccggcaccac tgtgaccgtc     360
agctccgggg gcggaggatc cggtggaggc ggaagcgggg gtggaggatc cgacattgtg     420
ctgactcagt ccccgcaat cctgtcggcc tcaccgggcg aaaaggtcac gatgacttgt     480
agagcgtcgt ccagcgtgaa ctacatggat tggtaccaaa agaagcctgg atcgtcaccc     540

-continued

```
aagccttgga tctacgctac atctaacctg gcctccggcg tgccagcgcg gttcagcggg    600
tccggctcgg gcacctcata ctcgctgacc atctcccgcg tggaggctga ggacgccgcg    660
acctactact gccagcagtg gtccttcaac ccgccgactt ttggaggcgg tactaagctg    720
gagatcaaag gaggcggcgg cagcggcggg ggagggtccg gagggggtgg ttctggtgga    780
ggaggatcgg gaggcggtgg cagcgacatt cagatgactc agaccacctc ctccctgtcc    840
gcctccctgg gcgaccgcgt gaccatctca tgccgcgcca gccaggacat tcgaagtac     900 ctcaactggt accagcagaa gcccgacgga accgtgaagc tcctgatcta ccacacctcc    960
cggctgcaca gcggagtgcc gtctagattc tcgggttcgg ggtcgggaac tgactactcc   1020
cttactattt ccaacctgga gcaggaggat attgccacct acttctgcca acaaggaaac   1080
accctgccgt acacttttgg cgggggaacc aagctggaaa tcactggcag cacatccggt   1140
tccgggaagc ccggctccgg agagggcagc accaagggg aagtcaagct gcaggaatca    1200
ggacctggcc tggtggcccc gagccagtca ctgtccgtga cttgtactgt gtccggagtg   1260
tcgctcccgg attacggagt gtcctggatc aggcagccac ctcggaaagg attggaatgg   1320
ctcggagtca tctggggttc cgaaaccacc tattacaact cggcactgaa atccaggctc   1380
accattatca aggataactc caagtcacaa gtgttcctga agatgaatag cctgcagact   1440
gacgacacgg cgatctacta ttgcgccaag cactactact acggcggatc ctacgctatg   1500
gactactggg gccaggggac cagcgtgacc gtgtcatccg cggccgca              1548
```

<210> SEQ ID NO 24
<211> LENGTH: 516
<212> TYPE: PRT
<213> ORGANISM: Artificial Sequence
<220> FEATURE:
<223> OTHER INFORMATION: CD20_19-reactive scFv binding domain

<400> SEQUENCE: 24

```
Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Ser Asp Ile Val Leu Thr Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Asn Tyr Met Asp Trp Tyr Gln Lys Lys Pro
                165                 170                 175

Gly Ser Ser Pro Lys Pro Trp Ile Tyr Ala Thr Ser Asn Leu Ala Ser
            180                 185                 190
```

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
        210                 215                 220

Gln Gln Trp Ser Phe Asn Pro Pro Thr Phe Gly Gly Gly Thr Lys Leu
225                 230                 235                 240

Glu Ile Lys Gly Gly Gly Gly Ser Gly Gly Gly Gly Ser Gly Gly Gly
                245                 250                 255

Gly Ser Gly Gly Gly Gly Ser Gly Gly Gly Gly Ser Asp Ile Gln Met
                260                 265                 270

Thr Gln Thr Thr Ser Ser Leu Ser Ala Ser Leu Gly Asp Arg Val Thr
        275                 280                 285

Ile Ser Cys Arg Ala Ser Gln Asp Ile Ser Lys Tyr Leu Asn Trp Tyr
        290                 295                 300

Gln Gln Lys Pro Asp Gly Thr Val Lys Leu Leu Ile Tyr His Thr Ser
305                 310                 315                 320

Arg Leu His Ser Gly Val Pro Ser Arg Phe Ser Gly Ser Gly Ser Gly
                325                 330                 335

Thr Asp Tyr Ser Leu Thr Ile Ser Asn Leu Glu Gln Glu Asp Ile Ala
        340                 345                 350

Thr Tyr Phe Cys Gln Gln Gly Asn Thr Leu Pro Tyr Thr Phe Gly Gly
        355                 360                 365

Gly Thr Lys Leu Glu Ile Thr Gly Ser Thr Ser Gly Ser Gly Lys Pro
370                 375                 380

Gly Ser Gly Glu Gly Ser Thr Lys Gly Glu Val Lys Leu Gln Glu Ser
385                 390                 395                 400

Gly Pro Gly Leu Val Ala Pro Ser Gln Ser Leu Ser Val Thr Cys Thr
                405                 410                 415

Val Ser Gly Val Ser Leu Pro Asp Tyr Gly Val Ser Trp Ile Arg Gln
        420                 425                 430

Pro Pro Arg Lys Gly Leu Glu Trp Leu Gly Val Ile Trp Gly Ser Glu
        435                 440                 445

Thr Thr Tyr Tyr Asn Ser Ala Leu Lys Ser Arg Leu Thr Ile Ile Lys
        450                 455                 460

Asp Asn Ser Lys Ser Gln Val Phe Leu Lys Met Asn Ser Leu Gln Thr
465                 470                 475                 480

Asp Asp Thr Ala Ile Tyr Tyr Cys Ala Lys His Tyr Tyr Tyr Gly Gly
                485                 490                 495

Ser Tyr Ala Met Asp Tyr Trp Gly Gln Gly Thr Ser Val Thr Val Ser
        500                 505                 510

Ser Ala Ala Ala
        515

<210> SEQ ID NO 25
<211> LENGTH: 2283
<212> TYPE: DNA
<213> ORGANISM: Artificial Sequence
<220> FEATURE:
<223> OTHER INFORMATION: LP-CD20 VH-(GGGGS)3-CD20 VL-(GGGGS)5-CD19VL-
      Whitlow linker-CD19 VH-CD8 hinge+TM-41BB-CD3zeta

<400> SEQUENCE: 25
atgctccttc tcgtgacctc cctgcttctc tgcgaactgc ccatcctgc cttcctgctg    60 attcccgagg tgcagttgca acagtcagga gctgaactgg tcaagccagg agccagcgtg   120

```
aagatgagct gcaaggcctc cggttacacc ttcacctcct acaacatgca ctgggtgaaa      180
cagaccccgg gacaagggct cgaatggatt ggcgccatct accccgggaa tggcgatact      240
tcgtacaacc agaagttcaa gggaaaggcc accctgaccg ccgacaagag ctcctccacc      300
gcgtatatgc agttgagctc cctgacctcc gaggactccg ccgactacta ctgcgcacgg      360
tccaactact atggaagctc gtactggttc ttcgatgtct ggggggccgg caccactgtg      420
accgtcagct ccggggggcgg aggatccggt ggaggcggaa gcggggggtgg aggatccgac      480 attgtgctga ctcagtcccc ggcaatcctg tcggcctcac cgggcgaaaa ggtcacgatg      540
acttgtagag cgtcgtccag cgtgaactac atggattggt accaaaagaa gcctggatcg      600
tcacccaagc cttggatcta cgctacatct aacctggcct ccggcgtgcc agcgcggttc      660
agcgggtccg gctcgggcac ctcatactcg ctgaccatct cccgcgtgga ggctgaggac      720
gccgcgacct actactgcca gcagtggtcc ttcaacccgc cgacttttgg aggcggtact      780
aagctggaga tcaaaggagg cggcggcagc ggcgggggag gtccggagg gggtggttct      840 ggtggaggag atcgggagg cggtggcagc gacattcaga tgactcagac cacctcctcc      900
ctgtccgcct ccctgggcga ccgcgtgacc atctcatgcc gcgccagcca ggacatctcg      960
aagtacctca actggtacca gcagaagccc gacggaaccg tgaagctcct gatctaccac     1020
acctcccggc tgcacagcgg agtgccgtct agattctcgg gttcggggtc gggaactgac     1080
tactccctta ctatttccaa cctggagcag gaggatattg ccacctactt ctgccaacaa     1140
ggaaacaccc tgccgtacac ttttggcggg ggaaccaagc tggaaatcac tggcagcaca     1200
tccggttccg ggaagcccgg ctccggagag ggcagcacca aggggaagt caagctgcag     1260 gaatcaggac ctggcctggt ggccccgagc cagtcactgt ccgtgacttg tactgtgtcc     1320
ggagtgtcgc tcccggatta cggagtgtcc tggatcaggc agccacctcg gaaaggattg     1380
gaatggctcg gagtcatctg gggttccgaa accacctatt acaactcggc actgaaatcc     1440
aggctcacca ttatcaagga taactccaag tcacaagtgt tcctgaagat gaatagcctg     1500
cagactgacg acacggcgat ctactattgc gccaagcact actactacgg cggatcctac     1560
gctatggact actggggcca ggggaccagc gtgaccgtgt catccgcggc cgcaactacc     1620 accccctgccc ctcggccgcc gactccggcc ccaaccatcg caagccaacc cctctccttg     1680
cgccccgaag cttgccgccc ggcgcgggt ggagccgtgc ataccggggg ctgagcttt       1740 gcctgcgata tctacatttg gcccccgctg ccggcactt gcggcgtgct cctgctgtcg       1800
ctggtcatca ccctttactg caagagggcc cggaagaagc tgctttacat cttcaagcag     1860
ccgttcatgc ggcccgtgca gacgactcag gaagaggacg gatgctcgtg cagattccct     1920
gaggaggaag aggggggatg cgaactgcgc gtcaagttct cacggtccgc cgacgcccc       1980 gcatatcaac agggccagaa tcagctctac aacgagctga acctgggaag agagaggag      2040 tacgacgtgc tggacaagcg acgcggacgc gacccggaga tgggggggaa accacggcgg     2100
aaaaaccctc aggaaggact gtacaacgaa ctccagaaag acaagatggc ggaagcctac     2160
tcagaaatcg ggatgaaggg agagcggagg aggggaaagg gtcacgacgg gctgtaccag     2220
ggactgagca ccgccactaa ggatacctac gatgccttgc atatgcaagc actcccaccc     2280
cgg                                                                   2283

<210> SEQ ID NO 26
<211> LENGTH: 761
<212> TYPE: PRT
<213> ORGANISM: Artificial Sequence
```

<220> FEATURE:
<223> OTHER INFORMATION: LP-CD20 VH-(GGGGS)3-CD20 VL-(GGGGS)5-CD19VL-
      Whitlow linker-CD19 VH-CD8 hinge+TM-41BB-CD3zeta

<400> SEQUENCE: 26

```
Met Leu Leu Leu Val Thr Ser Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65              70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
                100                 105                 110

Ser Ala Asp Tyr Tyr Cys Ala Arg Ser Asn Tyr Tyr Gly Ser Ser Tyr
            115                 120                 125

Trp Phe Phe Asp Val Trp Gly Ala Gly Thr Thr Val Thr Val Ser Ser
        130                 135                 140

Gly Gly Gly Gly Ser Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Ser Gly Gly
            260                 265                 270

Gly Gly Ser Gly Gly Gly Gly Ser Gly Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
```

```
            385                 390                 395                 400
        Ser Gly Ser Gly Lys Pro Gly Ser Gly Glu Gly Ser Thr Lys Gly Glu
                        405                 410                 415

Val Lys Leu Gln Glu Ser Gly Pro Gly Leu Val Ala Pro Ser Gln Ser
                        420                 425                 430

Leu Ser Val Thr Cys Thr Val Ser Gly Val Ser Leu Pro Asp Tyr Gly
                        435                 440                 445

Val Ser Trp Ile Arg Gln Pro Pro Arg Lys Gly Leu Glu Trp Leu Gly
                        450                 455                 460

Val Ile Trp Gly Ser Glu Thr Thr Tyr Tyr Asn Ser Ala Leu Lys Ser
        465                 470                 475                 480

Arg Leu Thr Ile Ile Lys Asp Asn Ser Lys Ser Gln Val Phe Leu Lys
                        485                 490                 495

Met Asn Ser Leu Gln Thr Asp Asp Thr Ala Ile Tyr Tyr Cys Ala Lys
                        500                 505                 510

His Tyr Tyr Tyr Gly Gly Ser Tyr Ala Met Asp Tyr Trp Gly Gln Gly
                        515                 520                 525

Thr Ser Val Thr Val Ser Ser Ala Ala Thr Thr Thr Pro Ala Pro
                530                 535                 540

Arg Pro Pro Thr Pro Ala Pro Thr Ile Ala Ser Gln Pro Leu Ser Leu
        545                 550                 555                 560

Arg Pro Glu Ala Cys Arg Pro Ala Ala Gly Gly Ala Val His Thr Arg
                        565                 570                 575

Gly Leu Asp Phe Ala Cys Asp Ile Tyr Ile Trp Ala Pro Leu Ala Gly
                        580                 585                 590

Thr Cys Gly Val Leu Leu Leu Ser Leu Val Ile Thr Leu Tyr Cys Lys
                        595                 600                 605

Arg Gly Arg Lys Lys Leu Leu Tyr Ile Phe Lys Gln Pro Phe Met Arg
                        610                 615                 620

Pro Val Gln Thr Thr Gln Glu Glu Asp Gly Cys Ser Cys Arg Phe Pro
        625                 630                 635                 640

Glu Glu Glu Glu Gly Gly Cys Glu Leu Arg Val Lys Phe Ser Arg Ser
                        645                 650                 655

Ala Asp Ala Pro Ala Tyr Gln Gln Gly Gln Asn Gln Leu Tyr Asn Glu
                        660                 665                 670

Leu Asn Leu Gly Arg Arg Glu Glu Tyr Asp Val Leu Asp Lys Arg Arg
                        675                 680                 685

Gly Arg Asp Pro Glu Met Gly Gly Lys Pro Arg Arg Lys Asn Pro Gln
                        690                 695                 700

Glu Gly Leu Tyr Asn Glu Leu Gln Lys Asp Lys Met Ala Glu Ala Tyr
        705                 710                 715                 720

Ser Glu Ile Gly Met Lys Gly Glu Arg Arg Arg Gly Lys Gly His Asp
                        725                 730                 735

Gly Leu Tyr Gln Gly Leu Ser Thr Ala Thr Lys Asp Thr Tyr Asp Ala
                        740                 745                 750

Leu His Met Gln Ala Leu Pro Pro Arg
                        755                 760

<210> SEQ ID NO 27
<211> LENGTH: 726
<212> TYPE: DNA
<213> ORGANISM: Mus musculus

<400> SEQUENCE: 27
```

```
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag gtaatacgc ttccgtacac gttcggaggg    300
gggaccaagc tggagatcac aggtggcggt ggctcgggcg gtggtgggtc gggtggcggc   360
ggatctgagg tgaaactgca ggagtcagga cctggcctgg tggcgccctc acagagcctg   420
tccgtcacat gcactgtctc agggtctca ttacccgact atggtgtaag ctggattcgc    480
cagcctccac gaaagggtct ggagtggctg ggagtaatat ggggtagtga aaccacatac   540
tataattcag ctctcaaatc cagactgacc atcatcaagg acaactccaa gagccaagtt   600
ttcttaaaaa tgaacagtct gcaaactgat gacacagcca tttactactg tgccaaacat   660
tattactacg gtggtagcta tgctatggac tactggggcc aaggaacctc agtcaccgtc   720
tcctca                                                               726
```

<210> SEQ ID NO 28
<211> LENGTH: 242
<212> TYPE: PRT
<213> ORGANISM: Artificial Sequence
<220> FEATURE:
<223> OTHER INFORMATION: scFV for CD19

<400> SEQUENCE: 28

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
```

Ser Ser

<210> SEQ ID NO 29
<211> LENGTH: 1485
<212> TYPE: DNA
<213> ORGANISM: Artificial Sequence
<220> FEATURE:
<223> OTHER INFORMATION: LP-CD19binder-CD8link-CD8tm-41BB-CD3zeta

<400> SEQUENCE: 29

| | | |
|---|---|---|
| atgcttctcc tggtcacctc cctgctcctc tgcgaactgc ctcaccctgc cttccttctg | 60 |
| attcctgaca ctgacattca gatgactcag accacctctt ccttgtccgc gtcactggga | 120 |
| gacagagtga ccatctcgtg tcgcgcaagc caggatatct ccaagtacct gaactggtac | 180 |
| caacagaagc ccgacgggac tgtgaagctg ctgatctacc acacctcacg cctgcacagc | 240 |
| ggagtgccaa gcagattctc cggctccggc tcgggaaccg attactcgct taccattagc | 300 |
| aacctcgagc aggaggacat cgctacctac ttctgccagc aaggaaatac cctgccctac | 360 |
| accttcggcg aggaaccaa attggaaatc accggctcca cgagcggctc cgggaagcct | 420 |
| ggttccgggg aaggctccac taaggtgaa gtgaagctcc aggagtccgg ccccggcctg | 480 |
| gtggcgccgt cgcaatcact ctctgtgacc tgtaccgtgt cgggagtgtc cctgcctgat | 540 |
| tacgcgtga gctggattcg gcagccgccg cggaagggcc tggaatggct gggtgtcatc | 600 |
| tggggatccg agactaccta ctacaactcg gccctgaagt cccgcctgac tatcatcaaa | 660 |
| gacaactcga agtcccaggt ctttctgaag atgaactccc tgcaaactga cgacaccgcc | 720 |
| atctattact gtgctaagca ctactactac ggtggaagct atgctatgga ctactggggc | 780 |
| caggggacat ccgtgacagt cagctccgcg gccgcaacta ccaccctgc ccctcggccg | 840 |
| ccgactccgg ccccaaccat cgcaagccaa cccctctcct gcgccccga gcttgccgc | 900 |
| ccggccgcgg gtggagccgt gcatacccgg ggctggact tgcctgcga tatctacatt | 960 |
| tgggcccgc tggccggcac ttgcggcgtg ctcctgctgt cgctggtcat caccctttac | 1020 |
| tgcaagaggg gccggaagaa gctgctttac atcttcaagc agccgttcat gcggcccgtg | 1080 |
| cagacgactc aggaagagga cggatgctcg tgcagattcc ctgaggagga gaggggggga | 1140 |
| tgcgaactgc gcgtcaagtt ctcacggtcc gccgacgccc ccgcatatca acagggccag | 1200 |
| aatcagctct acaacgagct gaacctggga aggagagagg agtacgacgt gctggacaag | 1260 |
| cgacgcggac gcgaccccga gatggggggg aaaccacggc ggaaaaaccc tcaggaagga | 1320 |
| ctgtacaacg aactccagaa agacaagatg gcggaagcct actcagaaat cgggatgaag | 1380 |
| ggagagcgga ggaggggaaa gggtcacgac gggctgtacc agggactgag caccgccact | 1440 |
| aaggatacct acgatgcctt gcatatgcaa gcactcccca cccgg | 1485 |

<210> SEQ ID NO 30
<211> LENGTH: 495
<212> TYPE: PRT
<213> ORGANISM: Artificial Sequence
<220> FEATURE:
<223> OTHER INFORMATION: LP-CD19binder-CD8link-CD8tm-41BB-CD3zeta

<400> SEQUENCE: 30

Met Leu Leu Leu Val Thr Ser Leu Leu Cys Glu Leu Pro His Pro
1               5                   10                  15

Ala Phe Leu Leu Ile Pro Asp Thr Asp Ile Gln Met Thr Gln Thr Thr
            20                  25                  30

```
Ser Ser Leu Ser Ala Ser Leu Gly Asp Arg Val Thr Ile Ser Cys Arg
            35                  40                  45

Ala Ser Gln Asp Ile Ser Lys Tyr Leu Asn Trp Tyr Gln Gln Lys Pro
 50                  55                  60

Asp Gly Thr Val Lys Leu Leu Ile Tyr His Thr Ser Arg Leu His Ser
 65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
                100                 105                 110

Gln Gln Gly Asn Thr Leu Pro Tyr Thr Phe Gly Gly Gly Thr Lys Leu
                115                 120                 125

Glu Ile Thr Gly Ser Thr Ser Gly Ser Gly Lys Pro Gly Ser Gly Glu
            130                 135                 140

Gly Ser Thr Lys Gly Glu Val Lys Leu Gln Glu Ser Gly Pro Gly Leu
145                 150                 155                 160

Val Ala Pro Ser Gln Ser Leu Ser Val Thr Cys Thr Val Ser Gly Val
                165                 170                 175

Ser Leu Pro Asp Tyr Gly Val Ser Trp Ile Arg Gln Pro Pro Arg Lys
            180                 185                 190

Gly Leu Glu Trp Leu Gly Val Ile Trp Gly Ser Glu Thr Thr Tyr Tyr
            195                 200                 205

Asn Ser Ala Leu Lys Ser Arg Leu Thr Ile Ile Lys Asp Asn Ser Lys
            210                 215                 220

Ser Gln Val Phe Leu Lys Met Asn Ser Leu Gln Thr Asp Asp Thr Ala
225                 230                 235                 240

Ile Tyr Tyr Cys Ala Lys His Tyr Tyr Gly Gly Ser Tyr Ala Met
                245                 250                 255

Asp Tyr Trp Gly Gln Gly Thr Ser Val Thr Val Ser Ser Ala Ala Ala
            260                 265                 270

Thr Thr Thr Pro Ala Pro Arg Pro Thr Pro Ala Pro Thr Ile Ala
            275                 280                 285

Ser Gln Pro Leu Ser Leu Arg Pro Glu Ala Cys Arg Pro Ala Ala Gly
            290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
                340                 345                 350

Lys Gln Pro Phe Met Arg Pro Val Gln Thr Thr Gln Glu Glu Asp Gly
                355                 360                 365

Cys Ser Cys Arg Phe Pro Glu Glu Glu Glu Gly Gly Cys Glu Leu Arg
            370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
                420                 425                 430

Arg Arg Lys Asn Pro Gln Glu Gly Leu Tyr Asn Glu Leu Gln Lys Asp
                435                 440                 445
```

-continued

```
                Lys Met Ala Glu Ala Tyr Ser Glu Ile Gly Met Lys Gly Glu Arg Arg
                    450                 455                 460

Arg Gly Lys Gly His Asp Gly Leu Tyr Gln Gly Leu Ser Thr Ala Thr
            465                 470                 475                 480

Lys Asp Thr Tyr Asp Ala Leu His Met Gln Ala Leu Pro Pro Arg
                            485                 490                 495

<210> SEQ ID NO 31
<211> LENGTH: 1470
<212> TYPE: DNA
<213> ORGANISM: Artificial Sequence
<220> FEATURE:
<223> OTHER INFORMATION: LP-CD19binder-CD8link-CD8tm-signals

<400> SEQUENCE: 31
atgcttctcc tggtcacctc cctgctcctc tgcgaactgc tcaccctgc cttccttctg      60 attcctgaca ttcagatgac tcagaccacc tcttccttgt ccgcgtcact gggagacaga     120
gtgaccatct cgtgtcgcgc aagccaggat atctccaagt acctgaactg gtaccaacag     180
aagcccgacg ggactgtgaa gctgctgatc taccacacct cacgcctgca cagcggagtg     240
ccaagcagat tctccggctc cggctcggga accgattact cgcttaccat tagcaacctc     300
gagcaggagg acatcgctac ctacttctgc cagcaaggaa ataccctgcc ctacaccttc     360
ggcggaggaa ccaaattgga aatcaccggc ggaggaggct ccggggagg aggttccggg      420 ggcggggtt ccgaagtgaa gctccaggag tccggccccg gctggtggc gccgtcgcaa      480 tcactctctg tgacctgtac cgtgtcggga gtgtccctgc ctgattacgg cgtgagctgg     540
attcggcagc cgccgcggaa gggcctggaa tggctgggtg tcatctgggg atccgagact     600
acctactaca actcggccct gaagtcccgc ctgactatca tcaaagacaa ctcgaagtcc     660
caggtctttc tgaagatgaa ctccctgcaa actgacgaca ccgccatcta ttactgtgct     720
aagcactact actacggtgg aagctatgct atggactact ggggcaagg cacttcggtg     780 actgtgtcaa gcgcggccgc aactaccacc cctgcccctc ggccgccgac tccggcccca     840
accatcgcaa gccaaccccct ctccttgcgc cccgaagctt gccgcccggc cgcgggtgga     900
gccgtgcata cccgggggct ggactttgcc tgcgatatct catttgggc cccgctggcc     960 ggcacttgcg gcgtgctcct gctgtcgctg gtcatcaccc tttactgcaa gagggccgg    1020 aagaagctgc tttacatctt caagcagccg ttcatgcggc ccgtgcagac gactcaggaa    1080
gaggacggat gctcgtgcag attccctgag gaggaagagg ggggatgcga actgcgcgtc    1140
aagttctcac ggtccgccga cgcccccgca tatcaacagg gccagaatca gctctacaac    1200
gagctgaacc tgggaaggag agaggagtac gacgtgctgg acaagcgacg cggacgcgac    1260
ccggagatgg gggaaacc acggcggaaa accctcagg aaggactgta caacgaactc    1320
cagaaagaca gatggcgga agcctactca gaaatcggga tgaagggaga gcggaggagg    1380
ggaaagggtc acgacgggct gtaccaggga ctgagcaccg ccactaagga tacctacgat    1440
gccttgcata tgcaagcact cccacccgg                                      1470

<210> SEQ ID NO 32
<211> LENGTH: 490
<212> TYPE: PRT
<213> ORGANISM: Artificial Sequence
<220> FEATURE:
<223> OTHER INFORMATION: LP-CD19binder-CD8link-CD8tm-signals

<400> SEQUENCE: 32
```

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
50                      55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
    130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Ala Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
        355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
```

```
                420               425               430
    Gln Glu Gly Leu Tyr Asn Glu Leu Gln Lys Asp Lys Met Ala Glu Ala
                    435                 440                 445

Tyr Ser Glu Ile Gly Met Lys Gly Glu Arg Arg Arg Gly Lys Gly His
            450                 455                 460

Asp Gly Leu Tyr Gln Gly Leu Ser Thr Ala Thr Lys Asp Thr Tyr Asp
    465                 470                 475                 480

Ala Leu His Met Gln Ala Leu Pro Pro Arg
                    485                 490

<210> SEQ ID NO 33
<211> LENGTH: 1548
<212> TYPE: DNA
<213> ORGANISM: Artificial Sequence
<220> FEATURE:
<223> OTHER INFORMATION: CD19_20-reactive scFv binding domain

<400> SEQUENCE: 33
gacattcaga tgactcagac cacctcctcc ctgtccgcct ccctgggcga ccgcgtgacc      60
atctcatgcc gcgccagcca ggacatctcg aagtacctca actggtacca gcagaagccc     120
gacggaaccg tgaagctcct gatctaccac acctcccggc tgcacagcgg agtgccgtct     180
agattctcgg gttcggggtc gggaactgac tactcccctta ctatttccaa cctggagcag    240
gaggatattg ccacctactt ctgccaacaa ggaaacaccc tgccgtacac ttttggcggg     300
ggaaccaagc tggaaatcac tggcagcaca tccggttccg ggaagcccgg ctccggagag     360
ggcagcacca aggggggaagt caagctgcag gaatcaggac ctggcctggt ggcccccgagc    420 cagtcactgt ccgtgacttg tactgtgtcc ggagtgtcgc tcccggatta cggagtgtcc     480
tggatcaggc agccacctcg gaaaggattg aatggctcg gagtcatctg gggttccgaa     540
accacctatt acaactcggc actgaaatcc aggctcacca ttatcaagga taactccaag    600
tcacaagtgt tcctgaagat gaatagcctg cagactgacg acacggcgat ctactattgc    660
gccaagcact actactacgg cggatcctac gctatggact actggggcca ggggaccagc    720
gtgaccgtgt catccggagg cggcggcagc ggcggggag gtccggagg gggtggttct     780 ggtggaggag gatcgggagg cggtggcagc gaggtgcagt tgcaacagtc aggagctgaa    840
ctggtcaagc caggagccag cgtgaagatg agctgcaagg cctccggtta caccttcacc    900
tcctacaaca tgcactgggt gaaacagacc ccgggacaag gctcgaatg gattggcgcc    960 atctaccccg gaatggcga tacttcgtac aaccagaagt tcaagggaaa ggccaccctg    1020
accgccgaca gagctcctc accgcgtat atgcagttga gctccctgac ctccgaggac    1080
tccgccgact actactgcgc acggtccaac tactatggaa gctcgtactg gttcttcgat    1140
gtctgggggg ccggcaccac tgtgaccgtc agctccgggg gcggaggatc cggtggaggc    1200
ggaagcgggg gtgaggatc cgacattgtg ctgactcagt cccggcaat cctgtcggcc    1260 tcaccgggcg aaaaggtcac gatgacttgt agagcgtcgt ccagcgtgaa ctacatggat    1320
tggtaccaaa agaagcctgg atcgtcaccc aagccttgga tctacgctac atctaacctg    1380
gcctccggca tgccagcgcg gttcagcggg tccggctcgg gcacctcata tctcgctgacc    1440 atctcccgcg tggaggctga ggacgccgcg acctactact gccagcagtg gtccttcaac    1500
ccgccgactt ttggaggcgg tactaagctg gagatcaaag cggccgca             1548

<210> SEQ ID NO 34
<211> LENGTH: 516
```

<212> TYPE: PRT
<213> ORGANISM: Artificial Sequence
<220> FEATURE:
<223> OTHER INFORMATION: CD19_20-reactive scFv binding domain

<400> SEQUENCE: 34

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser Gly Gly Gly Gly Ser Gly Gly Gly Gly Ser Gly
                245                 250                 255

Gly Gly Gly Ser Gly Gly Gly Gly Ser Gly Gly Gly Ser Glu Val
            260                 265                 270

Gln Leu Gln Gln Ser Gly Ala Glu Leu Val Lys Pro Gly Ala Ser Val
        275                 280                 285

Lys Met Ser Cys Lys Ala Ser Gly Tyr Thr Phe Thr Ser Tyr Asn Met
290                 295                 300

His Trp Val Lys Gln Thr Pro Gly Gln Gly Leu Glu Trp Ile Gly Ala
305                 310                 315                 320

Ile Tyr Pro Gly Asn Gly Asp Thr Ser Tyr Asn Gln Lys Phe Lys Gly
                325                 330                 335

Lys Ala Thr Leu Thr Ala Asp Lys Ser Ser Thr Ala Tyr Met Gln
            340                 345                 350

Leu Ser Ser Leu Thr Ser Glu Asp Ser Ala Asp Tyr Tyr Cys Ala Arg
        355                 360                 365

Ser Asn Tyr Tyr Gly Ser Ser Tyr Trp Phe Phe Asp Val Trp Gly Ala
370                 375                 380
```

```
Gly Thr Thr Val Thr Val Ser Ser Gly Gly Gly Ser Gly Gly Gly
385                 390                 395                 400

Gly Ser Gly Gly Gly Ser Asp Ile Val Leu Thr Gln Ser Pro Ala
            405                 410                 415

Ile Leu Ser Ala Ser Pro Gly Glu Lys Val Thr Met Thr Cys Arg Ala
            420                 425                 430

Ser Ser Ser Val Asn Tyr Met Asp Trp Tyr Gln Lys Lys Pro Gly Ser
        435                 440                 445

Ser Pro Lys Pro Trp Ile Tyr Ala Thr Ser Asn Leu Ala Ser Gly Val
    450                 455                 460

Pro Ala Arg Phe Ser Gly Ser Gly Ser Gly Thr Ser Tyr Ser Leu Thr
465                 470                 475                 480

Ile Ser Arg Val Glu Ala Glu Asp Ala Ala Thr Tyr Tyr Cys Gln Gln
            485                 490                 495

Trp Ser Phe Asn Pro Pro Thr Phe Gly Gly Gly Thr Lys Leu Glu Ile
        500                 505                 510

Lys Ala Ala Ala
    515

<210> SEQ ID NO 35
<211> LENGTH: 2283
<212> TYPE: DNA
<213> ORGANISM: Artificial Sequence
<220> FEATURE:
<223> OTHER INFORMATION: LP-CD19 VL-Whitlow linker-CD19 VH (GGGGS)5 CD20
      VH (GGGGS)3-CD20 VL CD8 hinge+TM-41BB-CD3zeta

<400> SEQUENCE: 35
atgctccttc tcgtgaccct cctgcttctc tgcgaactgc ccatcctgc cttcctgctg      60 attcccgaca ttcagatgac tcagaccacc tcctccctgt ccgcctccct gggcgaccgc    120
gtgaccatct catgccgcgc cagccaggac atctcgaagt acctcaactg gtaccagcag    180
aagcccgacg gaaccgtgaa gctcctgatc taccacacct ccggctgca cagcggagtg     240 ccgtctagat tctcgggttc ggggtcggga actgactact cccttactat ttccaacctg    300
gagcaggagg atattgccac ctacttctgc caacaaggaa acaccctgcc gtacactttt    360
ggcgggggaa ccaagctgga aatcactggc agcacatccg gttccgggaa gccgggctcc    420
ggagagggca gcaccaaggg ggaagtcaag ctgcaggaat caggacctgg cctggtggcc    480
ccgagccagt cactgtccgt gacttgtact gtgtccggag tgtcgctccc ggattacgga    540
gtgtcctgga tcaggcagcc acctcggaaa ggattggaat ggctcggagt catctggggt    600
tccgaaacca cctattacaa ctcggcactg aaatccaggc tcaccattat caaggataac    660
tccaagtcac aagtgttcct gaagatgaat agcctgcaga ctgacgacac ggcgatctac    720
tattgcgcca agcactacta ctacggcgga tcctacgcta tggactactg gggccagggg    780
accagcgtga ccgtgtcatc cggaggcggc ggcagcggcg gggagggtc cggagggggt    840 ggttctggtg gaggaggatc gggaggcggt ggcagcgagg tgcagttgca acagtcagga    900
gctgaactgg tcaagccagg agccagcgtg aagatgagct gcaaggcctc cggttacacc    960
ttcacctcct acaacatgca ctgggtgaaa cagaccccgg acaagggct cgaatggatt    1020 ggcgccatct accccgggaa tggcgatact tcgtacaacc agaagttcaa gggaaaggcc    1080
accctgaccg ccgacaagag ctcctccacc gcgtatatgc agttgagctc cctgacctcc    1140
gaggactccg ccgactacta ctgcgcacgg tccaactact atggaagctc gtactggttc    1200
ttcgatgtct ggggggccgg caccactgtg accgtcagct ccggggggcgg aggatccggt   1260
```

```
ggaggcggaa gcggggggtgg aggatccgac attgtgctga ctcagtcccc ggcaatcctg    1320
tcggcctcac cgggcgaaaa ggtcacgatg acttgtagag cgtcgtccag cgtgaactac    1380
atggattggt accaaaagaa gcctggatcg tcacccaagc cttggatcta cgctacatct    1440
aacctggcct ccggcgtgcc agcgcggttc agcgggtccg gctcgggcac ctcatactcg    1500
ctgaccatct cccgcgtgga ggctgaggac gccgcgacct actactgcca gcagtggtcc    1560
ttcaacccgc cgacttttgg aggcggtact aagctggaga tcaaagcggc cgcaactacc    1620 accccctgccc ctcggccgcc gactccggcc ccaaccatcg caagccaacc cctctccttg    1680
cgccccgaag cttgccgccc ggccgcgggt ggagccgtgc ataccggggg ctggactttt    1740
gcctgcgata tctacatttg gccccgctg gccggcactt gcggcgtgct cctgctgtcg    1800
ctggtcatca ccctttactg caagagggg cggaagaagc tgctttacat cttcaagcag    1860
ccgttcatgc ggcccgtgca gacgactcag gaagaggacg gatgctcgtg cagattccct    1920
gaggaggaag aggggggatg cgaactcgcg gtcaagttct cacggtccgc cgacgccccc    1980
gcatatcaac agggccagaa tcagctctac aacgagctga acctgggaag agagaggag    2040 tacgacgtgc tggacaagcg acgcggacg gacccggaga tgggggggaa ccacggcgg    2100 aaaaaccctc aggaaggact gtacaacgaa ctccagaaag acaagatggc ggaagcctac    2160
tcagaaatcg ggatgaaggg agagcggagg aggggaaagg gtcacgacgg gctgtaccag    2220
ggactgagca ccgccactaa ggatacctac gatgccttgc atatgcaagc actcccaccc    2280
cgg                                                                   2283
```

<210> SEQ ID NO 36
<211> LENGTH: 761
<212> TYPE: PRT
<213> ORGANISM: Artificial Sequence
<220> FEATURE:
<223> OTHER INFORMATION: LP-CD19 VL-Whitlow linker-CD19 VH (GGGGS)5 CD20
      VH (GGGGS)3-CD20 VL CD8 hinge+TM-41BB-CD3zeta

<400> SEQUENCE: 36

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
```

```
            165                 170                 175
Pro Asp Tyr Gly Val Ser Trp Ile Arg Gln Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
        210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Gly Gly Gly Ser
            260                 265                 270

Gly Gly Gly Gly Ser Gly Gly Gly Ser Gly Gly Gly Gly Ser Gly
            275                 280                 285

Gly Gly Gly Ser Glu Val Gln Leu Gln Gln Ser Gly Ala Glu Leu Val
        290                 295                 300

Lys Pro Gly Ala Ser Val Lys Met Ser Cys Lys Ala Ser Gly Tyr Thr
305                 310                 315                 320

Phe Thr Ser Tyr Asn Met His Trp Val Lys Gln Thr Pro Gly Gln Gly
                325                 330                 335

Leu Glu Trp Ile Gly Ala Ile Tyr Pro Gly Asn Gly Asp Thr Ser Tyr
            340                 345                 350

Asn Gln Lys Phe Lys Gly Lys Ala Thr Leu Thr Ala Asp Lys Ser Ser
        355                 360                 365

Ser Thr Ala Tyr Met Gln Leu Ser Ser Leu Thr Ser Glu Asp Ser Ala
    370                 375                 380

Asp Tyr Tyr Cys Ala Arg Ser Asn Tyr Tyr Gly Ser Ser Tyr Trp Phe
385                 390                 395                 400

Phe Asp Val Trp Gly Ala Gly Thr Thr Val Thr Val Ser Ser Gly Gly
                405                 410                 415

Gly Gly Ser Gly Gly Gly Gly Ser Gly Gly Gly Gly Ser Asp Ile Val
            420                 425                 430

Leu Thr Gln Ser Pro Ala Ile Leu Ser Ala Ser Pro Gly Glu Lys Val
        435                 440                 445

Thr Met Thr Cys Arg Ala Ser Ser Ser Val Asn Tyr Met Asp Trp Tyr
    450                 455                 460

Gln Lys Lys Pro Gly Ser Ser Pro Lys Pro Trp Ile Tyr Ala Thr Ser
465                 470                 475                 480

Asn Leu Ala Ser Gly Val Pro Ala Arg Phe Ser Gly Ser Gly Ser Gly
                485                 490                 495

Thr Ser Tyr Ser Leu Thr Ile Ser Arg Val Glu Ala Glu Asp Ala Ala
            500                 505                 510

Thr Tyr Tyr Cys Gln Gln Trp Ser Phe Asn Pro Pro Thr Phe Gly Gly
        515                 520                 525

Gly Thr Lys Leu Glu Ile Lys Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590
```

```
Thr Cys Gly Val Leu Leu Ser Leu Val Ile Thr Leu Tyr Cys Lys
        595                 600                 605
Arg Gly Arg Lys Lys Leu Leu Tyr Ile Phe Lys Gln Pro Phe Met Arg
610                 615                 620
Pro Val Gln Thr Thr Gln Glu Glu Asp Gly Cys Ser Cys Arg Phe Pro
625                 630                 635                 640
Glu Glu Glu Glu Gly Gly Cys Glu Leu Arg Val Lys Phe Ser Arg Ser
                645                 650                 655
Ala Asp Ala Pro Ala Tyr Gln Gln Gly Gln Asn Gln Leu Tyr Asn Glu
            660                 665                 670
Leu Asn Leu Gly Arg Arg Glu Glu Tyr Asp Val Leu Asp Lys Arg Arg
        675                 680                 685
Gly Arg Asp Pro Glu Met Gly Gly Lys Pro Arg Arg Lys Asn Pro Gln
690                 695                 700
Glu Gly Leu Tyr Asn Glu Leu Gln Lys Asp Lys Met Ala Glu Ala Tyr
705                 710                 715                 720
Ser Glu Ile Gly Met Lys Gly Glu Arg Arg Arg Gly Lys Gly His Asp
                725                 730                 735
Gly Leu Tyr Gln Gly Leu Ser Thr Ala Thr Lys Asp Thr Tyr Asp Ala
            740                 745                 750
Leu His Met Gln Ala Leu Pro Pro Arg
        755                 760

<210> SEQ ID NO 37
<211> LENGTH: 732
<212> TYPE: DNA
<213> ORGANISM: Artificial Sequence
<220> FEATURE:
<223> OTHER INFORMATION: mesothelin-reactive scFv binding domain

<400> SEQUENCE: 37
gaggtccagc tggtacagtc tgggggaggc ttggtacagc ctgggggtc cctgagactc       60 tcctgtgcag cctctggatt cacctttgat gattatgcca tgcactgggt ccggcaagct      120
ccagggaagg gcctggagtg ggtctcaggt attagttgga atagtggtag cataggctat      180
gcggactctg tgaagggccg attcaccatc tccagagaca acgccaagaa ctccctgtat      240
ctgcaaatga acagtctgag agctgaggac acggccttgt attactgtgc aaaagattta      300
tcgtcagtgg ctggaccctt taactactgg ggccagggca ccctggtcac cgtctcctca      360
ggaggtggcg gtctggtgg aggcggtagc ggcggtggcg gatcctcttc tgagctgact      420
caggaccctg ctgtgtctgt ggccttggga cagacagtca ggatcacatg ccaaggagac      480
agcctcagaa gctattatgc aagctggtac cagcagaagc caggacaggc ccctgtactt      540
gtcatctatg gtaaaaacaa ccggccctca gggatcccag accgattctc tggctccagc      600
tcaggaaaca cagcttcctt gaccatcact ggggctcagg cggaggatga ggctgactat      660
tactgtaact cccgggacag cagtggtaac catctggtat tcggcggagg cacccagctg      720
accgtcctcg gt                                                          732

<210> SEQ ID NO 38
<211> LENGTH: 244
<212> TYPE: PRT
<213> ORGANISM: Artificial Sequence
<220> FEATURE:
<223> OTHER INFORMATION: mesothelin-reactive scFv binding domain

<400> SEQUENCE: 38
```

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Leu Ser Ser Val Ala Gly Pro Phe Asn Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
            165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
            195                 200                 205

Ile Thr Gly Ala Gln Ala Glu Asp Glu Ala Asp Tyr Tyr Cys Asn Ser
        210                 215                 220

Arg Asp Ser Ser Gly Asn His Leu Val Phe Gly Gly Thr Gln Leu
225                 230                 235                 240

Thr Val Leu Gly

<210> SEQ ID NO 39
<211> LENGTH: 1476
<212> TYPE: DNA
<213> ORGANISM: Artificial Sequence
<220> FEATURE:
<223> OTHER INFORMATION: LP-LTG1904-CD8 TM-41BB-CD3zeta

<400> SEQUENCE: 39
atgctgctgc tggtgaccag cctgctgctg tgcgaactgc cgcatccggc gtttctgctg      60
attccggagg tccagctggt acagtctggg ggaggcttgg tacagcctgg ggggtccctg     120
agactctcct gtgcagcctc tggattcacc tttgatgatt atgccatgca ctgggtccgg     180
caagctccag ggaagggcct ggagtgggtc tcaggtatta gttggaatag tggtagcata     240
ggctatgcgg actctgtgaa gggccgattc accatctcca gagacaacgc caagaactcc     300
ctgtatctgc aaatgaacag tctgagagct gaggacacgg ccttgtatta ctgtgcaaaa     360
gatttatcgt cagtggctgg acccttaac tactgggggcc agggcaccct ggtcaccgtc     420
tcctcaggag gtggcgggtc tggtggaggc ggtagcggcg gtggcggatc ctcttctgag     480
ctgactcagg accctgctgt gtctgtggcc ttgggacaga cagtcaggat cacatgccaa     540
ggagacagcc tcagaagcta ttatgcaagc tggtaccagc agaagccagg acaggcccct     600
gtacttgtca tctatggtaa aaacaaccgg ccctcaggga tcccagaccg attctctggc     660

```
tccagctcag gaaacacagc ttccttgacc atcactgggg ctcaggcgga ggatgaggct    720
gactattact gtaactcccg ggacagcagt ggtaaccatc tggtattcgg cggaggcacc    780
cagctgaccg tcctcggtgc ggccgcaact accacccctg ccctcggcc gccgactccg     840
gccccaacca tcgcaagcca acccctctcc ttgcgcccg aagcttgccg ccggccgcg      900
ggtggagccg tgcataccg ggggctggac tttgcctgcg atatctacat ttgggccccg     960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagagggggg atgcgaactg   1140
cgcgtcaagt tctcacggtc cgccgacgcc cccgcatatc aacagggcca gaatcagctc   1200
tacaacgagc tgaacctggg aaggagagag gagtacgacg tgctggacaa gcgacgcgga   1260
cgcgacccgg agatgggggg gaaaccacgg cggaaaaacc ctcaggaagg actgtacaac   1320
gaactccaga agacaagat ggcggaagcc tactcagaaa tcgggatgaa gggagagcgg   1380
aggaggggaa agggtcacga cgggctgtac cagggactga gcaccgccac taaggatacc   1440
tacgatgcct tgcatatgca agcactccca ccccgg                             1476

<210> SEQ ID NO 40
<211> LENGTH: 492
<212> TYPE: PRT
<213> ORGANISM: Artificial Sequence
<220> FEATURE:
<223> OTHER INFORMATION: LP-LTG1904-CD8 TM-41BB-CD3zeta

<400> SEQUENCE: 40

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
                20                  25                  30

Leu Val Gln Pro Gly Gly Ser Leu Arg Leu Ser Cys Ala Ala Ser Gly
            35                  40                  45

Phe Thr Phe Asp Asp Tyr Ala Met His Trp Val Arg Gln Ala Pro Gly
        50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Lys Asp Leu Ser Ser Val Ala Gly Pro
        115                 120                 125

Phe Asn Tyr Trp Gly Gln Gly Thr Leu Val Thr Val Ser Ser Gly Gly
    130                 135                 140

Gly Gly Ser Gly Gly Gly Ser Gly Gly Gly Ser Ser Glu
145                 150                 155                 160

Leu Thr Gln Asp Pro Ala Val Ser Val Ala Leu Gly Gln Thr Val Arg
                165                 170                 175

Ile Thr Cys Gln Gly Asp Ser Leu Arg Ser Tyr Tyr Ala Ser Trp Tyr
            180                 185                 190

Gln Gln Lys Pro Gly Gln Ala Pro Val Leu Val Ile Tyr Gly Lys Asn
        195                 200                 205

Asn Arg Pro Ser Gly Ile Pro Asp Arg Phe Ser Gly Ser Ser Ser Gly
```

Asn Thr Ala Ser Leu Thr Ile Thr Gly Ala Gln Ala Glu Asp Glu Ala
225                 230                 235                 240

Asp Tyr Tyr Cys Asn Ser Arg Asp Ser Ser Gly Asn His Leu Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
            290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Glu Gly Gly Cys Glu Leu Arg Val Lys Phe
370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 41
<211> LENGTH: 339
<212> TYPE: DNA
<213> ORGANISM: Artificial Sequence
<220> FEATURE:
<223> OTHER INFORMATION: CD33-reactive single chain binding domain VH-4

<400> SEQUENCE: 41
gaggtgcagc tggtggagtc tgggggaggc ttggtacagc ctggagggtc cctgagactc    60
tcctgtgcag cctctggatt caccttcagt agctatggca tgagctgggt ccgccaggct   120
ccaagacaag ggcttgagtg ggtggccaac ataaagcaag atggaagtga aaatactat   180 gcggactcag tgaagggccg attcaccatc tccagagaca attccaagaa cacgctgtat   240
ctgcaaatga acagcctgag agccgaggac acagccacgt attactgtgc gaaagaaaat   300
gtggactggg gccagggcac cctggtcacc gtctcctca                          339

<210> SEQ ID NO 42
<211> LENGTH: 113
<212> TYPE: PRT

<213> ORGANISM: Artificial Sequence
<220> FEATURE:
<223> OTHER INFORMATION: CD33-reactive single chain binding domain VH-4

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Arg Gln Gly Leu Glu Trp Val
        35                  40                  45

Ala Asn Ile Lys Gln Asp Gly Ser Glu Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Glu Asn Val Asp Trp Gly Gln Gly Thr Leu Val Thr Val Ser
            100                 105                 110

Ser
```

<210> SEQ ID NO 43
<211> LENGTH: 1083
<212> TYPE: DNA
<213> ORGANISM: Artificial Sequence
<220> FEATURE:
<223> OTHER INFORMATION: LP-VH4-CD8 TM-41BB-CD3zeta

<400> SEQUENCE: 43

| | | | | | |
|---|---|---|---|---|---|
| atgctgctgc | tggtgaccag | cctgctgctg | tgcgaactgc | gcatccggc | gtttctgctg | 60 |
| attccggagg | tgcagctggt | ggagtctggg | ggaggcttgg | tacagcctgg | agggtccctg | 120 |
| agactctcct | gtgcagcctc | tggattcacc | ttcagtagct | atggcatgag | ctgggtccgc | 180 |
| caggctccaa | gacaagggct | tgagtgggtg | gccaacataa | agcaagatgg | aagtgagaaa | 240 |
| tactatgcgg | actcagtgaa | gggccgattc | accatctcca | gagacaattc | caagaacacg | 300 |
| ctgtatctgc | aaatgaacag | cctgagagcc | gaggacacag | ccacgtatta | ctgtgcgaaa | 360 |
| gaaaatgtgg | actggggcca | gggcaccctg | gtcaccgtct | cctcagcggc | cgcaactacc | 420 |
| accccctgccc | ctcggccgcc | gactccggcc | caaccatcg | caagccaacc | cctctccttg | 480 |
| cgccccgaag | cttgccgccc | ggccgcgggt | ggagccgtgc | atacccgggg | gctggacttt | 540 |
| gcctgcgata | tctacatttg | gcccccgctg | ccggcacttt | cggcgtgct | cctgctgtcg | 600 |
| ctggtcatca | cccttttactg | caagagggggc | cggaagaagc | tgctttacat | cttcaagcag | 660 |
| ccgttcatgc | ggcccgtgca | gacgactcag | gaagaggacg | gatgctcgtg | cagattccct | 720 |
| gaggaggaag | aggggggatg | cgaactgcgc | gtcaagttct | cacggtccgc | cgacgccccc | 780 |
| gcatatcaac | agggccagaa | tcagctctac | aacgagctga | acctgggaag | agagaggag | 840 |
| tacgacgtgc | tggacaagcg | acgcggacgc | gacccggaga | tggggggaa | accacggcgg | 900 |
| aaaaaccctc | aggaaggact | gtacaacgaa | ctccagaaag | acaagatggc | ggaagcctac | 960 |
| tcagaaatcg | ggatgaaggg | agagcggagg | aggggaaagg | gtcacgacgg | gctgtaccag | 1020 |
| ggactgagca | ccgccactaa | ggatacctac | gatgccttgc | atatgcaagc | actcccaccc | 1080 |
| cgg | | | | | | 1083 |

<210> SEQ ID NO 44

```
<211> LENGTH: 361
<212> TYPE: PRT
<213> ORGANISM: Artificial Sequence
<220> FEATURE:
<223> OTHER INFORMATION: LP-VH4-CD8 TM-41BB-CD3zeta

<400> SEQUENCE: 44

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Gly Met Ser Trp Val Arg Gln Ala Pro Arg
    50                  55                  60

Gln Gly Leu Glu Trp Val Ala Asn Ile Lys Gln Asp Gly Ser Glu Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Thr Tyr Tyr Cys Ala Lys Glu Asn Val Asp Trp Gly Gln Gly
        115                 120                 125

Thr Leu Val Thr Val Ser Ser Ala Ala Ala Thr Thr Thr Pro Ala Pro
    130                 135                 140

Arg Pro Pro Thr Pro Ala Pro Thr Ile Ala Ser Gln Pro Leu Ser Leu
145                 150                 155                 160

Arg Pro Glu Ala Cys Arg Pro Ala Ala Gly Gly Ala Val His Thr Arg
                165                 170                 175

Gly Leu Asp Phe Ala Cys Asp Ile Tyr Ile Trp Ala Pro Leu Ala Gly
            180                 185                 190

Thr Cys Gly Val Leu Leu Leu Ser Leu Val Ile Thr Leu Tyr Cys Lys
        195                 200                 205

Arg Gly Arg Lys Lys Leu Leu Tyr Ile Phe Lys Gln Pro Phe Met Arg
    210                 215                 220

Pro Val Gln Thr Thr Gln Glu Glu Asp Gly Cys Ser Cys Arg Phe Pro
225                 230                 235                 240

Glu Glu Glu Glu Gly Gly Cys Glu Leu Arg Val Lys Phe Ser Arg Ser
                245                 250                 255

Ala Asp Ala Pro Ala Tyr Gln Gln Gly Gln Asn Gln Leu Tyr Asn Glu
            260                 265                 270

Leu Asn Leu Gly Arg Arg Glu Glu Tyr Asp Val Leu Asp Lys Arg Arg
        275                 280                 285

Gly Arg Asp Pro Glu Met Gly Gly Lys Pro Arg Arg Lys Asn Pro Gln
    290                 295                 300

Glu Gly Leu Tyr Asn Glu Leu Gln Lys Asp Lys Met Ala Glu Ala Tyr
305                 310                 315                 320

Ser Glu Ile Gly Met Lys Gly Glu Arg Arg Gly Lys Gly His Asp
                325                 330                 335

Gly Leu Tyr Gln Gly Leu Ser Thr Ala Thr Lys Asp Thr Tyr Asp Ala
            340                 345                 350

Leu His Met Gln Ala Leu Pro Pro Arg
        355                 360

<210> SEQ ID NO 45
```

```
<211> LENGTH: 797
<212> TYPE: DNA
<213> ORGANISM: Artificial Sequence
<220> FEATURE:
<223> OTHER INFORMATION: TSLPR-reactive scFv binding domain

<400> SEQUENCE: 45
atggcactgc cgtgaccgc cctgcttctg ccgcttgcac ttctgctgca cgccgctagg      60
ccccaagtca ccctcaaaga gtcagggcca ggaatcctca gccctcaca gactctgtct    120
cttacttgct cattcagcgg attcagcctt tccacctctg gtatgggcgt ggggtggatt    180
aggcaaccta gcggaaaggg gcttgaatgg ctggcccaca tctggtggga cgacgacaag    240
tactacaacc cctcactgaa gtcccagctc actatttcca agatacttc ccggaatcag    300
gtgttcctca agattacctc tgtcgacacc gctgataccg ccacttacta ttgttcacgc    360
agaccgagag gtaccatgga cgca

```
Thr Ile Ser Cys Arg Ala Ser Gln Asp Ile Ser Lys Tyr Leu Asn Trp
            180                 185                 190

Tyr Gln Gln Lys Pro Asp Gly Thr Val Lys Leu Leu Ile Tyr Tyr Thr
        195                 200                 205

Ser Arg Leu His Ser Gly Val Pro Ser Arg Phe Ser Gly Ser Gly Ser
    210                 215                 220

Gly Thr Asp Tyr Ser Leu Thr Ile Arg Asn Leu Glu Gln Glu Asp Ile
225                 230                 235                 240

Ala Thr Tyr Phe Cys Gln Gln Val Tyr Thr Leu Pro Trp Thr Phe Gly
                245                 250                 255

Gly Gly Thr Lys Leu Glu Ile Lys Ser
            260                 265

<210> SEQ ID NO 47
<211> LENGTH: 1170
<212> TYPE: DNA
<213> ORGANISM: Artificial Sequence
<220> FEATURE:
<223> OTHER INFORMATION: LP-3G11-CD8 TM-41BB-CD3zeta

<400> SEQUENCE: 47
atggcactgc cgtgaccgc  cctgcttctg  ccgcttgcac  ttctgctgca  cgccgctagg    60
ccccaagtca ccctcaaaga gtcagggcca ggaatcctca agccctcaca gactctgtct       120
cttacttgct cattcagcgg attcagcctt tccacctctg gtatgggcgt ggggtggatt       180
aggcaaccta gcggaaaggg gcttgaatgg ctggcccaca tctggtggga cgacgacaag       240
tactacaacc cctcactgaa gtcccagctc actatttcca aagatacttc ccggaatcag       300
gtgttcctca agattaccct tgtcgacacc gctgataccg ccacttacta ttgttcacgc       360
agaccgagag gtaccatgga cgcaatggac tactggggac agggcaccag cgtgaccgtg       420
tcatctggcg gtggagggtc aggaggtgga ggtagcggag gcggtgggtc gacattgtc       480 atgacccagg ccgccagcag cctgagcgct tcactgggcg acagggtgac catcagctgt       540
cgcgcatcac aagatatctc taagtatctt aattggtacc agcaaaagcc ggatggaacc       600
gtgaagctgc tgatctacta cacctcacgg ctgcattctg gagtgcctag ccgctttagc       660
ggcacttgcg gcgtgctcct gctgtcgctg gtcatcaccc tttactgcaa gaggggccgg       720
aagaagctgc tttacatctt caagcagccg ttcatgcggc ccgtgcagac gactcaggaa       780
gaggacggat gctcgtgcag attccctgag gaggaagagg ggggatgcga actgcgcgtc       840
aagttctcac ggtccgccga cgccccccgca tatcaacagg gccagaatca gctctacaac       900
gagctgaacc tgggaaggag agaggagtac gacgtgctgg acaagcgacg cggacgcgac       960
ccggagatgg gggggaaacc acggcggaaa aaccctcagg aaggactgta caacgaactc      1020
cagaaagaca gatggcgga  agcctactca gaaatcggga tgaagggaga gcggaggagg      1080
ggaaagggtc acgacgggct gtaccaggga ctgagcaccg ccactaagga tacctacgat      1140
gccttgcata tgcaagcact cccaccccgg                                      1170

<210> SEQ ID NO 48
<211> LENGTH: 490
<212> TYPE: PRT
<213> ORGANISM: Artificial Sequence
<220> FEATURE:
<223> OTHER INFORMATION: LP-3G11-CD8 TM-41BB-CD3zeta

<400> SEQUENCE: 48

Met Ala Leu Pro Val Thr Ala Leu Leu Leu Pro Leu Ala Leu Leu Leu
```

```
1               5                   10                  15
His Ala Ala Arg Pro Gln Val Thr Leu Lys Glu Ser Gly Pro Gly Ile
                20                  25                  30
Leu Lys Pro Ser Gln Thr Leu Ser Leu Thr Cys Ser Phe Ser Gly Phe
                35                  40                  45
Ser Leu Ser Thr Ser Gly Met Gly Val Gly Trp Ile Arg Gln Pro Ser
        50                  55                  60
Gly Lys Gly Leu Glu Trp Leu Ala His Ile Trp Trp Asp Asp Asp Lys
65                  70                  75                  80
Tyr Tyr Asn Pro Ser Leu Lys Ser Gln Leu Thr Ile Ser Lys Asp Thr
                85                  90                  95
Ser Arg Asn Gln Val Phe Leu Lys Ile Thr Ser Val Asp Thr Ala Asp
                100                 105                 110
Thr Ala Thr Tyr Tyr Cys Ser Arg Arg Pro Arg Gly Thr Met Asp Ala
                115                 120                 125
Met Asp Tyr Trp Gly Gln Gly Thr Ser Val Thr Val Ser Ser Gly Gly
        130                 135                 140
Gly Gly Ser Gly Gly Gly Ser Gly Gly Gly Ser Asp Ile Val
145                 150                 155                 160
Met Thr Gln Ala Ala Ser Ser Leu Ser Ala Ser Leu Gly Asp Arg Val
                165                 170                 175
Thr Ile Ser Cys Arg Ala Ser Gln Asp Ile Ser Lys Tyr Leu Asn Trp
                180                 185                 190
Tyr Gln Gln Lys Pro Asp Gly Thr Val Lys Leu Leu Ile Tyr Tyr Thr
                195                 200                 205
Ser Arg Leu His Ser Gly Val Pro Ser Arg Phe Ser Gly Ser Gly Ser
                210                 215                 220
Gly Thr Asp Tyr Ser Leu Thr Ile Arg Asn Leu Glu Gln Glu Asp Ile
225                 230                 235                 240
Ala Thr Tyr Phe Cys Gln Gln Val Tyr Thr Leu Pro Trp Thr Phe Gly
                245                 250                 255
Gly Gly Thr Lys Leu Glu Ile Lys Ala Ala Ala Thr Thr Thr Pro Ala
                260                 265                 270
Pro Arg Pro Pro Thr Pro Ala Pro Thr Ile Ala Ser Gln Pro Leu Ser
                275                 280                 285
Leu Arg Pro Glu Ala Cys Arg Pro Ala Ala Gly Gly Ala Val His Thr
                290                 295                 300
Arg Gly Leu Asp Phe Ala Cys Asp Ile Tyr Ile Trp Ala Pro Leu Ala
305                 310                 315                 320
Gly Thr Cys Gly Val Leu Leu Leu Ser Leu Val Ile Thr Leu Tyr Cys
                325                 330                 335
Lys Arg Gly Arg Lys Lys Leu Leu Tyr Ile Phe Lys Gln Pro Phe Met
                340                 345                 350
Arg Pro Val Gln Thr Thr Gln Glu Glu Asp Gly Cys Ser Cys Arg Phe
                355                 360                 365
Pro Glu Glu Glu Glu Gly Gly Cys Glu Leu Arg Val Lys Phe Ser Arg
                370                 375                 380
Ser Ala Asp Ala Pro Ala Tyr Gln Gln Gly Gln Asn Gln Leu Tyr Asn
385                 390                 395                 400
Glu Leu Asn Leu Gly Arg Arg Glu Glu Tyr Asp Val Leu Asp Lys Arg
                405                 410                 415
Arg Gly Arg Asp Pro Glu Met Gly Gly Lys Pro Arg Arg Lys Asn Pro
                420                 425                 430
```

Gln Glu Gly Leu Tyr Asn Glu Leu Gln Lys Asp Lys Met Ala Glu Ala
            435                 440                 445

Tyr Ser Glu Ile Gly Met Lys Gly Glu Arg Arg Gly Lys Gly His
        450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 49
<211> LENGTH: 1467
<212> TYPE: DNA
<213> ORGANISM: Artificial Sequence
<220> FEATURE:
<223> OTHER INFORMATION: LP-CD19-TNFRSF19TM-41BB-CD3zeta

<400> SEQUENCE: 49

```
atgctgctgc tggtcaccag cctgctgctg tgcgagctcc ctcacccgc ctttctgctt      60
atcccggaca ttcagatgac acagaccacc tcgagcttgt ccgcgtcgct gggcgatcgc    120
gtgaccatct cctgccgggc ctcccaagac atttcaaagt atctcaactg gtaccagcag    180
aagccggacg gaaccgtgaa actgctgatc taccatacca gccgcctgca ctccggcgtg    240
ccgtcccgct ctccggatc gggttccgga actgactact cactgactat ctccaacttg    300
gaacaagagg acatcgccac ttacttctgt caacaaggaa ataccttcc ctacaccttc    360
ggggggggta ccaagctgga gatcactggg ggcggaggct ccggtggagg cggatccggc    420
ggtggaggga gcgaagtcaa gctgcaggaa tcaggaccag gactcgtggc gccatcccag    480
tccctgtcgg tgacctgtac tgtctccgga gtcagcctcc ccgattacgg agtgtcatgg    540
attaggcaac cccaagaaa agggctggaa tggctcggag tgatctgggg ctccgaaacc    600
acctactaca actcggcgct gaagtcccgg ctgaccatca tcaaggacaa ctccaagagc    660
caagtgttct tgaagatgaa cagcttgcag accgacgata ccgcaatcta ctactgtgcc    720
aagcactatt actacggggg gtcttacgcc atggactact ggggacaggg cacctccgtg    780
actgtgtcgt ccgcggccgc gcccgccct cggccccga ctcctgcccc gacgatcgct    840
tcccaacctc tctcgctgcg cccggaagca tgccggcccg ccgccggtgg cgctgtccac    900
actcgcggac tggactttga taccgcactg gcggccgtga tctgtagcgc cctggccacc    960
gtgctgctgg cgctgctcat cctttgcgtg atctactgca agcggcagcc taggcgaaag   1020
aagctcctct acattttcaa gcaacccttc atgcgccccg tgcaaaccac ccaggaggag   1080
gatggatgct catgccggtt ccctgaggaa gagagggcg gttgcgagct cagagtgaaa   1140
ttcagccggt cggctgacgc cccggcgtac cagcagggcc agaaccagct gtacaatgag   1200
ctcaacctgg gcgccgcga agagtacgac gtgctggaca gaggagagg cagagatccg   1260
gaaatgggcg gaaagccaag gcggaagaac cgcaggaag gtctttacaa cgaactgcag   1320
aaggacaaga tggccgaggc ctactccgag attgggatga agggagaaag acggagggga   1380
aagggacatg acggacttta ccagggcctg agcactgcca cgaaggacac ctatgatgcc   1440
ctgcacatgc aggcgctgcc gcctcgg                                      1467
```

<210> SEQ ID NO 50
<211> LENGTH: 489
<212> TYPE: PRT
<213> ORGANISM: Artificial Sequence
<220> FEATURE:

<223> OTHER INFORMATION: LP-CD19-TNFRSF19TM-41BB-CD3zeta

<400> SEQUENCE: 50

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Gly Gly Gly Ser Gly Gly Gly Ser Gly Gly Gly Gly Ser
130                 135                 140

Glu Val Lys Leu Gln Glu Ser Gly Pro Gly Leu Val Ala Pro Ser Gln
145                 150                 155                 160

Ser Leu Ser Val Thr Cys Thr Val Ser Gly Val Ser Leu Pro Asp Tyr
                165                 170                 175

Gly Val Ser Trp Ile Arg Gln Pro Pro Arg Lys Gly Leu Glu Trp Leu
            180                 185                 190

Gly Val Ile Trp Gly Ser Glu Thr Thr Tyr Tyr Asn Ser Ala Leu Lys
        195                 200                 205

Ser Arg Leu Thr Ile Ile Lys Asp Asn Ser Lys Ser Gln Val Phe Leu
    210                 215                 220

Lys Met Asn Ser Leu Gln Thr Asp Asp Thr Ala Ile Tyr Tyr Cys Ala
225                 230                 235                 240

Lys His Tyr Tyr Tyr Gly Gly Ser Tyr Ala Met Asp Tyr Trp Gly Gln
                245                 250                 255

Gly Thr Ser Val Thr Val Ser Ser Ala Ala Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Asp Thr Ala Leu Ala Val Ile Cys Ser Ala Leu Ala Thr
305                 310                 315                 320

Val Leu Leu Ala Leu Leu Ile Leu Cys Val Ile Tyr Cys Lys Arg Gln
                325                 330                 335

Pro Arg Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400
```

```
Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Lys Asn Pro Gln
        420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 51
<211> LENGTH: 2280
<212> TYPE: DNA
<213> ORGANISM: Artificial Sequence
<220> FEATURE:
<223> OTHER INFORMATION: LP-CD20_CD19-CD8TM-CD28-CD3zeta

<400> SEQUENCE: 51
atgctccttc tcgtgacctc cctgcttctc tgcgaactgc ccatcctgc cttcctgctg     60 attcccgagg tgcagttgca acagtcagga gctgaactgg tcaagccagg agccagcgtg    120
aagatgagct gcaaggcctc cggttacacc ttcacctcct acaacatgca ctgggtgaaa    180
cagaccccgg acaagggct cgaatggatt ggcgccatct accccggaa tggcgatact     240 tcgtacaacc agaagttcaa gggaaaggcc accctgaccg ccgacaagag ctcctccacc    300
gcgtatatgc agttgagctc cctgacctcc gaggactccg ccgactacta ctgcgcacgg    360
tccaactact atggaagctc gtactggttc ttcgatgtct ggggggccgg caccactgtg    420
accgtcagct ccggggggcgg aggatccggt ggaggcggaa gcgggggtgg aggatccgac    480
attgtgctga ctcagtcccc ggcaatcctg tcggcctcac cgggcgaaaa ggtcacgatg    540
acttgtagag cgtcgtccag cgtgaactac atggattggt accaaaagaa gcctggatcg    600
tcacccaagc cttggatcta cgctacatct aacctggcct ccggcgtgcc agcgcggttc    660
agcgggtccg gctcgggcac ctcatactcg ctgaccatct cccgcgtgga ggctgaggac    720
gccgcgacct actactgcca gcagtggtcc ttcaacccgc cgacttttgg aggcggtact    780
aagctggaga tcaaaggagg cggcggcagc ggcggggag ggtccggagg ggtggttct     840 ggtggaggag atcgggagg cggtggcagc gacattcaga tgactcagac caccctcctcc    900 ctgtccgcct ccctgggcga ccgcgtgacc atctcatgcc gcgccagcca ggacatctcg    960
aagtacctca ctggtaccag cagaagccc gacggaaccg tgaagctcct gatctaccac    1020
acctcccggc tgcacagcgg agtgccgtct agattctcgg gttcggggtc gggaactgac    1080 tactcccctta ctatttccaa cctggagcag gaggatattg ccacctactt ctgccaacaa    1140
ggaaacaccc tgccgtacac ttttggcggg ggaaccaagc tggaaatcac tggcagcaca    1200
tccggttccg ggaagcccgg ctccggagag ggcagcacca agggggaagt caagctgcag    1260
gaatcaggac ctgcctggt ggccccgagc cagtcactgt ccgtgacttg tactgtgtcc    1320
ggagtgtcgc tcccggatta cggagtgtcc tggatcaggc agccacctcg gaaaggattg    1380
gaatggctcg gagtcatctg gggttccgaa accacctatt acaactcggc actgaaatcc    1440
aggctcacca ttatcaagga taactccaag tcacaagtgt tcctgaagat gaatagcctg    1500
cagactgacg acacggcgat ctactattgc gccaagcact actactacgg cggatcctac    1560
```

```
gctatggact actggggcca ggggaccagc gtgaccgtgt catccgcggc cgcgactacc  1620
actcctgcac cacggccacc tacccagcc cccaccattg caagccagcc actttcactg   1680
cgccccgaag cgtgtagacc agctgctgga ggagccgtgc atacccgagg gctggacttc  1740
gcctgtgaca tctacatctg gcccccattg gctggaactt gcggcgtgct gctcttgtct  1800
ctggtcatta ccctgtactg ccggtcgaag aggtccagac tcttgcactc cgactacatg  1860
aacatgactc ctagaaggcc cggacccact agaaagcact accagccgta cgcccctcct  1920
cgggatttcg ccgcataccg gtccagagtg aagttcagcc gctcagccga tgcaccggcc  1980
taccagcagg gacagaacca gctctacaac gagctcaacc tgggtcggcg ggaagaatat  2040
gacgtgctgg acaaacggcg cggcagagat ccggagatgg ggggaaagcc gaggaggaag  2100
aaccctcaag agggcctgta caacgaactg cagaaggaca gatggcgga agcctactcc   2160
gagatcggca tgaagggaga acgccggaga gggaagggtc atgacggact gtaccagggc  2220
ctgtcaactg ccactaagga cacttacgat gcgctccata tgcaagcttt gccccgcgg   2280
```

<210> SEQ ID NO 52
<211> LENGTH: 760
<212> TYPE: PRT
<213> ORGANISM: Artificial Sequence
<220> FEATURE:
<223> OTHER INFORMATION: LP-CD20_CD19-CD8TM-CD28-CD3zeta

<400> SEQUENCE: 52

```
Met Leu Leu Leu Val Thr Ser Leu Leu Cys Glu Leu Pro His Pro
1               5                   10                  15

Ala Phe Leu Leu Ile Pro Glu Val Gln Leu Gln Gln Ser Gly Ala Glu
            20                  25                  30

Leu Val Lys Pro Gly Ala Ser Val Lys Met Ser Cys Lys Ala Ser Gly
        35                  40                  45

Tyr Thr Phe Thr Ser Tyr Asn Met His Trp Val Lys Gln Thr Pro Gly
    50                  55                  60

Gln Gly Leu Glu Trp Ile Gly Ala Ile Tyr Pro Gly Asn Gly Asp Thr
65                  70                  75                  80

Ser Tyr Asn Gln Lys Phe Lys Gly Lys Ala Thr Leu Thr Ala Asp Lys
                85                  90                  95

Ser Ser Ser Thr Ala Tyr Met Gln Leu Ser Ser Leu Thr Ser Glu Asp
            100                 105                 110

Ser Ala Asp Tyr Tyr Cys Ala Arg Ser Asn Tyr Tyr Gly Ser Ser Tyr
        115                 120                 125

Trp Phe Phe Asp Val Trp Gly Ala Gly Thr Thr Val Thr Val Ser Ser
    130                 135                 140

Gly Gly Gly Gly Ser Gly Gly Gly Ser Gly Gly Gly Gly Ser Asp
145                 150                 155                 160

Ile Val Leu Thr Gln Ser Pro Ala Ile Leu Ser Ala Ser Pro Gly Glu
                165                 170                 175

Lys Val Thr Met Thr Cys Arg Ala Ser Ser Ser Val Asn Tyr Met Asp
            180                 185                 190

Trp Tyr Gln Lys Lys Pro Gly Ser Ser Pro Lys Pro Trp Ile Tyr Ala
        195                 200                 205

Thr Ser Asn Leu Ala Ser Gly Val Pro Ala Arg Phe Ser Gly Ser Gly
    210                 215                 220

Ser Gly Thr Ser Tyr Ser Leu Thr Ile Ser Arg Val Glu Ala Glu Asp
225                 230                 235                 240
```

-continued

Ala Ala Thr Tyr Tyr Cys Gln Gln Trp Ser Phe Asn Pro Pro Thr Phe
                245                 250                 255

Gly Gly Gly Thr Lys Leu Glu Ile Lys Gly Gly Gly Ser Gly Gly
            260                 265                 270

Gly Gly Ser Gly Gly Gly Ser Gly Gly Gly Ser Gly Gly Gly
        275                 280                 285

Gly Ser Asp Ile Gln Met Thr Gln Thr Thr Ser Ser Leu Ser Ala Ser
    290                 295                 300

Leu Gly Asp Arg Val Thr Ile Ser Cys Arg Ala Ser Gln Asp Ile Ser
305                 310                 315                 320

Lys Tyr Leu Asn Trp Tyr Gln Gln Lys Pro Asp Gly Thr Val Lys Leu
                325                 330                 335

Leu Ile Tyr His Thr Ser Arg Leu His Ser Gly Val Pro Ser Arg Phe
            340                 345                 350

Ser Gly Ser Gly Ser Gly Thr Asp Tyr Ser Leu Thr Ile Ser Asn Leu
        355                 360                 365

Glu Gln Glu Asp Ile Ala Thr Tyr Phe Cys Gln Gln Gly Asn Thr Leu
    370                 375                 380

Pro Tyr Thr Phe Gly Gly Gly Thr Lys Leu Glu Ile Thr Gly Ser Thr
385                 390                 395                 400

Ser Gly Ser Gly Lys Pro Gly Ser Gly Glu Gly Ser Thr Lys Gly Glu
                405                 410                 415

Val Lys Leu Gln Glu Ser Gly Pro Gly Leu Val Ala Pro Ser Gln Ser
            420                 425                 430

Leu Ser Val Thr Cys Thr Val Ser Gly Val Ser Leu Pro Asp Tyr Gly
        435                 440                 445

Val Ser Trp Ile Arg Gln Pro Pro Arg Lys Gly Leu Glu Trp Leu Gly
    450                 455                 460

Val Ile Trp Gly Ser Glu Thr Thr Tyr Tyr Asn Ser Ala Leu Lys Ser
465                 470                 475                 480

Arg Leu Thr Ile Ile Lys Asp Asn Ser Lys Ser Gln Val Phe Leu Lys
                485                 490                 495

Met Asn Ser Leu Gln Thr Asp Asp Thr Ala Ile Tyr Tyr Cys Ala Lys
            500                 505                 510

His Tyr Tyr Tyr Gly Gly Ser Tyr Ala Met Asp Tyr Trp Gly Gln Gly
        515                 520                 525

Thr Ser Val Thr Val Ser Ser Ala Ala Ala Thr Thr Thr Pro Ala Pro
    530                 535                 540

Arg Pro Pro Thr Pro Ala Pro Thr Ile Ala Ser Gln Pro Leu Ser Leu
545                 550                 555                 560

Arg Pro Glu Ala Cys Arg Pro Ala Ala Gly Gly Ala Val His Thr Arg
                565                 570                 575

Gly Leu Asp Phe Ala Cys Asp Ile Tyr Ile Trp Ala Pro Leu Ala Gly
            580                 585                 590

Thr Cys Gly Val Leu Leu Leu Ser Leu Val Ile Thr Leu Tyr Cys Arg
        595                 600                 605

Ser Lys Arg Ser Arg Leu Leu His Ser Asp Tyr Met Asn Met Thr Pro
    610                 615                 620

Arg Arg Pro Gly Pro Thr Arg Lys His Tyr Gln Pro Tyr Ala Pro Pro
625                 630                 635                 640

Arg Asp Phe Ala Ala Tyr Arg Ser Arg Val Lys Phe Ser Arg Ser Ala
                645                 650                 655

```
Asp Ala Pro Ala Tyr Gln Gln Gly Gln Asn Gln Leu Tyr Asn Glu Leu
            660                 665                 670

Asn Leu Gly Arg Arg Glu Glu Tyr Asp Val Leu Asp Lys Arg Arg Gly
        675                 680                 685

Arg Asp Pro Glu Met Gly Gly Lys Pro Arg Arg Lys Asn Pro Gln Glu
    690                 695                 700

Gly Leu Tyr Asn Glu Leu Gln Lys Asp Lys Met Ala Glu Ala Tyr Ser
705                 710                 715                 720

Glu Ile Gly Met Lys Gly Glu Arg Arg Arg Gly Lys Gly His Asp Gly
                725                 730                 735

Leu Tyr Gln Gly Leu Ser Thr Ala Thr Lys Asp Thr Tyr Asp Ala Leu
            740                 745                 750

His Met Gln Ala Leu Pro Pro Arg
        755                 760

<210> SEQ ID NO 53
<211> LENGTH: 18
<212> TYPE: PRT
<213> ORGANISM: Artificial Sequence
<220> FEATURE:
<223> OTHER INFORMATION: Synthetic amino acid sequence

<400> SEQUENCE: 53

Gly Ser Thr Ser Gly Ser Gly Lys Pro Gly Ser Gly Glu Gly Ser Thr
1               5                   10                  15

Lys Gly

<210> SEQ ID NO 54
<211> LENGTH: 25
<212> TYPE: PRT
<213> ORGANISM: Artificial Sequence
<220> FEATURE:
<223> OTHER INFORMATION: synthetic amino acid sequence

<400> SEQUENCE: 54

Gly Gly Gly Gly Ser Gly Gly Gly Ser Gly Gly Gly Ser Gly
1               5                   10                  15

Gly Gly Gly Ser Gly Gly Gly Gly Ser
            20                  25
```